United States Patent
Maertens et al.

(10) Patent No.: US 11,384,374 B2
(45) Date of Patent: Jul. 12, 2022

(54) METABOLICALLY ENGINEERED ORGANISMS FOR THE PRODUCTION OF ADDED VALUE BIO-PRODUCTS

(71) Applicant: Inbiose N.V., Zwijnaarde (BE)

(72) Inventors: Jo Maertens, Ghent (BE); Joeri Beauprez, Bredene (BE); Marjan De Mey, Ghent (BE)

(73) Assignee: INBIOSE N.V., Zwijnaarde (BE)

( * ) Notice: Subject to any disclaimer, the term of this patent is extended or adjusted under 35 U.S.C. 154(b) by 0 days.

(21) Appl. No.: 16/599,921

(22) Filed: Oct. 11, 2019

(65) Prior Publication Data

US 2020/0140908 A1 May 7, 2020

Related U.S. Application Data

(62) Division of application No. 15/224,047, filed on Jul. 29, 2016, now Pat. No. 10,570,430, which is a division of application No. 13/809,340, filed as application No. PCT/EP2011/061891 on Jul. 12, 2011, now Pat. No. 9,701,992.

(30) Foreign Application Priority Data

Jul. 12, 2010 (EP) .................................... 10169304

(51) Int. Cl.
| | |
|---|---|
| *C12N 15/52* | (2006.01) |
| *C12N 15/70* | (2006.01) |
| *C12N 15/81* | (2006.01) |
| *C12N 9/10* | (2006.01) |
| *C12N 9/26* | (2006.01) |
| *C12N 9/90* | (2006.01) |
| *C12P 19/14* | (2006.01) |
| *C12P 19/18* | (2006.01) |
| *C12P 19/30* | (2006.01) |

(52) U.S. Cl.
CPC ............ *C12P 19/14* (2013.01); *C12N 9/1051* (2013.01); *C12N 9/2431* (2013.01); *C12N 9/90* (2013.01); *C12N 15/52* (2013.01); *C12N 15/70* (2013.01); *C12N 15/81* (2013.01); *C12P 19/18* (2013.01); *C12P 19/305* (2013.01); *C12Y 204/01007* (2013.01); *C12Y 204/01008* (2013.01); *C12Y 204/01022* (2013.01); *C12Y 204/01069* (2013.01); *C12Y 302/01026* (2013.01); *C12Y 504/02002* (2013.01)

(58) Field of Classification Search
CPC ......... C12P 19/14; C12P 19/18; C12P 19/305; C12N 9/1051; C12N 9/2431; C12N 9/90; C12N 15/70; C12N 15/81; C12N 15/52; C12Y 204/01007; C12Y 204/01008; C12Y 204/01022; C12Y 204/01069; C12Y 302/01026; C12Y 504/02002
See application file for complete search history.

(56) References Cited

U.S. PATENT DOCUMENTS

| | | |
|---|---|---|
| 5,716,837 A | 2/1998 | Barry et al. |
| 6,013,494 A | 1/2000 | Nakamura et al. |
| 7,214,517 B2 | 5/2007 | Kamada et al. |
| 7,422,880 B2 | 9/2008 | Rybak et al. |
| 7,851,188 B2 | 12/2010 | Donaldson et al. |
| 7,993,889 B1 | 8/2011 | Donaldson et al. |
| 8,017,375 B2 | 9/2011 | Feldman et al. |
| 8,232,089 B2 | 7/2012 | Urano et al. |
| 8,426,173 B2 | 4/2013 | Bramucci et al. |
| 2004/0058418 A1 | 3/2004 | Endo et al. |
| 2005/0186666 A1 | 8/2005 | Schneider et al. |
| 2007/0092957 A1 | 4/2007 | Donaldson et al. |
| 2008/0206822 A1 | 8/2008 | Fujii et al. |
| 2009/0082307 A1 | 3/2009 | Samain et al. |
| 2009/0226991 A1 | 9/2009 | Feldman et al. |
| 2011/0207187 A1 | 8/2011 | Tokuda et al. |

FOREIGN PATENT DOCUMENTS

| | | |
|---|---|---|
| EP | 1243647 A1 | 9/2002 |
| WO | WO 2002/081631 A2 | 10/2002 |
| WO | WO 2008/034158 A2 | 3/2008 |
| WO | WO 2008/137406 A1 | 11/2008 |
| WO | WO 2009/078687 A2 | 6/2009 |
| WO | WO 2010/051849 A1 | 5/2010 |
| WO | WO 2010/053052 A1 | 5/2010 |
| WO | WO 2010/055123 A2 | 5/2010 |

OTHER PUBLICATIONS

Tang et al., Phil Trans R Soc B 368:Mar. 18, 2012, 1-10, 2013.*
Aerts et al. (2010) "A constitutive expression system for high throughput screening," Engineering in Life Sciences 11(1):10-19.
Aerts et al. (May 7, 2013) "Consensus engineering of sucrose phosphorylase: The outcome reflects the sequence input," Biotechnology and Bioengineering. 110(10):2563-2572.
Agrawal et al. (2003) RNA Interference: Biology, Mechanism, and Applications, Microbiology and Molecular Biology Reviews 67:657-685.
Antoine et al. (2005) "Large scale in vivo synthesis of globotriose and globotetraose by high cell density culture of metabolically engineered *Escherichia coli*," Biochimie 87:197-203.
Atsumi et al. (2009) "Direct photosynthetic recycling of carbon dioxide to isobutyraldehyde," Nat. Biotechnol. 27(12):1177-1180.
Avihoo et al. (2007) "In silico design of small RNA switches," IEEE Transactions on Nanobioscience 6:4-11.

(Continued)

*Primary Examiner* — Delia M Ramirez
(74) *Attorney, Agent, or Firm* — Lathrop GPM LLP; James H. Velema; Judith L. Stone-Hulslander

(57) ABSTRACT

The present invention relates to genetically engineered organisms, especially microorganisms such as bacteria and yeasts, for the production of added value bio-products such as specialty saccharide, activated saccharide, nucleoside, glycoside, glycolipid or glycoprotein. More specifically, the present invention relates to host cells that are metabolically engineered so that they can produce said valuable specialty products in large quantities and at a high rate by bypassing classical technical problems that occur in biocatalytical or fermentative production processes.

19 Claims, 22 Drawing Sheets

Specification includes a Sequence Listing.

(56) References Cited

OTHER PUBLICATIONS

Ayres et al. (1993) "Precise Deletions in Large Bacterial Genomes by Vector-mediated Excision (VEX): The trfA Gene of Promiscuous Plasmid RK2 is Essential for Replication in Several Gram-negative Hosts," Journal of Molecular Biology 230:174-185.

Baba et al. (2006) "Construction of *Escherichia coli* K-12 in-frame, single-gene knockout mutants: the Keio collection," Molecular Systems Biology. Article No. 2006.0008. pp. 1-11.

Badet et al. (1987) "Glucosamine synthetase from *Escherichia coli*: purification, properties, and glutamine-utilizing site location," Biochemistry 26:1940-1948.

Balbás (2001) "Chromosomal editing in *Escherichia coli*," Molecular Biotechnology 19:1-12.

Balbás et al. (1996) "A pBRINT family of plasmids for integration of cloned DNA into the *Escherichia coli* chromosome," Gene 172:65-69.

Bartnicki-Garcia (1968) "Cell wall chemistry, morphogenesis, and taxonomy of fungi," Annu. Rev. Microbiol. 22:87-108.

Bastida et al. (2001) "Heterologous Over-expression of α-1,6-Fucosyltransferase from *Rhizobium* sp.: Application to the Synthesis of the Trisaccharide β-D-GlcNAc(1→4)-[α-L-Fuc-(1→6)]-D-GlcNAc, Study of the Acceptor Specificity and Evaluation of Polyhydroxylated Indolizidines as Inhibitors," Chemistry 7(11):2390-2397.

Beauprez (2010) "Metabolic modelling and engineering of *Escherichia coli* for succinate production," Ph.D. Dissertation. Ghent University, pp. 1-240.

Benson et al. (2010) "GenBank," Nucl. Acids Res. 38:D46-D51.

Bisso et al. (1999) "Structural and enzymatic characterization of human recombinant GDP-D-mannose-4,6-dehydratase," FEBS Lett. 456:370-374.

Boles et al. (1994) "A family of hexosephosphate mutases in *Saccharomyces cerevisiae*," European Journal of Biochemistry 220:83-96.

Branch (1998) "A good antisense molecule is hard to find," TIBS. 23:45-50.

Branden et al. (1991) In: Introduction to Protein Structure. Garland Publishing Inc. New York, New York. p. 247.

brenda-enzymes.org (Release Jul. 2016) "BRENDA: The Comprehensive Enzyme Information System," Accessible on the Internet at URL: http://www.brenda-enzymes.org. [Last Accessed Nov. 29, 2016].

Buchholz et al. (2001) "Quantification of Intracellular Metabolites in *Escherichia coli* K12 Using Liquid Chromatographic-Electrospray Ionization Tandem Mass Spectrometric Techniques," Analytical Biochemistry 295:129-137.

Burda et al. (1998) "The ALG10 locus of *Saccharomyces cerevisiae* encodes the α-1,2 glucosyltransferase of the endoplasmic reticulum: the terminal glucose of the lipid-linked oligosaccharide is required for efficient N-linked glycosylation," Glycobiology 8:455-462.

Byun et al. (2007) "Production of GDP-1-fucose, 1-fucose donor for fucosyloligosaccharide synthesis, in recombinant *Escherichia coli*," Applied Microbiology and Biotechnology 74:768-775.

Cardenas et al. (2001) "Novel microbial lipases: catalytic activity in reactions in organic media," Enzyme Microb. Technol. 28:145-154.

Cardenas et al. (2001) "Screening and catalytic activity in organic synthesis of novel fungal and yeast lipases," J. Mol. Catal. B: Enzymatic 14:111-123.

Causey et al. (2002) "Engineering *Escherichia coli* for efficient conversion of glucose to pyruvate," Proc. Natl. Acad. Sci. USA 101:2235-2240.

Chang (1999) "Homofermentative Production of d- or l-Lactate in Metabolically Engineered *Escherichia coli* RR1," Appl. Environ. Microbiol. 65:1384-1389.

Chang et al. (2009) "BRENDA, AMENDA and FRENDA the enzyme information system: new content and tools in 2009," Nucl. Acids Res. 37:D588-D592.

Cherepanov et al. (1995) "Gene disruption in *Escherichia coli*: TcR and KmR cassettes with the option of Flp-catalyzed excision of the antibiotic-resistance determinant," Gene 158:9-14.

Chow et al. (1983) "Identification and physical characterization of yeast maltase structural genes," Molecular and General Genetics 191:366-371.

Chow et al. (1989) "Structure of the multigene family of MAL loci in *Saccharomyces*," Molecular and General Genetics 217:60-69.

Czar et al. (2009) "Gene synthesis demystified," Trends in Biotechnology 27:63-72.

Daran et al. (1995) "Genetic and biochemical characterization of the UGP1 gene encoding the UDP-glucose pyrophosphorylase from *Saccharomyces cerevisiae*," European Journal of Biochemistry 233:520-530.

Datsenko et al. (2000) "One-step inactivation of chromosomal genes in *Escherichia coli* K-12 using PCR products," Proc. Natl. Acad. Sci. USA 97:6640-6645.

De Groeve et al. (2009) Enzymatic production of alpha-D-galactose 1-phosphate by lactose phosphorolysis, Biotechnology Letters 31:1873-1877.

De Groeve et al. (2010) "Development and Application of a Screening Assay for Glycoside Phosphorylases," Anal. Biochem. 401:162-167.

De Mey (2007) "Metabolic modelling and engineering of *Escherichia coli* to minimize acetate formation in recombinant DNA fermentation processes," Ph.D. Dissertation. Ghent University. pp. 1-222.

De Mey et al. (2004) "Promoter Engineering: A Useful Tool for Fine Tuning Gene Expression in *Escherichia coli*," In; The Abstract Book on the Symposium on the Crossroads of Microbiology and Informatics. Brussels, Belgium. Dec. 23, 2004. Abstact No. 29.

De Mey et al. (2007) "Construction and model-based analysis of a promoter library for *E. coli*: an indispensable tool for metabolic engineering," BMC Biotechnology 7:34. pp. 1-14.

De Virgilio et al. (1993) "Disruption of TPS2, the gene encoding the 100-kDa subunit of the trehalose-6-phosphate synthase/phosphatase complex in *Saccharomyces cerevisiae*, causes accumulation of trehalose-6-phosphate and loss of trehalose-6-phosphate phosphatase activity," European Journal of Biochemistry 212:315-323.

Dedhia et al. (1994) "Overproduction of glycogen in *Escherichia coli* blocked in the acetate pathway improves cell growth," Biotechnology and Bioengineering 44:132-139.

Dickinson (1991) "Biochemical and genetic studies on the function of, and relationship between, the PGI1- and CDC30-encoded phosphoglucose isomerases in *Saccharomyces cerevisiae*," Journal of General Microbiology 137:765-770.

Dippel et al. (2005) "The Maltodextrin System of *Escherichia coli*: Metabolism and Transport," J. Bacteriol. 187:8322-8331.

Drouillard et al. (2006) "Large-Scale of H-Antigen Oligosaccharides by Expressing Helicobacter pylori [alpha]1,2-Fucosyltransferase in Metabolically Engineered *Escherichia coli* Cells," Ang. Chem. Int. Ed. Eng. 45:1778-1780.

Dumon et al. (2001) "In vivo fucosylation of lacto-N-neotetraose and lacto-N-neohexaose by heterologous expression of Helicobacter pylori α-1,3 fucosyltransferase in engineered *Escherichia coli*," Glycoconjugate Journal 18:465-474.

Dumon et al. (2004) "Assessment of the Two Helicobacter pylori α-1,3-Fucosyltransferase Ortholog Genes for the Large-Scale Synthesis of LewisX Human Milk Oligosaccharides by Metabolically Engineered *Escherichia coli*," Blotechnol. Prog. 20:412-420.

Edwards et al. (1993) "UDP-sugar hydrolase isozymes in *Salmonella enterica* and *Escherichia coli*: Silent alleles of ushA in related strains of Group I *Salmonella* isolates, and of ushB in wild-type and K12 strains of *E. coli*, indicate recent and early silencing events, respectively," FEMS Microbiology Letters 114:293-298.

Egan et al. (1992) "Molecular characterization of the Entner-Doudoroff pathway in *Escherichia coli*: sequence analysis and localization of promoters for the edd-eda operon," Journal of Bacteriology 174:4638-4646.

Farkas et al. (1990) "Isolation of the GSY1 gene encoding yeast glycogen synthase and evidence for the existence of a second gene," Journal of Biological Chemistry 265:20879-20886.

(56) References Cited

OTHER PUBLICATIONS

Farkas et al. (1991) "Two glycogen synthase isoforms in *Saccharomyces cerevisiae* are coded by distinct genes that are differentially controlled," Journal of Biological Chemistry 266:15602-15607.
Flores et al. (2007) "Growth recovery on glucose under aerobic conditions of an *Escherichia coli* strain carrying a phosphoenolpyruvate:carbohydrate phosphotransferase system deletion by inactivating arcA and overexpressing the genes coding for glucokinase and galactose permease," Journal of Molecular Microbiology and Biotechnology 13:105-116.
Ge et al. (1997) "Cloning and Heterologous Expression of an Alpha1,3-Fucosyltransferase Gene from the Gastric Pathogen *Helicobacter pylori*," J. Biol. Chem. 34:21357-21363.
Gerdes et al. (2003) "Experimental Determination and System Level Analysis of Essential Genes in *Escherichia coli* MG1655," J. Bacteriol. 185:5673-5684.
Goedl et al. (2007) "Recombinant sucrose phosphorylase from Leuconostoc mesenteroides: characterization, kinetic studies oftransglucosylation, and application of immobilised enzyme for production of alpha-D-glucose 1-phosphate," Journal of Biotechnology 129:77-86.
Goedl et al. (2008) "Mechanistic Differences Among Retaining Disaccharide Phosphorylases: Insights From Kinetic Analysis of Active Site Mutants of Sucrose Phosphorylase and Alpha,alpha-Trehalose Phosphorylase," Carbohydr. Res. 343:2032-2040.
González-Pajuelo et al. (2006) "Microbial Conversion of Glycerol to 1,3-Propanediol: Physiological Comparison of a Natural Producer, Clostridium butyricum VPI 3266, and an Engineered Strain, Clostridium acetobutylicum DG1(pSPD5)," Appl. Environ. Microbiol. 72:96-101.
Gorsich et al. (2006) "Tolerance to furfural-induced stress is associated with pentose phosphate pathway genes ZWF1, GND1, RPE1, and TKL1 in *Saccharomyces cerevisiae*," Applied Microbiology and Biotechnology 71:339-349.
Grollman et al. (1965) "Biosynthesis of Fucosyllactose and Other Oligosaccharides Found in Milk," J. Biol. Chem. 240:975-981.
Gustaffson (2010) "Tools Designed to Regulate Translational Efficiency," Ch. 9 In; The Metabolic Pathway Engineering Handbook. Ed.: Smolke. CRC Press. Boca Raton, Florida, pp. 9-1-9-14.
Hashimoto et al. (1997) "*Saccharomyces cerevisiae* VIG9 encodes GDP-mannose pyrophosphorylase, which is essential for protein glycosylation," Journal of Biological Chemistry 272:16308-16314.
Hebert et al. (2008) "Beyond silencing—engineering applications of RNA interference and antisense technology for altering cellular phenotype," Current Opinion in Biotechnology 19:500-505.
Heinisch (1986) "Isolation and characterization of the two structural genes coding for phosphofructokinase in yeast," Molecular and General Genetics 202:75-82.
Heinisch et al. (1989) "The phosphofructokinase genes of yeast evolved from two duplication events," Gene 78:309-321.
Hoang et al. (1998) "A broad-host-range Flp-FRT recombination system for site-specific excision of chromosomally-located DNA sequences: application for isolation of unmarked Pseudomonas aeruginosa mutants," Gene 212:77-86.
Ishihara et al. (2007) "Homologous Subunits of 1,3-Beta-Glucan Synthase Are Important for Spore Wall Assembly in *Saccharomyces cerevisiae*," Eukaryotic Cell 6:143-156.
Jarvinen et al. (2001) "Cloning and expression of Helicobacter pylori GDP-L-fucose synthesizing enzymes (GMD and GMER) in *Saccharomyces cerevisiae*," Eur. J. Biochem. 268:6458-6464.
Joyce et al. (2006) "Experimental and Computational Assessment of Conditionally Essential Genes in *Escherichia coli*," J. Bacteriol. 188:8259-8271.
Kanehisa et al. (2010) "KEGG for representation and analysis of molecular networks involving diseases and drugs," Nucl. Acids Res. 38:D355-D360.
Keasling (1999) "Gene-expression tools for the metabolic engineering of bacteria," Trends in Biotechnology 17:452-460.
Kiino et al. (1993) "A cytoplasmic protein, NfrC, is required for bacteriophage N4 adsorption," Journal of Bacteriology 175:7074-7080.
Kim et al. (1997) "The D-allose operon of *Escherichia coli* K-12," J. Bacteriol. 179:7631-7637.
Kim et al. (2003) "Cloning and expression of sucrose phosphorylase gene from Bifidobacterium longum in *E. coli* and characterization of the recombinant enzyme," Biotechnology Letters. 25(15):1211-1217.
Kogure et al. (2007) "Efficient production of 2-deoxy-scyllo-inosose from d-glucose by metabolically engineered recombinant *Escherichia coli*," Journal of Biotechnology 129:502-509.
Koizumi et al. (1998) "Large-Scale Production of UDP-Galactose and Globotriose by Coupling metabolically engineered Bacteria," Nature Biotechnology. 16(9):847-950.
Kornberg (2001) "Routes for fructose utilization by *Escherichia coli*," Journal of Molecular Microbiology and Biotechnology 3:355-359.
Kozak (1999) "Initiation of translation in prokaryotes and eukaryotes," Gene. 234:187-208.
Kristensen et al. (1995) "Site-specificdeletions of chromosomally located DNA segments with the multimer resolution system of broad-host-range plasmid RP4," Journal of Bacteriology 177:52-58.
Kuznetsova et al. (2006) "Genome-wide Analysis of Substrate Specificities of the *Escherichia coli* Haloacid Dehalogenase-like Phosphatase Family," Journal of Biological Chemistry 281:36149-36161.
Lasserre et al. (2006) "A complexomic study of *Escherichia coli* using two-dimensional blue native/SDS polyacrylamide gel electrophoresis," Electrophoresis 27:3306-3321.
Lee et al. (2009) "Modulation of guanosine 5'-diphosphate-d-mannose metabolism in recombinant *Escherichia coli* for production of guanosine 5'-diphosphate-l-fucose," Bioresource Technol. 100:6143-6148.
Li et al. (2008) "Characterization of a Novel α1,2-Fucosyltransferase of *Escherichia coli* O128:B12 and Functional Investigation of Its Common," Biochemistry 47:378-387.
Liu et al. (2010) "Genetic engineering of *Escherichia coli* for biofuel production," Annu. Rev. Genetics 44:53-69.
Llull et al. (2001) "Tts, a Processive β-Glucosyltransferase of *Streptococcus pneumoniae*, Directs the Synthesis of the Branched Type 37 Capsular Polysaccharide in Pneumococcus and Other Gram-positive Species," Journal of Biological Chemistry 276:21053-21061.
Lopez et al. (1999) "The yeast inositol monophosphatase is a lithium- and sodium-sensitive enzyme encoded by a non-essential gene pair," Molecular Microbiology 31:1255-1264.
Lu et al. (2010) "Alteration of hydrogen metabolism of ldh-deleted Enterobacter aerogenes by overexpression of NAD+-dependent formate dehydrogenase," Appl. Microbiol. Biotechnol. 86:255-262.
Ma et al. (2006) "Fucosylation in prokaryotes and eukaryotes," Glycobiology 16:158R-184R.
Ma et al. (2010) "A Practical Guide to Fungal Genome Projects: Strategy, Technology, Cost and Completion," Mycology 1:9-24.
Maitra et al. (1973) "The intermediate in the uridine diphosphate galactose 4-epimerase reaction: Resolution of an apparent ambiguity," Journal of Biological Chemistry 248:1477-1479.
Markovitz et al. (1967) "Genetic and biochemical studies on mannose-negative mutants that are deficient in phosphomannose isomerase in *Escherichia coli* K-12," Journal of Bacteriology 94:1492-1496.
Marolda et al. (1996) "The GalF protein of *Escherichia coli* is not a UDP-glucose pyrophosphorylase but interacts with the GalU protein possibly to regulate cellular levels of UDP-glucose," Molecular Microbiology 22:827-840.
Marquardt et al. (1993) "Isolation and structural elucidation of a tetrahedral intermediate in the UDP-N-acetylglucosamine enolpyruvoyl transferase enzymic pathway," Journal of the American Chemical Society 115:10398-10399.
Martinez-Duncker et al. (2003) "A new superfamily of protein-O-fucosyltransferases, α2-fucosyltransferases, and α6-fucosyltransferases: phylogeny and identification of conserved peptide motifs," Glycobiology 13:1C-5C.

(56) References Cited

OTHER PUBLICATIONS

Mattila et al. (2000) "Functional expression of *Escherichia coli* enzymes synthesizing GDP-L-fucose from inherent GDP-D-mannose in *Saccharomyces cerevisiae*," Glycobiology 10:1041-1047.
Mazur et al. (1995) "Differential expression and function of two homologous subunits of yeast 1,3-beta-D-glucan synthase," Mol. Cell. Biol. 15:5671-5681.
Meijer et al. (2007) "ATG Genes Involved in Non-Selective Autophagy are Conserved from Yeast to Man, but the Selective Cvt and Pexophagy Pathways Also Require Organism-Specific Genes," Autophagy 3:106-116.
Moretti et al. (2007) "The M-Coffee web server: a meta-method for computing multiple sequence alignments by combining alternative alignment methods," Nucleic Acids Research 35:W645-W648.
Mu et al. (1996) "Initiation of Glycogen Synthesis in Yeast," Journal of Biological Chemistry 271:26554-26560.
Mueller et al. (2007) "The role of Asp-295 in the catalytic mechanism of Leuconostoc mesenteroides sucrose phosphorylase probed with site-directed mutagenesis," FEBS Lett. 581:1403-1408.
Mulichak et al. (2002) "Structure of the MUR1 GDP-Mannose 4,6-Dehydratase from *Arabidopsis thaliana*: Implications for Ligand Binding and Specificity," Biochemistry 41:15578-15589.
Muller et al. (1997) "Mutant studies of phosphofructo-2-kinases do not reveal an essential role of fructose-2, 6-bisphosphate in the regulation of carbon fluxes in yeast cells," Microbiology 143:3055-3061.
Murray et al. (2000) "Expression of yeast INM1 encoding inositol monophosphatase is regulated by inositol, carbon source and growth stage and is decreased by lithium and valproate," Molecular Microbiology 36:651-661.
Na et al. (2010) "Construction and optimization of synthetic pathways in metabolic engineering," Curr. Opin. Microbiol. 13:363-370.
Nakashima et al. (Feb. 18, 2014) "Bacterial Cellular Engineering by Genome Editing and Gene Silencing," Int. J. Mol. Sci. 15:2773-2793.
Nassau et al. (1996) Galactofuranose biosynthesis in *Escherichia coli* K-12: identification and cloning of UDP-galactopyranose mutase, J. Bacteriol. 178:1047-1052.
Neville (2008) "Milk Secretion: An Overview," Health e-Learning. Accessible on the Internet at URL: https://www.health-e-learning.com/articles/Neville_MILK_SECRETION_2008.pdf [Last Accessed Nov. 29, 2016].
Nielsen et al. (2009) "Engineering alternative butanol production platforms in heterologous bacteria," Metab. Eng. 11:262-273.
Nogae et al. (1990) "Isolation and characterization of the ZWF1 gene of *Saccharomyces cerevisiae*, encoding glucose-6-phosphate dehydrogenase," Gene 96:161-169.
Novotny et al. (1984) "Purification and properties of D-mannitol-1-phosphate dehydrogenase and D-glucitol-6-phosphate dehydrogenase from *Escherichia coli*," J. Bacteriol. 159:986-990.
Oh et al. (1997) "ELO2 and ELO3, homologues of the *Saccharomyces cerevisiae* ELO1 gene, function in fatty acid elongation and are required for sphingolipid formation," Journal of Biological Chemistry 272:17376-17384.
Oriol et al. (1999) "Divergent evolution of fucosyltransferase genes from vertebrates, invertebrates, and bacteria," Glycobiology 9:323-334.
Persson et al. (2008) "A high-throughput pH indicator assay for screening glycosyltransferase saturation mutagenesis libraries," Analytical Biochemistry 378:1-7.
Porchia et al. (1996) "Sucrose biosynthesis in a prokaryotic organism: Presence of two sucrose-phosphate synthases in Anabaena with remarkable differences compared with the plant enzymes," Proc. Natl. Acad. Sci. USA 93:13600-13604.
Priem et al. (2002) "A new fermentation process allows large-scale production of human milk oligosaccharides by metabolically engineered bacteria," Glycobiology 12:235-240.

Rabina et al. (2000) "Two Time-Resolved Fluorometric High-Throughput Assays for Quantitation of GDP-L-Fucose," Anal. Biochem. 286:173-178.
Ramakrishnan et al. (2001) "Crystal structure of lactose synthase reveals a large conformational change in its catalytic component, the [beta]1,4-galactosyltransferase-I," Journal of Molecular Biology 310:205-218.
Ramakrishnan et al. (2001) "α-Lactalbumin (LA) Stimulates Milk β-1,4-Galactosyltransferase I (β4Gal-T1) to Transfer Glucose from UDP-glucose to N-Acetylglucosamine," Journal of Biological Chemistry 276:37665-37671.
Rasmussen et al. (2007) "Hitting bacteria at the heart of the central dogma: sequence-specific inhibition," Microbial Cell Factories 6:24.
Ren et al. (2010) "Biochemical characterization of GDP-L-fucose de novo synthesis pathway in fungus *Mortierella alpina*," Biochem. Biophys. Res. Commun. 391:1663-1669.
Rider et al. (2004) "6-phosphofructo-2-kinase/fructose-2,6-bisphosphatase: Head-to-head with a bifunctional enzyme that controls glycolysis," Biochemical Journal 381:561-579.
Rodriguez et al. (2001) "The hexokinase 2 protein regulates the expression of the GLK1, HXK1 and HXK2 genes of *Saccharomyces cerevisiae*," Biochem. J. 355:625-631.
Rosano et al. (2000) "Probing the catalytic mechanism of GDP-4-keto-6-deoxy-d-mannose epimerase/reductase by kinetic and crystallographic characterization of site-specific mutants," J. Mol. Biol. 303:77-91.
Ruffing et al. (2006) "Metabolic engineering of microbes for oligosaccharide and polysaccharide synthesis," Microbial Cell Factories 5:25. pp. 1-9. Ruffing et al. (2009) In; Microbial Production of Biopolymers and Polymer Precursors: Applications and Perspectives. Ed.: Rehm. Caister Academic Press. Haverhill, United Kingdom, pp. 197-228.
Rush et al. (1997) "Polyisoprenyl phosphate specificity of UDP-GlcNAc:undecaprenyl phosphate N-acetylglucosaminyl 1-P transferase from *E.coli*," Glycobiology 7:315-322.
Sabri et al., "Molecular Control of Sucrose Utilization in *Escherichia coli* W, an Efficient Sucrose-Utilizing Strain", Applied and Environmental Microbiology 79(2): 478-487, 2013.
Sadowski et al. (2009) "The sequence-structure relationship and protein function prediction," Current Opinion in Structural Biology. 19:357-362.
Sauer (1987) "Functional expression of the cre-lox site-specific recombination system in the yeast *Saccharomyces cerevisiae*," Molecular and Cellular Biology 7:2087-2096.
Schwarz et al. (2008) "Acid-base catalysis in Leuconostoc mesenteroides sucrose phosphorylase probed by site-directed mutagenesis and detailed kinetic comparison of wild-type and Glu237→Gln mutant enzymes," Biochem. J. 403:441-449.
Schweizer (2003) "Applications of the *Saccharomyces cerevisiae* Flp-FRT system in bacterial genetics," Journal of Molecular Microbiology and Biotechnology 5:67-77.
Seffernick et al. (2001) "Melamine Deaminase and Atrazine Chlorohydrolase: 98 Percent Identical but Functionally Different," J. Bacteriol. 183(8):2405-2410.
Segawa et al. (1979) "The enzymes of the galactose cluster in *Saccharomyces cerevisiae*. Purification and characterization of galactose-1-phosphate uridylyltransferase," Journal of Biological Chemistry 254:10707-10709.
Shaw et al. (2008) "Metabolic engineering of a thermophilic bacterium to produce ethanol at high yield," Proc. Natl. Acad. Sci. USA 105:13769-13774.
Sinnott (1978) "Ions, ion-pairs and catalysis by the lacZ β-galactosidase of *Escherichia coli*," FEBS Letters 94:1-9.
Smith et al. (1992) "PMI40, an intron-containing gene required for early steps in yeast mannosylation," Mol. Cell. Biol. 12:2924-2930.
Smith et al. (2010) "Engineering Corynebacterium glutamicum for isobutanol production," Appl. Microbiol. Biotechnol. 87:1045-1055.
Stagljar et al. (1994) New phenotype of mutations deficient in glucosylation of the lipid-linked oligosaccharide: cloning of the ALG8 locus, Proc. Natl. Acad. Sci. USA 91:5977-5981.

(56) References Cited

OTHER PUBLICATIONS

Steen et al. (2008) "Metabolic engineering of *Saccharomyces cerevisiae* for the production of n-butanol," Microb. Cell Fact. 7:36. pp. 1-8.
Stein et al. (2008) "Characterization of Helicobacter pylori α1,2-Fucosyltransferase for Enzymatic Synthesis of Tumor-Associated Antigens," Adv. Synth. Catal. 350:2313-2321.
Sternberg et al. (1981) "Bacteriophage P1 site-specific recombination. II. Recombination between loxP and the bacterial," Journal of Molecular Biology 150:487-507.
Stevenson et al. (1994) "Structure of the O antigen of *Escherichia coli* K-12 and the sequence of its rfb gene cluster," Journal of Bacteriology 176:4144-4156.
Stevenson et al. (1996) "Organization of the *Escherichia coli* K-12 gene cluster responsible for production of the extracellular polysaccharide colanic acid," Journal of Bacteriology 178:4885-4893.
Structural Genomics Consortium et al. (2008) "Protein production and purification," Nature Methods 5:135-146.
Sullivan et al. (1998) "Molecular Cloning of Human GDP-mannose 4,6-Dehydratase and Reconstitution of GDP-fucose Biosynthesis in Vitro," J. Biol. Chem. 273:8193-8202.
Sung et al. (2006) "Development of a Biofilm Production-Deficient *Escherichia coli* Strain as a Host for Biotechnological Applications," Appl. Environ. Microbiol. 72:3336-3342.
Suwannakham et al. (2006) "Construction and characterization of ack knock-out mutants of Propionibacterium acidipropionici for enhanced propionic acid fermentation," Biotechnol. Bioeng. 94:383-395.
Takahashi et al. (2000) "A Sequence Motif Involved in the Donor Substrate Binding by Alpha1,6-Fucosyltransferase: The Role of the Conserved Arginine Residues," Glycobiology 10:503-510.
Tallon et al. (2003) "Isolation and characterization of two exopolysaccharides produced by Lactobacillus plantarum EP56," Research in Microbiology 154:705-712.
Taussig et al. (1983) "Nucleotide sequence of the yeast SUC2 gene for invertase," Nucleic Acids Research 11:1943-1954.
Teste et al. (2010) "Characterization of a New Multigene Family Encoding Isomaltases in the Yeast *Saccharomyces cerevisiae*, the IMA Family," Journal of Biological Chemistry 285:26815-26824.
Thoden et al. (2005) "The molecular architecture of galactose mutarotase/UDP-galactose 4-epimerase from *Saccharomyces cerevisiae*," Journal of Biological Chemistry 280:21900-21907.
Tonouchi et al. (1998) "Increased Cellulose Production from Sucrose by Acetobacter after Introducing the Sucrose Phosphorylase Gene," Biosci. Biotechnol. Biochem. 62:1778-1780.
Trethewey et al. (1999) "Tuber-specific expression of a yeast invertase and a bacterial glucokinase in potato leads to an activation of sucrose phosphate synthase and the creation of a sucrose futile cycle," Planta. 208(2):227-238.
Trinchera et al. (1996) "Dictyostelium cytosolic fucosyltransferase synthesizes H type 1 trisaccharide in vitro," FEBS Letters 395:68-72.
Tsuda (1998) "Use of a transposon-encoded site-specific resolution system for construction of large and defined deletion mutations in bacterial chromosome," Gene 207:33-41.
Vanderpool et al. (2004) "Involvement of a novel transcriptional activator and small RNA in post-transcriptional regulation of the glucose phosphoenolpyruvate phosphotransferase system," Molecular Microbiology. 54(4):1076-1089.
Vuorio et al. (1995) "Comparison of the phenotypes of the lpxA and lpxD mutants of *Escherichia coli*," FEMS Microbiology Letters 134:227-232.
Wang et al. (1999) "Novel Helicobacter pylori [alpha]1,2-fucosyltransferase, a key enzyme in the synthesis of Lewis antigens," Microbiology 145:3245-3253.
Wang et al. (2001) "Modeling of inducer exclusion and catabolite repression based on a PTS-dependent sucrose and non-PTS-dependent glycerol transport systems in *Escherichia coli* K-12 and its experimental verification," Journal of Biotechnology 92:133-158.
Watzele et al. (1989) "Cloning of the glutamine:fructose-6-phosphate amidotransferase gene from yeast. Pheromonal regulation of its transcription," Journal of Biological Chemistry 264:8753-8758.
Wedekind et al. (1996) "The Structure of Nucleotidylated Histidine-166 of Galactose-1-phosphate Uridylyltransferase Provides Insight into Phosphoryl Group Transfer," Biochemistry 35:11560-11569.
Weissborn et al. (1994) "UTP: alpha-D-glucose-1-phosphate uridylyltransferase of *Escherichia coli*: isolation and DNA sequence of the galU gene and purification of the enzyme," Journal of Bacteriology 176:2611-2618.
wikipedia.org (Last Modified Nov. 8, 2016) "Glycosylation," Wikimedia Foundation, Inc. Accessible on the Internet at URL: https://en.wikipedia.org/wiki/Glycosylation. [Last Accessed Nov. 29, 2016].
Williams et al. (2009) "Strain engineering by genome mass transfer: Efficient chromosomal trait transfer method utilizing donor genomic DNA and recipient recombineering hosts," Molecular Biotechnology 43:41-51.
Witkowski et al. (1999) "Conversion of a β-Ketoacyl Synthase to a Malonyl Decarboxylase by Replacement of the Active-Site Cysteine with Glutamine," Biochemistry. 38:11643-11650.
Wu et al. (2001) "Identification and characterization of GDP-d-mannose 4,6-dehydratase and GDP-l-fucose synthetase in a GDP-l-fucose biosynthetic gene cluster from Helicobacter pylori," Biochem. Biophys. Res. Commun. 285:364-371.
Yamamoto et al. (2004) "Val216 decides the substrate specificity of α-glucosidase in *Saccharomyces cerevisiae*," European Journal of Biochemistry 271:3414-3420.
Yang et al. (2007) "Fermentation of 1,3-propanediol by a lactate deficient mutant of Klebsiella oxytoca under microaerobic conditions," Appl. Microbiol. Biotechnol. 73:1017-1024.
Zhang et al. (2003) Large-scale synthesis of globotriose derivatives through recombinant *E. coli*, Organic & Biomolecular Chemistry 1:3048-3053.
Zhao et al. (2004) "Global metabolic response of *Escherichia coli* to gnd or zwf gene-knockout, based on 13C-labeling experiments and the measurement of enzyme activities," Applied Microbiology and Biotechnology 64:91-98.
Zhou et al. (2006) "Global Analysis of Gene Transcription Regulation in Prokaryotes," Cell Mol Life Sci. 63(19-20):2260-2290.
Zhu (2005) "Construction and characterization of pta gene-deleted mutant of Clostridium tyrobutyricum for enhanced butyric acid fermentation," Biotechnol. Bioeng. 90:154-166.
International Preliminary Report on Patentability corresponding to International Patent Application No. PCT/EP2011/061891, dated Jan. 15, 2013.
International Search Report corresponding to International Patent Application No. PCT/EP2011/061891, dated Jan. 25, 2012.
Partial European Search Report corresponding to European Application No. 10169304, dated Jun. 10, 2011.

* cited by examiner

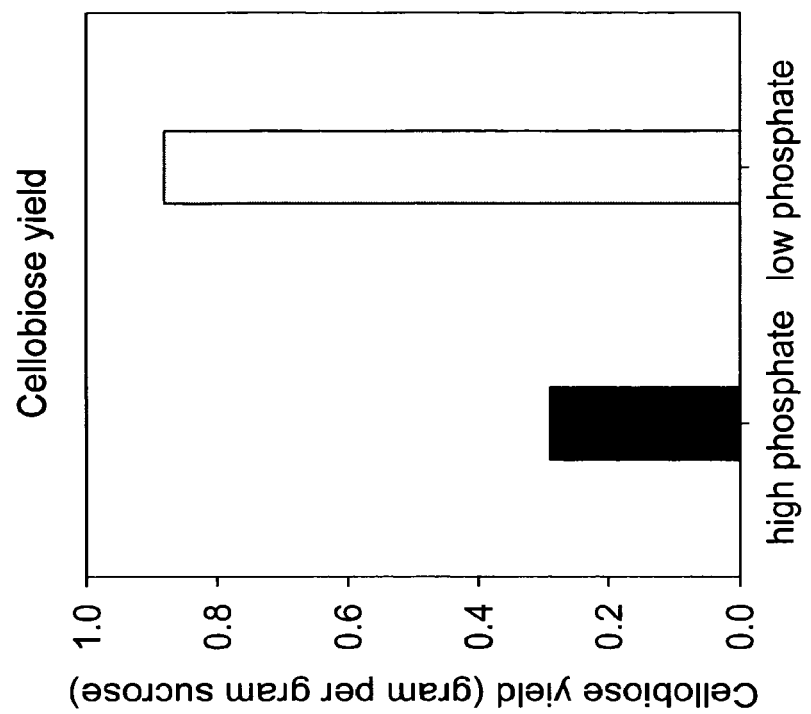
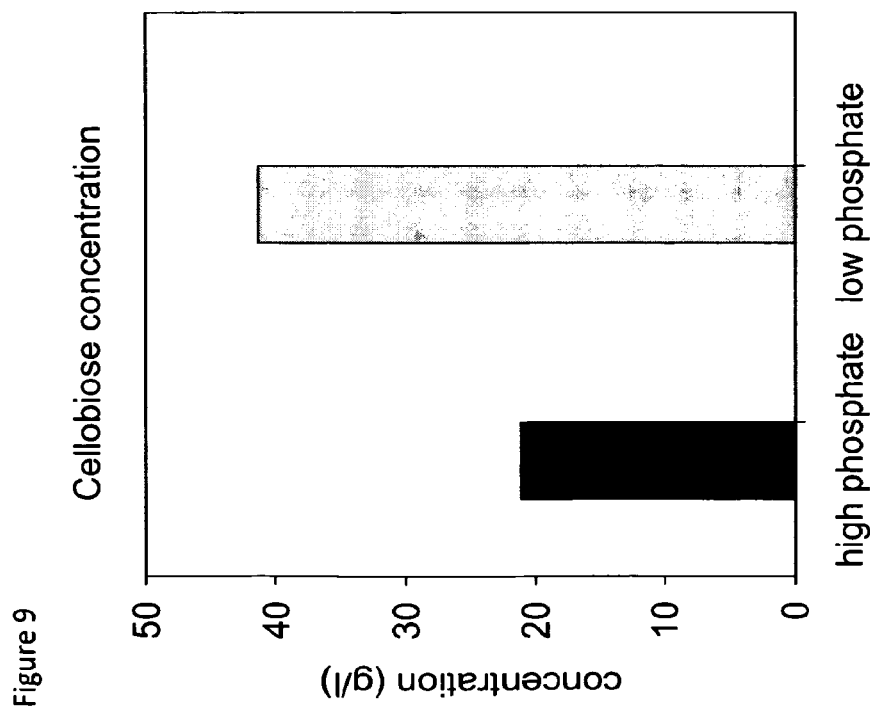
Figure 9

Figure 11

AGCATGATCGAACACATCATGCAGTCGATGCAATTCCCGGCGGAATTGATTGAGAAGG
TTTGCGGAACTATCTAAAACGTTGCAGACAAAGGACAAAGCA*ATGGCAATCCACAATC*
*GTGCAGGCCAACCTGCACAACAGAGTGATTTGATTAACGTCGCCCAACTGACGGCGCA*
*ATATTATGTACTGAAACCAGAAGCAGGGAATGCGGAGCACGCGGTGAAATTCGGTACT*
*TCCGGTCACCGTGGCAGTGCAGCGCGCCACAGCTTTAACGAGCCGCACATTCTGGCGA*
*TCGCTCAGGCAATTGCTGAAGAACGTGCGAAAAACGGCATCACTGGCCCTTGCTATGT*
*GGGTAAAGATACTCACGCCCTGTCCGAACCTGCATTCATTTCCGTTCTGGAAGTGCTG*
*GCAGCGAACGGCGTTGATGTCATTGTGCAGGAAAACAATGGCTTCACCCCGACGCCTG*
*CCGTTTCCAATGCCATCCTGGTTCACAATAAAAAAGGTGGCCCGCTGGCAGACGGTAT*
*CGTGATTACACCGTCCCATAACCCGCCGGAAGATGGTGGAATCAAATACAATCCGCCA*
*AATGGTGGCCCGGCTGATACCAACGTCACTAAAGTGGTGGAAGACAGGGCCAACGCAC*
*TGCTGGCCGATGGCCTGAAAGGCGTGAAGCGTATCTCCCTCGACGAAGCGATGGCATC*
*CGGTCATGTGAAAGAGCAGGATCTGGTGCAGCCGTTCGTGGAAGGTCTGGCCGATATC*
*GTTGATATGGCCGCGATTCAGAAAGCGGGCCTGACGCTGGGCGTTGATCCGCTGGGCG*
*GTTCCGGTATCGAATACTGGAAGCGTATTGGCGAGTATTACAACCTCAACCTGACTAT*
*CGTTAACGATCAGGTCGATCAAACCTTCGCTTTATGCACCTTGATAAAGACGGCGCG*
*ATCCGTATGGACTGCTCCTCCGAGTGTGCGATGGCGGGCCTGCTGGCACTGCGTGATA*
*AGTTCGATCTGGCGTTTGCTAACGACCCGGATTATGACCGTCACGGTATCGTCACTCC*
*GGCAGGTTTGATGAATCCGAACCACTACCTGGCGGTGGCAATCAATTACCTGTTCCAG*
*CATCGTCCGCAGTGGGCAAAGATGTTGCCGTCGGTAAAACGCTGGTTTCATCTGCGA*
*TGATCGACCGTGTGGTCAACGACTTGGGCCGTAAACTGGTAGAAGTCCCGGTAGGTTT*
*CAAATGGTTTGTCGATGGTCTGTTCGACGGCAGCTTCGGCTTTGGCGGCAAGAGAGT*
*GCAGGGGCTTCCTTCCTGCGTTTCGACGGCACGCCGTGGTCCACCGACAAAGACGGCA*
*TCATCATGTGTCTGCTGGCGGCGGAAATCACCGCTGTCACCGGTAAGAACCCGCAGGA*
*ACACTACAACGAACTGGCAAAACGCTTTGGTGCGCCGAGCTACAACCGTTTGCAGGCA*
*GCTGCGACTTCCGCACAAAAAGCGGCGCTGTCTAAGCTGTCTCCGGAAATGGTGAGCG*
*CCAGCACCCTGGCAGGTGACCCGATCACCGCGCGCCTGACTGCTGCTCCGGGCAACGG*
*TGCTTCTATTGGCGGTCTGAAAGTGATGACTGACAACGGCTGGTTCGCCGCGCGTCCG*
*TCAGGCACGGAAGACGCATATAAGATCTACTGCGAAAGCTTCCTCGGTGAAGAACATC*
*GCAAGCAGATTGAGAAAGAAGCGGTTGAGATTGTTAGCGAAGTTCTGAAAAACGCGTA*
AACACATTTAATAAAAAAGGGCGGTCGCAAGATCGCCCTTTTTTACGTATGACAAAC
ACAGAATTGCCTGATGCGCTACGCTTATCAGGCCTACGAGGAT

Figure 12

CGTACACGCGTTTACTTTGCGGCAGATGAACAAACGCTGCTGAAAAATGGTAA
TCAGACCAAGCCGAAACATGTGCCAGGCACGCCGTATTGGGTGATCACCAACA
CCAACACCGGCCGTAAATGCAGCATGATCGAACACATCATGCAGTCGATGCAA
TTCCCGGCGGAATTGATTGAGAAGGTTTGCGGAACTATCTAAAACGTTGCAGA
CAAAGGACAAAGCA*GTGTAGGCTGGAGCTGCTTCGAAGTTCCTATACTTTCTA*
*GAGAATAGGAACTTCGGAATAGGAACTAAGGAGGATATTCATATG*ACACATTT
AATAAAAAAGGGCGGTCGCAAGATCGCCCTTTTTTACGTATGACAAACACAG
AATTGCCTGATGCGCTACGCTTATCAGGCCTACGAGGATGGTGCAATATATTG
AATTTAAGCGATTTTGTAGGCCGGATAAGGCGTTCACGCCGCATCCGGCAAAA
ACAACGAACACTTTGTCAACAAACTGAGTAGC

Figure 13

CGTACACGCGTTTACTTTGCGGCAGATGAACAAACGCTGCTGAAAAATGGTAATCA
GACCAAGCCGAAACATGTGCCAGGCACGCCGTATTGGGTGATCACCAACACCAACA
CCGGCCGTAAATGCAGCATGATCGAACACATCATGCAGTCGATGCAATTCCCGGCG
GAATTGATTGAGAAGGTTTGCGGAACTATCTAAACGTTGCAGACAAAGGACAAAG
CA*GTGTAGGCTGGAGCTGCTTCGAAGTTCCTATACTTTCTAGAGAATAGGAACTTC*
*GGAATAGGAACTAAGGAGGATATTCATATGGACCGATATCCCGGGCGGCCGCTTCA*
*TTTATAAATTTCTTGACATTTTGGAATAGATGTGATATAATGTGTACATATCCATG*
*GCGGCCGCTCTAGAAGAAGCTTGGGATCCGTCGACCTCGAATTCGGAGGAAACAAA*
*GATGGGGGGTTCTCATCATCATCATCATGGTATGGCTAGCATGAGTAAAGGAG*
*AAGAACTTTTCACTGGAGTTGTCCCAATTCTTGTTGAATTAGATGGTGATGTTAAT*
*GGGCACAAATTTTCTGTCAGTGGAGAGGGTGAAGGTGATGCAACATACGGAAAACT*
*TACCCTTAAATTTATTTGCACTACTGGAAAACTACCTGTTCCATGGCCAACACTTG*
*TCACTACTTTCGGGTATGGTGTTCAATGCTTTGCNAGATACCCAGATCATATGAAA*
*CAGCATGACTTTTTCAAGAGTGCCATGCCCGAAGGTTATGTACAGGAAGAACTAT*
*ATTTTTCAAAGATGACGGGAACTACAAGACACGTGCTGAAGTCAAGTTTGAAGGTG*
*ATACCCTTGTTAATAGAATCGAGTTAAAAGGTATTGATTTTAAAGAAGATGGAAAC*
*ATTCTTGGACACAAATTGGAATACAACTATAACTCACACAATGTATACATCATGGC*
*AGACAAACAAAAGAATGGAATCAAAGTTAACTTCAAAATTAGACACAACATTGAAG*
*ATGGAAGCGTTCAACTAGCAGACCATTATCAACAAAATACTCCAATTGGCGATGGC*
*CCTGTCCTTTTACCAGACAACCATTACCTGTCCACACAATCTGCCCTTTCGAAAGA*
*TCCCAACGAAAGAGAGACCACATGGTCCTTCTTGAGTTTGTAACAGCTGCTGGGA*
*TTACACATGGCATGGATGAACTATACAAATAACTGCAGGTCGACCATATGGGAGAG*
*CTCCCAACGCGTTGGATGCAGGCATGCAAGCTTGGCTGTTTTGGCGGATGAGAGAA*
*GATTTTCAGCCTGATACAGATTAAATCAGAACGCAGAAGCGGTCTGATAAAACAGA*
*ATTTGCCTGGCGGCAGTAGCGCGGTGGTCCCACCTGACCCCATGCCGAACTCAGAA*
*GTGAAACGCCGTAGCGCCGATGGTAGTGTGGGGTCTCCCCATGCGAGAGTAGGGAA*
*CTGCCAGGCATCAAATAAAACGAAAGGCTCAGTCGAAAGACTGGGCCTTTCGTTTT*
*ATCTGTTGTTTGTCGGTGAACGCTCTCCTGAGTAGGACAAATCCGCCGGGAGCGGA*
*TTTGAACGTTGCGAAGCAACGGCCGGAGGGTGGCGGGCAGGACGCCCGCCATAAA*
*CTGCCAGGCATCAAATTAAGCAGAAGGCCATCCTGACGGATG*CTACTGCGAAAGCT
TCCTCGGTGAAGAACATCGCAAGCAGATTGAGAAGAAGCGGTTGAGATTGTTAGC
GAAGTTCTGAAAAACGCGTAACTACTGCGAAAGCTTCCTCGGTGAAGAACATCGCA
AGCAGATTGAGAAGAAGCGGTTGAGATTGTTAGCGAAGTTCTGAAAAACGCGTAA
ACACATTTAATAAAAAAGGGCGGTCGCAAGATCGCCCTTTTTTACGTATGACAAA
CACAGAATTGCCTGATGCGCTACGCTTATCAGGCCTACGAGGATGGTGCAATATAT
TGAATTTAAGCGATTTTGTAGGCCGGATAAGGCGTTCACGCCGCATCCGGCAAAAA
CAACGAACACTTTGTCAACAAACTGAGTAGCTCAAGGAAATCCCA

Figure 14

CGTACACGCGTTTACTTTGCGGCAGATGAACAAACGCTGCTGAAAAATGGTAATC
AGACCAAGCCGAAACATGTGCCAGGCACGCCGTATTGGGTGATCACCAACACCAA
CACCGGCCGTAAATGCAGCATGATCGAACACATCATGCAGTCGATGCAATTCCCG
GCGGAATTGATTGAGAAGGTTTGCGGAACTATCTAAAACGTTGCAGACAAAGGAC
AAAGCAACGAAAGGCTCAGTCGAAAGACTGGGCCTTTCGTTTTATCTGTTGTTTG
TCGGTGAACGCTCTCCTGAGTAGGACAAATCCGCCGGGAGCGGATTTGAACGTTG
CGAAGCAACGGCCCGGAGGGTGGCGGGCAGGACGCCCGCCATAAACTGCCAGGCA
TCAAATTAAGCAGAAGGCCATCCTGACGGATGGCCTTTTTGCGTGGCCAGTGCCA
AGCTTGCATGCAGATTGCAGCATTACACGTCTTGAGCGATTGTGTAGGCTGGAGC
TGCTTCGAAGTTCCTATACTTTCTAGAGAATAGGAACTTCGGAATAGGAACTTCA
AGATCCCCTCACGCTGCCGCAAGCACTCAGGGCGCAAGGGCTGCTAAAGGAAGCG
GAACACGTAGAAAGCCAGTCCGCAGAAACGGTGCTGACCCCGGATGAATGTCAGC
TACTGGGCTATCTGGACAAGGGAAAACGCAAGCGCAAAGAGAAAGCAGGTAGCTT
GCAGTGGGCTTACATGGCGATAGCTAGACTGGGCGGTTTTATGGACAGCAAGCGA
ACCGGAATTGCCAGCTGGGGCGCCCTCTGGTAAGGTTGGGAAGCCCTGCAAAGTA
AACTGGATGGCTTTCTTGCCGCCAAGGATCTGATGGCGCAGGGGATCAAGATCTG
ATCAAGAGACAGGATGAGGATCGTTTCGCAAGATCCCCTCACGCTGCCGCAAGCA
CTCAGGGCGCAAGGGCTGCTAAAGGAAGCGGAACACGTAGAAAGCCAGTCCGCAG
AAACGGTGCTGACCCCGGATGAATGTCAGCTACTGGGCTATCTGGACAAGGGAAA
ACGCAAGCGCAAAGAGAAAGCAGGTAGCTTGCAGTGGGCTTACATGGCGATAGCT
AGACTGGGCGGTTTTATGGACAGCAAGCGAACCGGAATTGCCAGCTGGGGCGCCC
TCTGGTAAGGTTGGGAAGCCCTGCAAAGTAAACTGGATGGCTTTCTTGCCGCCAA
GGATCTGATGGCGCAGGGGATCAAGATCTGATCAAGAGACAGGATGAGGATCGTT
TCGCGCGGGACTCTGGGGTTCGAAATGACCGACCAAGCGACGCCCAACCTGCCAT
CACGAGATTTCGATTCCACCGCCGCCTTCTATGAAAGGTTGGGCTTCGGAATCGT
TTTCCGGGACGCCGGCTGGATGATCCTCCAGCGCGGGGATCTCATGCTGGAGTTC
TCTACTGCGAAAGCTTCCTCGGTGAAGAACATCGCAAGCAGATTGAGAAAGAAGC
GGTTGAGATTGTTAGCGAAGTTCTGAAAAACGCGTAAACACATTTAATAAAAAAA
GGGCGGTCGCAAGATCGCCCTTTTTACGTATGACAAACACAGAATTGCCTGATG
CGCTACGCTTATCAGGCCTACGAGGATGGTGCAATATATTGAATTTAAGCGATTT
TGTAGGCCGGATAAGGCGTTCACGCCGCATCCGGCAAAAACAACGAACACTTTGT
CAACAAACTGAGTAGCTCAAGGAAATCCCA

Figure 19

```
ClustalW2 alignment Helicobacter pylori vs. Dictyostelium discoideum FT domain
Alignment Score -68

Dictyostelium     ---SILNFISGINSNKINTPKSNNNKFKENGIRIICFSKDRAFQLKEYLRTFFKYLKNDD   57
Helicobacter      MAFKVVRICGGLGNQMFQYAFAKSLQKHSNTPVLLDITSFDWSNRKMQLELFPIDLPYAS   60
                     : .* :: .: ::: : .:*    . :  :  * * . *  .

Dictyostelium     NGNDKFEIIVDVLFTYSNEKFKNSYQLVIESFPQVNFIKE-ENFTDQLINLVQKTNKLEY   116
Helicobacter      AK-------EIAIAKMQHLPKLVRDALKYIGFDRVSQEIVFEYEPKLLKPSRLTY        108
                   *::: :** ::: :.*.     :  *.:.:* *

Dictyostelium     VMFSVDDILYYNEFN-LKEYCLSLNSEPLALGFYMKLNKNITYCHTCNQDITIPLNSNTI   175
Helicobacter      FYGYFQDPRYFDAISPLIKQTFTLPPPPKIIRIIIKKEE---EYHRKLALILAAKNSVFV   165
                   .:* *:::..*  . :.:* : :.:*   *  . ** .  ::

Dictyostelium     SRTENNFKYLKWNRNDNDCKKDWNYPWDLCSTIYRCNDIDSIINGIVKYYGIRNGINHPN   235
Helicobacter      HIRRGDYVGIGCQLGIDYQKKALEY--------------MAKRVPN--MELFVFCEDLTFTQ   211
                   .    :: ::..:  :: .**  :*          .: :: :::::::

Dictyostelium     RFEFNGNRPIIQKQIYQNKPYCLCLSDHYSPMSVVTINRVQDVYDNPIYDQTLSLDDLDQ   295
Helicobacter      NLDLGYPFMDMTTRDKDEEAYWDMLLMQSCQHGIIANSTYSWWAAYLIENPEKIIGPKH    271
                   . :. : :  ::  :.: :::* .    :  ::**    *

Dictyostelium     LLYSNKSLNDEKYKENSLSLNFKSVHIGELFIS   328
Helicobacter      WLFGHENILCKEWVKIESHFEVKSQKYNA----   300
                   *:  . ::::  ** : .:*:   ::**  ::
```

METABOLICALLY ENGINEERED ORGANISMS FOR THE PRODUCTION OF ADDED VALUE BIO-PRODUCTS

RELATED APPLICATIONS

This application is a divisional of U.S. patent application Ser. No. 15/224,047, filed Jul. 29, 2016, now U.S. Pat. No. 10,570,430, which is a divisional of U.S. patent application Ser. No. 13/809,340, filed Jan. 9, 2013, now U.S. Pat. No. 9,701,992, which is a 35 U.S.C. § 371 filing of International Patent Application No. PCT/EP2011/061891, filed Jul. 12, 2011, which claims priority to European Patent Application No. 10169304.2, filed Jul. 12, 2010, the entire disclosures of which are hereby incorporated herein by reference.

TECHNICAL FIELD OF INVENTION

The present invention relates to genetically engineered organisms, especially microorganisms such as bacteria and yeasts, for the production of added value bio-products such as specialty saccharides, glycolipids and glycoproteins. More specifically, the present invention relates to host cells that are metabolically engineered so that they can produce said valuable specialty products in large quantities and at a high rate by bypassing classical technical problems that occur in biocatalytical or fermentative production processes.

BACKGROUND ART

The increasing cost of petroleum resources contributes to a growing awareness of the potential of biological production processes. This has intensified the research efforts of companies and research centres towards the development of economically viable and environmentally benign technologies for the production of an increasing number of bio-products, e.g., bio-fuels, bio-chemicals and bio-polymers. These are easily degradable and produced with minimal energy requirements and waste streams. In spite of the favourable context for production processes based on industrial biotechnology, the development of alternatives for well-established chemical synthesis routes often is too time intensive and too expensive to be economically viable. Consequently, there is a clear demand for a faster and cheaper development of new production strains.

Nowadays oligosaccharides are typically synthesized via bioconversion processes. Isolated and purified enzymes (so called in vitro bioconversions) and whole cell biocatalysts are commonly used. In essence, they convert one or more precursors into a desired bio-product.

However, the application of the in vitro bioconversions is often hampered because the synthesis of the product may require multiple enzymatic steps or because additional cofactors are required (NADH, NADPH, UTP, . . . ), which are expensive.

Another drawback of in vitro synthesis is the fact that the expression and purification of many enzymes is laborious and their purification process may result in a decreased enzymatic activity. Furthermore, each enzyme in such a multi-enzyme bioconversion process has its own optimal process parameters, resulting in very complicated optimization schemes. In such a process, the reaction equilibria also play an important role. For instance, when using a phosphorylase, a set substrate/product ratio that limits product yield will be at hand. This leads to complicated downstream processing schemes to separate the product from the substrate (33, 35).

Metabolic engineering is another approach to optimize the production of value added bio-products such as specialty carbohydrates. Commonly, whole cells have been metabolically engineered to produce added value bio-products starting from a supplied precursor. In this context, the cells are engineered as such that all the metabolic pathways involved in the degradation of the precursor(s) are eliminated (3, 45, 70, 77, 100). By doing so, the precursor(s) is (are) efficiently and directly converted into the desired product.

A major drawback of the latter approach is the fact that the biomass synthesis and the envisaged bio-product biosynthesis require different starting metabolites. For example, E. coli was metabolically engineered for the efficient production of 2-deoxy-scyllo-inosose starting from glucose. This strategy renders the metabolically engineered E. coli unfit to grow on glucose, requiring the addition of other substrates, e.g., glycerol to allow for biomass synthesis (45).

A second drawback of whole cell production systems is that there is a need for two phases, a growth phase, in which biomass is formed (or biomass synthesis), followed by a production phase of the envisaged product. This means that the growth phase and the production phase are separated in the time (consecutive phases). This results in very low overall production rates of the desired product(s). In addition, this type of process is hard to optimize. Indeed, fermentation processes have been developed making use of metabolically engineered cells which over-express production pathway genes. A large amount of the substrate is converted into biomass, resulting in only a minor flux of the substrate towards the product (13).

The present invention overcomes the above-described disadvantages as it provides metabolically engineered organisms which are capable to produce desired products with a high productivity and a guaranteed high yield (FIG. 1). This is accomplished by clearly splitting the metabolism of the organism in two parts: 1) a so-called 'production part' or 'production pathway', and 2) a 'biomass and cofactor supplementation' part or 'biomass and/or bio-catalytic enzyme formation pathway'. Said two parts are created by splitting a sugar into: a) an activated saccharide, and b) a (non-activated) saccharide. Each of said saccharides a) or b) are—or can be—the first precursors of either the production pathway a) or biomass and/or bio-catalytic enzyme formation pathways b), allowing a pull/push mechanism in the cell.

Indeed, biomass synthesis, which is the main goal of the cell, converts the activated saccharide or the saccharide into biomass and shifts the equilibrium of the reaction that splits the sugar towards the activated saccharide and saccharide. In this way, the life maintaining drive of the cell acts as a pulling mechanism for the product pathway. This pulling effect is created by biomass synthesis as it ensures the accumulation of the first substrate molecule of the production pathway, which, as such and in turn, also pushes the production pathway. This strategy solves the production rate problem which occurs in the two phase production strategies as described in the prior art. Moreover, by catabolising one part of the sugar moiety, the cell is always supplied with the necessary cofactors and the needed energy requirements for production of the specialty bio-product. The current strategy thus solves also the problem of co-factor supplementation that is needed in biocatalytic production as described in the prior art. In addition, the necessary enzymes in the production pathway are always synthesized efficiently and easily maintained via the engineering strategy of the current invention.

In addition, the present invention discloses the usage of a 2-fucosyltransferase originating from *Dictyostellium discoideum* to produce 2-fucosyllactose by the metabolically engineered organisms of the present invention.

BRIEF DESCRIPTION OF FIGURES

FIG. 9: Cellobiose production and yield of ΔpgmΔlacZΔglgCΔagp (4KO) P22-BaSP-CuCP. High phosphate indicates a phosphate concentration of 0.2 M phosphate, low phosphate indicates a concentration of 13 mM phosphate.

FIG. 10A shows the optimal route towards product and biomass and the needed knock outs to achieve this with a sucrose phosphorylase. FIG. 10 B shows the optimal route with an invertase combined with glucokinase.

FIG. 11: The sequence shown (SEQ ID NO: 51) is the partial genome sequence of wild type chromosome at the location of the pgm gene. The pgm gene sequence is marked in bold/italic.

FIG. 12: The sequence shown (SEQ ID NO: 52) is the partial genome sequence of a mutant strain in which only a scar remains at the location of the pgm gene. The scar sequence is marked in bold/italic.

FIG. 13: The sequence shown (SEQ ID NO: 53) is the partial genome sequence of a pgm mutant strain in which the pgm gene is replaced with a part of a GFP protein sequence. The newly introduced sequence is marked in bold/italic.

FIG. 14: The sequence shown (SEQ ID NO: 54) is the partial genome sequence of a pgm mutant strain in which the pgm gene is replaced with kanamycine cassette. The newly introduced sequence is marked in bold/italic.

FIG. 19: Alignment of *Dictyostelium discoideum* and *Helicobacter pylori* fucosyltransferase, the amino acids marked in colour are conserved motives found in the 2-fucosyltransferases of GT family 11. Bold indicates motif 1, underlined, motif 2, and italic, motif 3 (67). The depicted *Dictyostelium discoideum* sequence shown corresponds with SEQ ID NO: 55. The depicted *Helicobacter pylori* sequence shown corresponds with SEQ ID NO: 56.

DESCRIPTION OF INVENTION

Figure 1:
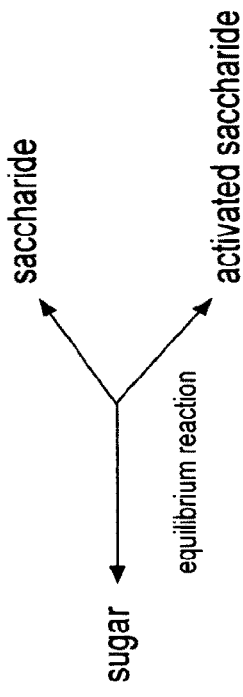
FIG. 1: (a) A normal equilibrium reaction, which occurs in the current production technologies (b) pull/push principle: the equilibrium is shifted towards the saccharide and activated saccharide. The main goal of a cell is to grow, hence it pulls at the saccharide (by means of example), to form biomass ("biomass and/or bio-catalytic enzyme formation pathway") and supplements the necessary co-factors for the production pathway next to life maintenance. Due to this pulling effect, the activated saccharide will accumulate in the cell and pushes the production pathway.

The present invention discloses metabolically engineered organisms, especially microorganisms, which are capable to produce added value bio-products with a high productivity and a guaranteed high yield. The organisms of the present invention are metabolically engineered so that two distinct routes are constructed leading to product and to growth/biomass. This is achieved by reducing or eliminating the activity of enzymes catalyzing reactions converting metabolites from the 'biomass and/or bio-catalytic enzyme and/or cofactor supplementation part' into metabolites from the 'production pathway' part and vice versa, e.g. by reducing or eliminating/knocking-out at least one, some or all the genes encoding for enzymes performing reactions which convert the production pathway intermediates into biomass precursors, and/or reducing or eliminating/knocking out at least one, some or all the genes coding for enzymes performing the reactions which degrade the production pathway intermediates. Moreover, these metabolic/genetic changes do not impair the growth of the engineered cells. For example: carbohydrate hydrolases in combination with carbohydrate kinases, carbohydrate synthases, and, carbohydrate phosphorylases can be introduced into the cell. The latter enzymes convert the substrates comprising a saccharide, an oligosaccharide, a polysaccharide or a mixture thereof in a sugar moiety and an activated sugar moiety (e.g. a phosphorylated saccharide moiety, UDP, CMP, GDP, ADP, TDP or dTDP . . . activated sugar moiety). Additional metabolic engineering of the cell involves blocking of the pathway starting from the activated sugar moiety towards the biomass constituents. In this way, the (non-activated) sugar moiety is used as 'fuel' (or energy-source) and building block for the synthesis of biomass, of the numerous bio-catalytic enzymes that will perform the conversion of the activated sugar moiety to the desired product (=e.g. a specialty carbohydrate) and of the necessary cofactors (NADH, ATP, UTP . . . ). Conversely, the activated sugar moiety can also be used as 'fuel', while the sugar moiety is activated by a carbohydrate kinase and 'pushed' into the production route of the desired specialty product.

Using the engineered organisms of the present invention, product formation through the conversion of the activated sugar can be linked to growth which is fueled by the other sugar moiety (or vice versa). In this way, the cell's natural drive for multiplication is used as an asset to push the production of the desired bio-product. This means that the former drawback of having to produce biomass before the actual production of the bio-product can start, is now turned into a benefit. This methodology results in high production rates, without the inherent problems that come with multi-enzymes systems and two phase fermentation systems. In addition, the organisms of the present invention may use the same substrate(s) as indicated above for both growth or biomass production and production of the desired product at a high rate, the overall principle behind this metabolic engineering strategy is thus a pull/push principle as is also explained above. The central carbon metabolism that leads to biomass and cofactors pulls at one part of the sugar moiety for growth while the other part accumulates in the cell, pushing the production pathway.

The latter approach cannot only be used to produce desired specialty carbohydrates or activated carbohydrates but can also be applied for the synthesis of a wide variety of glycosylated compounds, e.g., saccharides, nucleosides, glycosylphosphates, glycoproteins and glycolipids.

Multiple starting enzymes can be introduced into a cell to split the metabolism into two parts, in combination with gene knock outs. Non-limiting examples of enzymes that can be used to split sugars into an activated saccharide and a saccharide are sucrose phosphorylases, sucrose synthases, sucrases (invertases) combined with a glucokinase and/or fructokinase, a trehalase combined with a glucokinase, a maltase combined with a glucokinase, a sucrose-6-phosphate hydrolase combined with a fructokinase, a maltose phosphorylase, a maltose synthase, a amylase combined with a phosphorylase or synthase or hydrolase, a lactose synthase, a lactose phosphorylase, a lactase (or beta-galactosidase) combined with a galactokinase and/or a glucokinase.

The present invention relates to a metabolically engineered organism for the production of at least one specialty product chosen from the group consisting of a saccharide, an activated saccharide, a nucleoside, a glycoside, a glycolipid and a glycoprotein, characterized in that:

a) said organism is genetically modified with the introduction of at least: i) a gene encoding for a carbohydrate hydrolase in combination with a gene encoding for a carbohydrate kinase, ii) a gene encoding for a carbohydrate synthase, or, iii) a gene encoding for a carbohydrate phosphorylase, so that said organism is capable to split a disaccharide, oligosaccharide, polysaccharide or a mixture thereof into an activated saccharide and a saccharide, and b) said organism is further genetically modified so that at least one other gene than any of the introduced genes of step a) of said organism is rendered less-functional or non-functional and wherein said other gene encodes for an enzyme which converts said activated saccharide into biomass and/or bio-catalytic enzymes.

The term 'saccharide' relates to monosaccharides such as, but not limited to, aldoses, ketoses, pentoses, methylpentoses, hexoses, polyols with or without either carbonyl, carboxyl, amino groups or in which a hydroxylgroup is replaced by, but not limited to a hydrogen, amino, thiol, phosphate and/or similar group or a derivative of these groups. The term 'saccharide' also relates to di-, oligo-, and polysaccharide which are made up of one or more monosaccharides as described above, linked to each other by a glycosidic bond.

The term 'nucleoside' relates to each monosaccharide that is substituted with a nucleotide which is for instance, but not limited to, UDP, GDP, ADP, TDP, CMP, or dTDP.

The term 'glycoside' relates to a saccharide which forms a glycosidic bond with other chemical compounds, such as, but not limited to sterols, phenols, fatty acids, phosphatidylinositols, vitamine C, cartenoides and artimisinine.

The term 'glycolipid' relates to a saccharide which forms a glycosidic bond with a fatty acid or lipid.

The term 'glycoprotein' relates to a saccharide which forms a glycosidic bond with a protein.

The term 'glycosylphosphate' relates to a phosphorylated saccharide.

The present invention further relates to an organism as indicated above wherein said organism is further genetically modified with the introduction of at least one other gene which converts said activated saccharide into a specialty product, or, wherein at least one other endogenous gene of said organism which converts said activated saccharide into a specialty product is over-expressed.

In addition, the present invention relates to an organism as indicated above wherein said organism is capable to grow on a disaccharide, oligosaccharide, polysaccharide or a mixture thereof as the main carbon source. With the term 'main' is meant the most important carbon source for biomass formation, i.e. 75, 80, 85, 90, 95, 98, 99% of all the required carbon is derived from the above-indicated carbon source. In one embodiment of the invention, said carbon source is the sole carbon source for said organism, i.e. 100% of all the required carbon is derived from the above-indicated carbon source.

The term 'metabolic engineering' refers to the practice of optimizing genetic and regulatory processes within said organism to increase the organism's production of a certain desired substance or product. The latter product is hereby denominated as a 'specialty product' and specifically relates to a desired saccharide (activated or non-activated), a nucleoside, a glycoside, a glycolipid or a glycoprotein. Some non-limiting examples of such products are sugar derivates such as 1,2-fucosyllactose, 1,3-fucosyllactose, 1,4-fucosyllactose, 1,6-fucosyllactose, galactinol, stachyose, globotriose, galactose(beta1-4)rhamnose, sophorose, cellobiose, UDP-glucose, sophorolipids, myo-inositol, L-arabinose, scyllo-inosose, glycosylphosphatidylinositol, lacto-N-biose, lacto-N-tetraose, lactosamine, fucosylated galactosyloligosaccharides, L-fucose, N—Ac glucosamine, sialic acid, sialyllactose, chitosan and chitin.

The term 'engineering' relates to any well-known technique which can be used to genetically modify an organism as is for example described in (9, 17, 19, 21, 22, 42).

The terms 'an organism being capable to grow on a disaccharide, oligosaccharide, polysaccharide or a mixture thereof as the main carbon source' means that organisms of the present invention may use the same disaccharide, oligosaccharide, polysaccharide or a mixture thereof for both growth (or biomass production) and production of the desired product, and, that they can use the latter saccharides as the only carbon source in order to multiply and/or to be metabolically active. In short, the organisms of the present invention are capable to multiply and metabolize in or on a medium comprising said saccharides as the only carbon source.

With the terms 'splitting (or conversion) into an activated saccharide and a saccharide' is meant that the latter saccharides which are used as carbon source will be split (or converted) by the organism of the present invention into an activated sugar moiety—some non-limiting examples of activated sugar moieties are sugars moieties bearing a phosphate, UDP, GDP, ADP, TDP or dTDP group—and a non-activated sugar moiety which does not bear or is not bound to the latter groups.

The terms 'biocatalytic enzymes' refers to all enzymes needed for the production of the specialty carbohydrate.

The term 'biomass' refers to all cellular components (i.e. proteins, DNA, RNA, phosphatidylserine, phosphatidylethanolamine, cardiolipin, phosphatidylglycerol, putrescine, spermidine, peptidoglycan, glycogen and/or lipopolysaccharide (63) that can be synthesized in the modified specialty carbohydrate production strain from the sugar moiety that is not used in the specialty carbohydrate (and other added value products) production route.

The terms 'genes which are rendered less-functional or non-functional' refer to the well-known technologies for a skilled person (such as the usage of siRNA, RNAi, miRNA, asRNA, mutating genes, knocking-out genes, transposon mutagenesis, . . . ) which are used to change the genes in such a way that they are less-able (i.e. statistically significantly 'less-able' compared to a functional wild-type gene) or completely unable (such as knocked-out genes) to produce functional final products (2, 4, 5, 7, 8, 14, 19, 37, 40, 47, 73, 79, 80, 85, 93, 98).

The term '(gene) knockout' thus refers to a gene which is rendered non-functional.

The term 'polysaccharide' refers to a saccharide which contains 6 or more monosaccharide subunits.

The present invention further relates to a metabolically engineered organism as indicated above wherein the genetic modification of step a) is optional, or, is replaced by overexpressing at least: i) an endogenous gene encoding for a carbohydrate hydrolase in combination with an endogenous or heterologous gene encoding for carbohydrate kinase, ii) an endogenous gene encoding for a carbohydrate synthase, or, iii) an endogenous gene encoding for a carbohydrate phosphorylase, and wherein said organism is capable to split a disaccharide, oligosaccharide, polysaccharide or a mixture thereof into an activated saccharide and a saccharide.

A preferred carbohydrate hydrolase of the present invention is a lactase, invertase, sucrase, trehalase, sucrose-6-phosphate hydrolase, maltase or amylase. A preferred carbohydrate kinase of the present invention is galactokinase, a fructokinase, a glucokinase or a mannokinase.

The present invention further relates to a metabolically engineered organism as indicated above wherein said activated saccharide in step b) is replaced by said saccharide. Hence, the 'activated sugar moiety' in this embodiment is used as 'fuel', whereas the 'sugar moiety' is activated by a kinase and is pushed into the production route of the desired specialty product.

The present invention also relates to a metabolically engineered organism as indicated above wherein said gene in step a) splits a disaccharide, oligosaccharide, or polysaccharide in two similar or different activated saccharides or in two similar or different saccharides.

The term 'organism' as indicated above refers to a microorganism chosen from the list consisting of a bacterium, a yeast or a fungus cell, or, refers to a plant or animal cell. The latter bacterium preferably belongs to the species *Escherichia coli*. The latter yeast preferably belongs to the species *Saccharomyces cereviseae*.

More specifically, the present invention relates to a metabolically engineered organism as indicated above, wherein said activated saccharide is selected from the group consisting of alpha glucose-1-phosphate, alpha galactose-1-phosphate, beta glucose-1-phospate, beta galactose-1-phosphate, fructose-6-phosphate, glucose-6-phosphate, UDP-glucose and UDP-galactose and wherein said saccharide is selected from the group consisting of fructose, glucose and/or galactose.

The present invention further relates, as indicated above, to a metabolically engineered organism as indicated above, wherein said carbohydrate hydrolase is a lactase, invertase, sucrase, maltase, trehalase, sucrose-6-phosphate hydrolase and/or amylase, and, wherein said carbohydrate kinase is a galactokinase, a fructokinase, a glucokinase and/or mannokinase.

Even more specifically, the present invention relates to a metabolically engineered organism as indicated above wherein:
    said gene in step a) is encoding for a sucrose phosphorylase, and/or
    the following genes in step b) are rendered non-functional: a gene encoding for a beta-galactosidase, and/or, a gene encoding for a phosphoglucomutase, and/or, a gene encoding for a glucose-1-phosphate adenylyltransferase, and/or, a gene encoding for a phosphatase (such as but not limited to a glucose-1-phosphatase) and/or, a gene encoding for a glucose-1-phosphate uridyltransferase, and/or, a gene encoding for a UDP-glucose-4-epimerase, and/or, a gene encoding for UDP-glucose:galactose-1-phosphate uridyltransferase, and/or, a gene encoding for UDP-galactopyranose mutase, and/or, a gene encoding for UDP-galactose: (glucosyl)lipopolysaccharide-1,6-galactosyltransferase, and/or, a gene encoding for a UDP-galactosyltransferase, and/or, a gene encoding for a UDP-glucosyltransferase, and/or, a gene encoding for an UDP-glucuronate transferase, and/or, a gene encoding for an UDP-glucose lipid carrier transferase, and/or, a gene encoding for an UDP-sugar hydrolase, and/or, a gene encoding for an invertase, and/or, a gene encoding for a maltase, and/or, and/or a gene encoding for a trehalase, and/or, a gene encoding for a sugar transporting phosphotransferase, and/or, a gene encoding for a hexokinase.

An example of the latter metabolically engineered organism is an organism wherein:
  said gene in step a) is the gene encoding for a sucrose phosphorylase possibly (but not solely) originating from a Lactic acid bacterium such as *Bifidobacterium adolescentis, Leuconostoc mesenteroides, Lactobacillus acidophilus*, and/or *Streptococcus mutans*, and/or
  said genes in step b) are: gene lacZ, the gene pgm, the gene ycjU, the gene glgC, the gene agp, the gene ptsG, the gene glk, the gene glf, the gene waaB, the gene ushA, the gene wcaA, the gene wcaC, the gene wcaE, the gene wcaI, the gene wcaL, the gene wcaJ, the gene galU, the gene galF, the gene galE, the gene malP, the gene malQ, and/or, the gene galT (20, 25, 27, 28, 32, 46, 48, 49, 52, 54, 62, 82, 86, 87, 96, 97).

Another example of a metabolically engineered organism as indicated above is an organism wherein:
  said gene in step a) is encoding for a sucrose phosphorylase possibly (but not solely) originating from a Lactic acid bacterium such as *Bifidobacterium* adolescentis, *Leuconostoc mesenteroides, Lactobacillus acidophilus*, and/or *Streptococcus mutans*, and/or
  said genes in step b) are: the gene PGM1, the gene PGM2, the gene GLG1, the gene GLG2, the gene INM1, the gene INM2, the gene GLK1, the gene HXK1, the gene HXK2, the gene GAL10, the gene GAL7, the gene YHL012W, the gene UGP1, the gene GSY1, the gene GSY2, the gene DIE2, the gene ALG8, the gene ATG26, the gene SUC2, the gene MAL32, the gene MAL12, the gene YJL216C, and/or, the gene YGR287C, and/or, FEN1, and/or, FKS1, and/or, GSC2, and/or, TPS1 (10, 12, 15, 16, 18, 24, 30, 31, 36, 41, 51, 56, 57, 59, 61, 66, 76, 81, 84, 89-91, 99).

The latter engineered organisms can, for example but not limited to, be used to produce cellobiose, kojibiose, threhalose, L-arabinose, myo-inositol, raffinose, stachyose, L-rhamnose or L-ribose as a specialty product.

A further aspect of the present invention relates to a metabolically engineered organism as indicated above wherein said sucrose phosphorylase of step a) is replaced by a sucrose synthase, a maltose phosphorylase or a maltose synthase, or, wherein said sucrose phosphorylase of step a) is replaced by a lactose phosphorylase or a lactose synthase.

The latter organisms can, for example but not limited to, be used to produce sophorose, UPD-glucose, glycolipids, flavone 3-O-β-D-glucoside (sucrose synthase in step a), galactose(beta1-4)rhamnose (lactose phosphorylase in step a), or, UDP-galactose, galactinol, stachyose or globotriose, psychosine (lactose synthase in step a) as specialty products.

The present invention further relates to a metabolically engineered organism as indicated above wherein said activated saccharide in step b) is replaced by said saccharide and wherein:
  said gene is step a) is encoding for a sucrose phosphorylase, and/or
  the following genes in step b) are rendered non-functional: a gene encoding for a beta-galactosidase, and/or, a gene encoding for a glucose-6-phosphate isomerase, and/or, a gene encoding for a glucose-1-phosphate adenylyltransferase, and/or, a gene encoding for a phosphatase (for example, glucose-1-phosphatase), and/or, a gene encoding for a phosphofructokinase A, and/or, a gene encoding for a phosphofructokinase B, and/or, a gene encoding for phosphogluconate dehydratase, and/or, a gene encoding for 2-keto-3-deoxygluconate-6-phosphate aldolase, and/or, a gene encoding for a glucose-1-phosphate uridylyltransferase, and/or, a gene encoding for an UDP-glucose-4-epimerase, and/or, a gene encoding for an UDP-glucose:galactose-1-phosphate uridyltransferase, and/or, a gene encoding for an UDP-galactopyranose mutase, and/or, a gene encoding for an UDP-galactose: (glucosyl)lipopolysaccharide-1,6-galactosyltransferase, and/or, a gene encoding for an UDP-galactosyltransferase, and/or, a gene encoding for an UDP-glycosyltransferase, and/or, a gene encoding for an UDP-glucuronate transferase, and/or, a gene encoding for an UDP-glucose lipid carrier transferase, and/or, a gene encoding for GDP-mannose hydrolase, and/or, a gene encoding for an UDP-sugar hydrolase, and/or, a gene encoding for a mannose-6-phosphate isomerase, and/or, a gene encoding for an UDP-N-acetylglucosamine enoylpyruvoyl transferase, and/or, a gene encoding for an UDP-N acetylglucosamine acetyltransferase, and/or, a gene encoding for an UDP-N-acetylglucosamine-2-epimerase, and/or, a gene encoding for an undecaprenyl-phosphate-alfa-N-acetylglucosaminyl transferase, and/or, glucose-6-phosphate-1-dehydrogenase, and/or, a gene encoding for a L-glutamine:D-fructose-6-phosphate aminotransferase, and/or, a gene encoding for a mannose-6-phosphate isomerase, and/or a gene encoding for a sorbitol-6-phosphate dehydrogenase, and/or, a gene encoding for a mannitol-1-phosphate 5-dehydrogenase, and/or a gene encoding for a allulose-6-phosphate 3-epimerase, and/or, a gene encoding for an invertase, and/or, a gene encoding for a maltase, and/or, and/or a gene encoding for a trehalase, and/or, a gene encoding for a sugar transporting phosphotransferase, and/or, a gene encoding for a hexokinase.

More specifically, the present invention relates to a metabolically engineered organism as indicated above wherein:
  said gene in step a) is the sucrose phosphorylase originating from a Lactic acid bacterium such as *Bifidobacterium adolescentis, Leuconostoc mesenteroides, Lactobacillus acidophilus*, or *Streptococcus mutans*, and/or
  said genes in step b) are: the gene lacZ, the gene pgi, the gene glgC, the gene agp, the gene pfkA, the gene pfkB, the gene waaB, the gene ushA, the gene eda, the gene edd, the gene wcaA, the gene wcaC, the gene wcaE, the gene wcaI, the gene wcaL, the gene wcaJ, the gene wcaB, the gene wcaF, the gene wcaK, the gene wcaD, the gene galU, the gene galF, the gene galE, the gene gmm, the gene galT, the gene manA, the gene murA, the gene lpxA, the gene rffE, and/or, the gene rfe, the gene glmS, the gene srlD, the gene mtlD, the gene alsE and/or, zwf (6, 20, 25, 28, 29, 32, 43, 44, 46, 49, 52-55, 62, 65, 75, 78, 82, 86, 87, 96, 97, 101).

Another metabolically engineered organism according to the present invention is an organism wherein:
  said gene in step a) is a gene encoding for a sucrose phosphorylase originating from a Lactic acid bacterium such as *Bifidobacterium* adolescentis, *Leuconostoc mesenteroides, Lactobacillus acidophilus*, or *Streptococcus mutans*, and/or
  said genes in step b) are: the gene PGI1, the gene PFK1, the gene PFK2, the gene PFK26, the gene PFK26, the gene PFK27, the gene GND1, the gene GND2, the gene PM140, the gene ZWF1, the gene GFA1, the gene GLG1, the gene GLG2, the gene INM1, the gene INM2, the gene GLK1, the gene HXK1, the gene HXK2, the gene GAL10, the gene GAL7, the gene YHL012W, the gene UGP1, the gene GSY1, the gene GSY2, the gene DIE2, the gene ALG8, the gene ATG26, the gene SUC2, the gene MAL32, the gene MAL12, the gene YJL216C, and/or, the gene YGR287C, and/or, FEN1, and/or, FKS1, and/or, GSC2, and/or, TPS1 (12, 15, 16, 24, 26, 30, 31, 34, 36, 38, 39, 41, 51, 56, 57, 59-61, 64, 66, 74, 76, 83, 84, 89, 90, 95, 99).

The latter engineered organism can, for example, be used to produce fucosylated sugar derivates such as fucosyllactose, and more specifically α-1,2-fucosyllactose, α-1,3-fucosyllactose, α-1,4-fucosyllactose, α-1,6-fucosyllactose as specialty products with specific fucosyltransferases originating from for example but not limited to *Helicobacter pylori, Bacteroides* sp., *Homo sapiens, Mus musculus, Bos taurus* and, *Dictyostelium discoideum*. In addition, said engineered organism can be used to produce chitosans by a chitine synthase and chitine deacetylase or to produce myo-inositol by introducing inositol-1-phosphate synthase in combination with inositol monophosphatase.

Specific examples of genes which convert said activated saccharide into a specialty product are genes coding for an epimerase, a transferase, a reductase, a (pyro)phosphorylase, a (de)carboxylase, a dehydratase, a permease, a synthase and/or an isomerase. Therefore the present invention relates to a metabolically engineered organism as indicated above wherein the genes which convert said activated saccharide into a specialty product code for an epimerase, transferase, reductase, dehydrogenase, oxidase, pyrophosphorylase, (de)carboxylase, dehydratase, permease, synthase and/or isomerase. The present invention even more specifically relates to the latter metabolically engineered organisms wherein said epimerase is UDP-galactose-4-epimerase or UDP-N-acetylglucosamine epimerase, and/or, wherein said transferase is a glycosyltransferase, a sialyltransferase or a sulfotransferase.

The invention further relates to a metabolically engineered organism as indicated above wherein said specialty product is a monosaccharide, a disaccharide, a trisaccharide, a tetrasaccharide, a pentasaccharide, an oligosaccharide, a polysaccharide, a nucleoside, an O-glycoside, an S-glycoside, an N-glycoside, a C-glycoside, a glycoprotein, a glycolipid or an activated carbohydrate such as but not limited to myo-inositol, L-arabinose, Scyllo-inosose, Glycosylphosphatidylinositol, Lacto-N-biose, Lacto-N-tetraose, Lactosamine, Fucosylated galactosyloligosaccharides (GOS), L-Fucose N—Ac glucosamine, Sialic acid, Sialyllactose, chitosan, chitin, 1,2-fucosyllactose, 1,3-fucosyllactose, 1,4-fucosyllactose, 1,6-fucosyllactose, galactinol, stachyose, globotriose, galactose(beta1-4)rhamnose, sophorose, cellobiose, UDP-glucose and sophorolipids.

The present invention further relates to a method to produce a specialty product as described above comprising:
  i) metabolically engineering a microorganism as described above, and
  ii) cultivating said genetically engineered microorganism, and
  iii) extracting and purifying said specialty product.

It is clear that any methodology known in the art to cultivate micro-organisms, and, to extract and purify specialty products from said cultivation can be employed in the present invention.

In addition, the present invention relates to the usage of a 2-fucosyltransferase originating from *Dictyostelium discoideum* and having an amino acid sequence given by SEQ ID NO: 1, or, a fragment thereof having 2-fucosyltransferase activity, or, a variant thereof having a sequence identity of at least 75% and having 2-fucosyltransferase activity to produce 2-fucosyllactose (α1,2-fucosyllactose). A specific fragment having 2-fucosyltransferase activity as indicated above is given by SEQ ID NO: 4.

Also the usage of a nucleic acid encoding for a 2-fucosyltransferase as indicated above, and specifically wherein said nucleic acid is given by SEQ ID NO: 2 or SEQ ID NO: 3 (which both encode for SEQ ID NO: 1), to produce fucosyllactose is part of present invention. Nucleic acids encoding for SEQ ID NO: 4 are given by SEQ ID NO: 5 and SEQ ID NO: 6 and are also part of the present invention.

The term 'fragment' refers to a protein (or peptide or polypeptide) containing fewer amino acids than the amino acid sequence as depicted by SEQ ID NO: 1 and that retains said 2-fucosyltransferase activity. Such fragment can—for example—be a protein with a deletion of 10% or less of the total number of amino acids at the C- and/or N-terminus or can correspond to SEQ ID NO: 4. The term "variant" refers to a protein having at least 75% sequence identity, preferably having at least 76-85% sequence identity, more preferably having at least 86-90% sequence identity or most preferably having at least 91, 92, 93, 94, 95, 96, 97, 98 or 99% sequence identity with SEQ ID NO: 1 or with a fragment thereof, and, that encodes for a protein retaining said 2-fucosyltransferase activity.

Hence, orthologues, or genes in other genera and species (than *Dictyostellium discoideum* the from which SEQ ID NO: 1 is derived) with at least 75% identity at amino acid level, and having the described function are part of the present invention. The percentage of amino acid sequence identity is determined by alignment of the two sequences and identification of the number of positions with identical amino acids divided by the number of amino acids in the shorter of the sequences×100. The latter 'variant' may also differ from the protein as depicted by SEQ ID NO: 1 only in conservative substitutions and/or modifications, such that the ability of the protein to have 2-fucosyltransferase activity is retained. A "conservative substitution" is one in which an amino acid is substituted for another amino acid that has similar properties, such that one skilled in the art of protein chemistry would expect the nature of the protein to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also (or alternatively) be proteins as described herein modified by, for example, by the deletion or addition of amino acids that have minimal influence on the 2-fucosyltransferase activity as defined above, secondary structure and hydropathic nature of the enzyme.

The following specific sequences, as indicated above, are part of the present invention:

SEQ ID NO: 1: the complete amino acid sequence of the
2-fucosyltransferase of *Dictyostellium discoideum*:
MNDSPIISVVLPFLIKDNDDKSLNYQGINNLIISIDSIIEQTEKEWELILVDDGSNNEILEQLLSKRYS

TDNRIKFIINKENKGIVKSLNDAILNHCSPTSKYIARMDSDDISHPTRLQSQLKYLQSNETIDILGCPI

KMENNNKLIEILNNNNNNNNNINNNVKELINIINNEESFKFIQHPDKDILMWSMFFNCCIVHPSVIFKRS

IFTIEHCYEENNQFPFIEDYLFWLKSLIMKGLNISNIQSSTPLLYLRKHNNSISFKNIEKQKDSTANAS

CYYLNILFKRFNIDSEIIQNSSLSMKEIIQFFQLSPSSLSKINNISIELFEFAFKYLELIEKSCTKQQP

NYSNSIKDAANEKMGELVSLCLSNYPNNQKSSLLWEKWLSRNPTSQLLSLLSNLNVKSSTTIINNNINN

NNNNNNNNNNNNNNNNNNNNNNNNNSILNFISGINSNKINTPKSNNNKFKENGIRIICFSKDRAFQLK

EYLRTFFKYLKNDDNGNDKFEIIVDVLFTYSNEKFKNSYQLVIESFPQVNFIKEENFTDQLINLVQKTN

KLEYVMFSVDDILYYNEFNLKEYCLSLNSEPLALGFYMKLNKNITYCHTCNQDITIPLNSNTISRTENN

FKYLKWNRNDNDCKKDWNYPWDLCSTIYRCNDIDSIINGIVKYYGIRNGINHPNRFEENGNRPIIQKQI

YQNKPYCLCLSDHYSPMSVVTINRVQDVYDNPIYDQTLSLDDLDQLLYSNKSLNDEKYKENSLSLNFKS

VHIGELFIS

SEQ ID NO: 2: the codon optimized nucleotide sequence encoding SEQ ID
NO: 1 for expression in E. Coli:
ATGAACGATAGCCCGATTATTAGCGTTGTTCTGCCGTTTCTGATCAAAGATAACGATGATAAAAGCCTG

AACTACCAGGGCATTAACAACCTGATTATTAGCATCGATAGCATCATCGAGCAGACCTTTAAAGAATGG

GAACTGATTCTGGTTGATGATGGCAGCAATAACGAAATTCTGGAACAGCTGCTGAGCAAACGTTATAGC

ACCGATAACCGCATCAAATTTATTATTAATAAAGAAAATAAAGGCATTGTGAAAAGCCTGAATGATGCC

ATTCTGAATCATTGTAGCCCGACCAGCAAATATATTGCACGTATGGATAGCGACGATATTAGCCATCCG

ACCCGTCTGCAGAGCCAGCTGAAATATCTGCAGAGCAATGAAACCATTGATATTCTGGGTTGCCCGATC

AAAATGTTTAATAATAATAAACTGATTGAAATTCTGAATAATAATAACAATAACAACAATATTAATAAT

AATGTGAAAGAACTGATTAATATTATTAATAATGAAGAAAGCTTTAAATTTATTCAGCATCCGGATAAA

GATATTCTGATGTGGTCCATGTTCTTCAATTGCTGTATTGTTCATCCGAGCGTGATTTTTAAACGCAGC

ATTTTTTACCATCGAGCACTGCTATGAAGAGAATAATCAGTTTCCGTTCATCGAGGATTACCTGTTTTGG

CTGAAATCCCTGATTATGAAAGGCCTGAACATTAGCAATATCCAGAGCAGCACACCGCTGCTGTATCTG

CGTAAACATAATAACAGCATTAGCTTTAAAAATATTGAAAAACAGAAAGATAGCACCGCCAATGCCAGC

TGTTATTATCTGAACATTCTGTTCAAACGCTTTAACATCGACAGCGAAATTATTCAGAATAGCAGCCTG

AGCATGAAAGAAATCATCCAGTTTTTTCAGCTGAGCCCGAGCAGCCTGTCCAAAATTAATAACATTAGC

ATCGAACTGTTTGAATTTGCCTTTAAATATCTGGAACTGATCGAGAAAAGCTGTACCAAACAGCAGCCG

AATTATAGCAACAGCATTAAAGATGCAGCCAACGAAAAAATGGGTGAACTGGTTAGCCTGTGTCTGAGC

AATTATCCGAATAATCAGAAAAGCAGTCTGCTGTGGGAAAAATGGCTGAGCCGTAATCCGACCAGCCAG

CTGCTGAGTCTGCTGAGCAATCTGAATGTTAAAAGCAGCACCACCATTATTAATAACAATATTAACAAC

AACAATAATAATAACAACAATAATAACAATAACAATAACAATAATAACAACAACAACAATAATAATAAT

AACAACAACAGCATTCTGAATTTTATTAGCGGCATTAATAGCAATAAAATTAATACCCCGAAAAGCAAC

AATAACAAATTTAAAGAGAATGGCATTCGCATTATTTGCTTCAGCAAAGATCGTGCATTCCAGCTGAAA

GAATATCTGCGCACCTTCTTCAAATATCTGAAAAATGATGATAATGGCAATGATAAATTTGAAATTATT

GTGGATGTGCTGTTTACCTATAGCAATGAAAAATTCAAAAATAGCTATCAGCTGGTGATCGAAAGCTTT

CCGCAGGTTAACTTTATTAAAGAAGAAAACTTTACCGATCAGCTGATTAACCTGGTGCAGAAAACCAAC

AAACTGGAATATGTGATGTTCAGCGTGGATGATATCCTGTATTACAACGAGTTCAATCTGAAAGAGTAT

TGCCTGAGCCTGAATAGCGAACCGCTGGCACTGGGTTTTTATATGAAACTGAATAAAAATATTACCTAT

TGCCATACCTGCAACCAGGATATTACCATTCCGCTGAATAGCAATACCATTAGCCGCACCGAAAATAAC

TTTAAATACCTGAAATGGAATCGCAACGATAATGATTGCAAAAAAGACTGGAACTATCCGTGGGATCTG

TGTAGCACCATTTATCGTTGCAACGACATTGACAGCATCATTAATGGTATTGTGAAATATTATGGTATT

CGCAACGGCATTAATCATCCGAATCGCTTTGAATTTAATGGCAACCGTCCGATTATTCAGAAACAAATC

TACCAGAACAAACCGTATTGTCTGTGCCTGAGCGATCATTATTCACCGATGAGCGTTGTTACCATTAAT

-continued

```
CGTGTTCAGGATGTGTATGATAACCCGATTTATGATCAGACCCTGAGCCTGGATGATCTGGATCAACTG

CTGTATAGCAATAAATCCCTGAACGATGAAAATATAAAGAAAACAGCCTGAGTCTGAACTTCAAAAGC

GTTCATATTGGCGAACTGTTCATCAGCTAA
```

SEQ ID NO: 3: the native nucleotide sequence encoding SEQ ID NO: 1:
the 2-fucosyltransferase of Dictyostelium discoideum:

```
ATGAATGATTCACCAATAATAAGTGTAGTTTTACCTTTTTTAATAAAGGACAATGACGATAAATCATTA

AATTACCAAGGAATAAATAATTTAATAATATCAATAGATAGCATTATTGAACAAACTTTTAAAGAATGG

GAATTAATTTTAGTTGATGATGGATCAAATAATGAAATTTTGGAGCAATTACTTTCAAAAAGATATAGT

ACAGATAATAGAATTAAATTCATAATAAATAAAGAGAATAAAGGTATTGTTAAAAGTTTAAATGATGCA

ATTTTAAATCATTGTTCACCAACTTCAAAATATATTGCTCGTATGGATTCAGATGATATTTCTCATCCA

ACAAGATTACAATCTCAACTTAAATATCTTCAATCAAATGAAACAATTGATATATTAGGTTGTCCAATT

AAAATGTTTAATAATAATAAATTAATTGAAATTTTAAATAATAATAATAATAATAATAATATTAATAAT

AATGTGAAAGAGTTAATTAATATAATTAATAATGAAGAATCTTTTAAATTTATTCAACATCCTGATAAA

GATATTTTAATGTGGTCAATGTTTTTCAATTGTTGTATTGTTCACCCTTCTGTAATATTTAAAAGATCG

ATATTCACTATTGAACATTGTTATGAAGAAAACAACCAATTTCCATTCATTGAAGATTACTTATTTGG

TTAAAATCCTTAATAATGAAAGGTTTAAATATTTCAAATATCCAATCATCAACACCATTACTATATTTA

AGAAAACATAATAACTCTATATCTTTTAAAAATATTGAAAAACAAAAAGATTCCACTGCTAATGCATCT

TGTTATTATCTAAATATACTTTTTAAAAGATTTAATATTGATTCTGAAATTATTCAAAATTCTTCACTC

TCAATGAAAGAAATTATTCAGTTCTTTCAACTTTCACCATCATCTTTATCAAAAATCAATAATATTTCA

ATTGAATTATTTGAATTTGCATTTAAATATCTAGAATTAATTGAAAAATCATGTACAAAACAACAACCA

AACTATTCAAACAGTATAAAAGATGCAGCAAATGAAAAAATGGGTGAATTAGTATCTTTATGTTTATCA

AATTATCCAAATAATCAAAAATCATCATTACTTTGGGAAAAATGGTTATCAAGAAATCCAACCTCACAA

TTACTATCACTTTTATCAAATTTAAATGTAAAATCTTCAACTACTATAATTAATAATAATATTAATAAT

AATAATAATAATAATAATAATAATAATAATAATAATAATAATAATAATAATAATAATAATAATAATAAT

AATAATAATTCAATTTTAAATTTTATATCTGGCATTAATAGTAATAAAATAAATACTCCAAAATCTAAT

AATAATAAATTTAAAGAAAATGGAATTAGAATAATTTGTTTCTCAAAAGATAGAGCATTTCAATTAAAA

GAATATCTTAGAACATTTTTTAAATATTTAAAAAATGATGATAATGGAAATGATAAATTTGAAATTATT

GTTGATGTATTATTTACATATTCAAATGAGAAATTCAAAAACTCTTATCAATTAGTTATTGAAAGTTTT

CCACAAGTTAATTTTATTAAAGAAGAGAATTTCACTGATCAATTAATTAATTTAGTTCAAAAAACAAAT

AAACTTGAATATGTCATGTTTTCAGTTGATGATATTCTTTATTATAATGAATTCAATCTCAAAGAATAT

TGTTTATCTTTGAATAGTGAGCCATTGGCATTAGGTTTCTATATGAAGTTAAATAAAAATATTACCTAT

TGTCATACTTGTAATCAAGATATAACAATACCATTAAATTCAAATACTATTAGTAGAACAGAGAATAAT

TTTAAATATTTAAAATGGAATAGAAATGATAATGATTGTAAAAGGATTGGAATTATCCATGGGATTTA

TGTTCAACCATTTATAGATGTAATGATATTGATTCAATCATTAATGGTATAGTTAAATATTATGGAATT

AGAAATGGTATTAATCATCCAAATAGATTCGAATTCAATGGTAATAGACCAATCATTCAAAAGCAAATC

TATCAAAATAAACCCTACTGTTTATGTTTATCAGATCACTATTCTCCAATGTCTGTTGTAACTATTAAT

AGAGTTCAAGATGTCTATGATAATCCAATTTATGACCAAACCCTATCTTTAGATGATTTAGATCAATTA

CTTTATTCAAACAAATCATTAAATGATGAAAAATATAAAGAAAATAGTTTATCTTTAAATTTTAAAGT

GTTCATATTGGTGAACTTTTTATTTCTTAA
```

SEQ ID NO: 4: the amino acid sequence of a fragment of SEQ ID NO: 1 having fucosyltransferase activity:
MSILNFISGINSNKINTPKSNNNKFKENGIRIICFSKDRAFQLKEYLRTFFKYLKNDDNGNDKFEIIVD

VLFTYSNEKEKNSYQLVIESFPQVNFIKEENFTDQLINLVQKTNKLEYVMFSVDDILYYNEFNLKEYCL

SLNSEPLALGFYMKLNKNITYCHTCNQDITIPLNSNTISRTENNFKYLKWNRNDNDCKKDWNYPWDLCS

TIYRCNDIDSIINGIVKYYGIRNGINHPNRFEENGNRPIIQKQIYQNKPYCLCLSDHYSPMSVVTINRV

QDVYDNPIYDQTLSLDDLDQLLYSNKSLNDEKYKENSLSLNEKSVHIGELFIS

SEQ ID NO: 5: the codon optimized nucleic acid sequence encoding SEQ ID NO: 4 with an ATG added:
ATGAGCATTCTGAATTTTATTAGCGGCATTAATAGCAATAAAATTAATACCCCGAAAAGCAACAATAAC

AAATTTAAAGAGAATGGCATTCGCATTATTTGCTTCAGCAAAGATCGTGCATTCCAGCTGAAAGAATAT

CTGCGCACCTTCTTCAAATATCTGAAAAATGATGATAATGGCAATGATAAATTTGAAATTATTGTGGAT

GTGCTGTTTACCTATAGCAATGAAAAATTCAAAAATAGCTATCAGCTGGTGATCGAAAGCTTTCCGCAG

GTTAACTTTATTAAAGAAGAAAACTTTACCGATCAGCTGATTAACCTGGTGCAGAAAACCAACAAACTG

GAATATGTGATGTTCAGCGTGGATGATATCCTGTATTACAACGAGTTCAATCTGAAAGAGTATTGCCTG

AGCCTGAATAGCGAACCGCTGGCACTGGGTTTTTATATGAAACTGAATAAAAATATTACCTATTGCCAT

ACCTGCAACCAGGATATTACCATTCCGCTGAATAGCAATACCATTAGCCGCACCGAAAATAACTTTAAA

TACCTGAAATGGAATCGCAACGATAATGATTGCAAAAAAGACTGGAACTATCCGTGGGATCTGTGTAGC

ACCATTTATCGTTGCAACGACATTGACAGCATCATTAATGGTATTGTGAAATATTATGGTATTCGCAAC

GGCATTAATCATCCGAATCGCTTTGAATTAATGGCAACCGTCCGATTATTCAGAAACAAATCTACCAG

AACAAACCGTATTGTCTGTGCCTGAGCGATCATTATTCACCGATGAGCGTTGTTACCATTAATCGTGTT

CAGGATGTGTATGATAACCCGATTTATGATCAGACCCTGAGCCTGGATGATCTGGATCAACTGCTGTAT

AGCAATAAATCCCTGAACGATGAAAAATATAAAGAAAACAGCCTGAGTCTGAACTTCAAAAGCGTTCAT

ATTGGCGAACTGTTCATCAGCTAA

SEQ ID NO: 6: the native nucleic acid sequence encoding SEQ ID NO: 4:
TCAATTTTAAATTTTATATCTGGCATTAATAGTAATAAAATAAATACTCCAAAATCTAATAATAATAAA

TTTAAAGAAAATGGAATTAGAATAATTTGTTTCTCAAAAGATAGAGCATTTCAATTAAAAGAATATCTT

AGAACATTTTTTAAATATTTAAAAAATGATGATAATGGAAATGATAAATTTGAAATTATTGTTGATGTA

TTATTTACATATTCAAATGAGAAATTCAAAAACTCTTATCAATTAGTTATTGAAAGTTTTCCACAAGTT

AATTTTATTAAAGAAGAGAATTTCACTGATCAATTAATTAATTTAGTTCAAAAAACAAATAAACTTGAA

TATGTCATGTTTTCAGTTGATGATATTCTTTATTATAATGAATTCAATCTCAAAGAATATTGTTTATCT

TTGAATAGTGAGCCATTGGCATTAGGTTTCTATATGAAGTTAAATAAAAATATTACCTATTGTCATACT

TGTAATCAAGATATAACAATACCATTAAATTCAAATACTATTAGTAGAACAGAGAATAATTTTAAATAT

TTAAAATGGAATAGAAATGATAATGATTGTAAAAAGGATTGGAATTATCCATGGGATTTATGTTCAACC

ATTTATAGATGTAATGATATTGATTCAATCATTAATGGTATAGTTAAATATTATGGAATTAGAAATGGT

ATTAATCATCCAAATAGATTCGAATTCAATGGTAATAGACCAATCATTCAAAAGCAAATCTATCAAAAT

AAACCCTACTGTTTATGTTTATCAGATCACTATTCTCCAATGTCTGTTGTAACTATTAATAGAGTTCAA

GATGTCTATGATAATCCAATTTATGACCAAACCCTATCTTTAGATGATTTAGATCAATTACTTTATTCA

AACAAATCATTAAATGATGAAAAATATAAAGAAAATAGTTTATCTTTAAATTTTAAAAGTGTTCATATT

GGTGAACTTTTTATTTCTTAA

The present invention is hereby following illustrated by specific working examples.

EXAMPLES

Example 1. Materials and Methods

Media

The Luria Broth (LB) medium consisted of 1% tryptone peptone (Difco, Erembodegem, Belgium), 0.5% yeast extract (Difco) and 0.5% sodium chloride (VWR, Leuven, Belgium). The medium for the shake flasks experiments contained 2.00 g/l NH4Cl, 5.00 g/l (NH4)2SO4, 2.993 g/l KH2PO4, 7.315 g/l K2HPO4, 8.372 g/l MOPS, 0.5 g/l NaCl, 0.5 g/l MgSO4.7H2O, 14.26 g/l sucrose or another carbon source when specified in the examples, 1 ml/l vitamin solution, 100 μl/l molybdate solution, and 1 ml/l selenium solution. The medium was set to a pH of 7 with 1M KOH.

Vitamin solution consisted of 3.6 g/l FeCl2.4H2O, 5 g/l $CaCl_2$.2H2O, 1.3 g/l MnCl2.2H2O, 0.38 g/l CuCl2.2H2O, 0.5 g/l CoCl2.6H2O, 0.94 g/l ZnCl2, 0.0311 g/l H3B04, 0.4 g/l Na2EDTA.2H2O and 1.01 g/l thiamine.HCl. The molybdate solution contained 0.967 g/l Na2MoO4.2H2O. The selenium solution contained 42 g/l SeO2.

The minimal medium for fermentations contained 6.75 g/l NH4Cl, 1.25 g/l (NH4)2SO4, 1.15 g/l KH2PO4 (low phosphate medium) or 2.93 g/l KH2PO4 and 7.31 g/l KH2PO4 (high phosphate medium), 0.5 g/l NaCl, 0.5 g/l MgSO4.7H2O, 14.26 g/l sucrose, 1 ml/l vitamin solution, 100 μl/l molybdate solution, and 1 ml/l selenium solution with the same composition as described above.

Complex medium was sterilized by autoclaving (121° C., 21') and minimal medium by filtration (0.22 μm Sartorius). If necessary the medium was made selective by adding an antibiotic (ampicilin, chloramphenicol, kanamycin).

Cultivation Conditions

A preculture, from a single colony on a LB-plate, in 5 ml LB medium was incubated during 8 hours at 37° C. on an orbital shaker at 200 rpm. From this culture, 2 ml was transferred to 100 ml minimal medium in a 500 ml shake flask and incubated for 16 hours at 37° C. on an orbital shaker at 200 rpm. 4% inoculum was used in a 2 l Biostat B Plus culture vessel with 1.5 l working volume (Sartorius Stedim Biotech, Melsungen, Germany). The culture conditions were: 37° C., stirring at 800 rpm, and a gas flow rate of 1.5 l/min. Aerobic conditions were maintained by sparging with air. The pH was maintained at 7 with 0.5 M $H_2SO_4$ and 4 M KOH. The exhaust gas was cooled down to 4° C. by an exhaust cooler (Frigomix 1000, Sartorius Stedim Biotech, Melsungen, Germany). 10% solution of silicone antifoaming agent (BDH 331512K, VWR Int Ltd., Poole, England) was added when foaming raised during the fermentation (approximately 10 μl). The off-gas was measured with an EL3020 off-gas analyser (ABB Automation GmbH, 60488 Frankfurt am Main, Germany). All data was logged with the Sartorius MFCS/win v3.0 system (Sartorius Stedim Biotech, Melsungen, Germany).

All strains were cultivated at least twice and the given standard deviations on yields and rates are based on at least 10 data points taken during the repeated experiments.

Sampling

The bioreactor contains in its interior a harvest pipe (BD Spinal Needle, 1.2×152 mm (BDMedical Systems, Franklin Lakes, N.J.—USA) connected to a reactor port, linked outside to a Masterflex-14 tubing (Cole-Parmer, Antwerpen, Belgium) followed by a harvest port with a septum for sampling. The other side of this harvest port is connected back to the reactor vessel with a Masterflex-16 tubing. This system is referred to as rapid sampling loop. During sampling, reactor broth is pumped around in the sampling loop. It has been estimated that, at a flow rate of 150 ml/min, the reactor broth needs 0.04 s to reach the harvest port and 3.2 s to re-enter the reactor. At a pO2 level of 50%, there is around 3 mg/l of oxygen in the liquid at 37° C. The pO2 level should never go below 20% to avoid micro-aerobic conditions. Thus 1.8 mg/l of oxygen may be consumed during transit through the harvesting loop. Assuming an oxygen uptake rate of 0.4 g oxygen/g biomass/h (the maximal oxygen uptake rate found at Amax), this gives for 5 g/l biomass, an oxygen uptake rate of 2 g/l/h or 0.56 mg/l/s, which multiplied by 3.2 s (residence time in the loop) gives 1.8 mg/l oxygen consumption.

In order to quench the metabolism of cells during the sampling, reactor broth was sucked through the harvest port in a syringe filled with 62 g stainless steel beads precooled at −20° C., to cool down 5 ml broth immediately to 4° C. Sampling was immediately followed by cold centrifugation (15000 g, 5 min, 4° C.). During the batch experiments, samples for OD600 nm, CDW, and extracellular metabolites were taken each hour using the rapid sampling loop and the cold stainless bead sampling method. When exponential growth was reached, the sampling frequency was increased to every 20 to 30 minutes.

Broth Sampling

Using a rapid sampling, which was coupled to the fermentor, samples of 1 ml broth were withdrawn from the fermentor within 0.5 s. Samples were withdrawn directly into tubes containing 5 ml of quenching solution precooled at −40° C. that were immediately mixed after sampling by vortexing. The exact sample sizes were quantified gravimetrically by weighing the tubes before and after sampling.

Filtrate Sampling

Samples of extracellular culture fluid were obtained with syringe filtration (pore size 0.45 μm, cellulose acetate) at room temperature without beads—Direct filtration of the broth sample After removal of the cells, the obtained filtrate or supernatant was immediately mixed with 5 ml of quenching solution to process these samples in the same way as the broth samples. Also in this case, the exact amount of sample obtained was quantified gravimetrically.

Quenching Procedure

The quenching solution used was a 60% (v/v) aqueous methanol. After quenching of broth samples in the quenching solution, precooled at −40° C., the sample/quenching solution mixture was centrifuged for 5 min at 8000 g in a cooled centrifuge (−20° C.) using a rotor that was precooled at −40° C. After decanting, the supernatant (QS) was stored at −40° C. until extraction. Subsequently, the cell pellets were resuspended in 5 ml of −40° C. quenching solution and again centrifuged. Also, this second supernatant (WS) was stored at −40° C. until extraction. For measurement of metabolites in total broth as well as in the culture filtrate, the same quenching procedure was applied; however, the quenched total broth mixtures (B) or quenched culture filtrates (F) were not centrifuged, but after thorough vortexing, 500 μl of these mixtures was withdrawn for metabolite extraction.

Metabolite Extraction Procedure

Extraction of metabolites from the cell pellets as well as from the 500-μl samples from the quenched total broth was performed with the hot ethanol method [34]. Metabolites were extracted in 75% boiling ethanol (3 min, 90° C.). After cooling the thus obtained extracts were evaporated to dryness in a RapidVap (Labconco Corporation, Kansas, Missouri, USA) during 110 min under vacuum. After resuspension of each residue in 500 μL of H2O, cell debris was removed by centrifugation during 5 min at 5000 g. After decanting the supernatants were stored at −80° C. until further analysis.

Analytical Methods

Cell density of the culture was frequently monitored by measuring optical density at 600 nm (Uvikom 922 spectrophotometer, BRS, Brussel, Belgium). Cell dry weight was obtained by centrifugation (15 min, 5000 g, GSA rotor, Sorvall RC-5B, Goffin Meyvis, Kapellen, Belgium) of 20 g reactor broth in pre-dried and weighted falcons. The pellets were subsequently washed once with 20 ml physiological solution (9 g/l NaCl) and dried at 70° C. to a constant weight. To be able to convert $OD_{600nm}$ measurements to biomass concentrations, a correlation curve of the $OD_{600nm}$ to the biomass concentration was made. The concentrations of glucose and organic acids were determined on a Varian Prostar HPLC system (Varian, Sint-Katelijne-Waver, Belgium), using an Aminex HPX-87H column (Bio-Rad, Eke, Belgium) heated at 65° C., equipped with a 1 cm precolumn, using 5 mM H2SO4 (0.6 ml/min) as mobile phase. A dual-wave UV-VIS (210 nm and 265 nm) detector (Varian Prostar 325) and a differential refractive index detector (Merck LaChrom L-7490, Merck, Leuven, Belgium) was used for peak detection. By dividing the absorptions of the peaks in both 265 and 210 nm, the peaks could be identified. The division results in a constant value, typical for a certain compound (formula of Beer-Lambert).

Carbohydrate Measurements

Glucose, fructose, sucrose and glucose-1-phosphate were measured by HPLC with a Hypercarb column (100×4.6 mm; 5 μm particle size) and were detected with an ELSD detector or mass spectrometer (Antonio et al., 2007; Nielsen et al., 2006). The LOQ of sucrose and G1P were 30 and 20 mg/I, respectively. All samples were diluted within the linear range of the detector, which is between the LOQ and approximately 100 mg/l of the metabolite. When multiple phosphorylated and nucleotide sugars were present in the broth, an adaptation of the method of Bucholz et al was applied (11). In this case a gradient of milliQ water (A) and 20 mM ammonium acetate (B) was used to separate the analytes. The gradient started at 100% A with a flow of 1 ml/min and changed to 100% B at 1 ml/min over 10 minutes. The eluens composition of 100% B was then held for 4 minutes at 1 ml/min and then changed to 100% A at 1 ml/min over 1 minute, after which the flow was increased to 1.2 ml/min and held for 3 minutes to reduce the equilibration time of the column. After these three minutes the flow was reduced again in 2 minutes to 1 ml/min. All analytes were detected with either an ELSD detector or mass spectrometer.

For the analysis of mono-, di-, and oligo-saccharides a Prevail Carbohydrate ES (5μ; 250×4.6 mm) column was used with a gradient of 100% aceton (A), 100% acetonitril (B) and 100% water (C). The gradient is initiated at 20% A, 60% B and 20% C. This is changed over 15 minutes to 15% A, 45% B and 40% C and then changed back to 20% A, 60% B and 20% C within 1 minute. The column is then equilibrated at its initial conditions for 6 minutes. All analytes were either measured with ELSD or mass spectrometer.

Measurement of Cell Dry Weight

From a broth sample, 4×10 g was transferred to centrifuge tubes, the cells were spun down (5000 g, 4° C., 5 min), and the cells were washed twice with 0.9% NaCl solution. The centrifuge tubes containing the cell pellets were dried in an oven at 70° C. for 48 h until constant weight. The cell dry weight was obtained gravimetrically; the tubes were cooled in a desiccator prior to weighing.

Sophorose Polysaccharide Measurement

To determine the amount of sophorose polysaccharide that was produced by a mutant strain in which the heterologous tts gene (50) was expressed, a 100 ml culture of this mutant and of the wild type strain at approximately OD 6 was centrifuged (5500 rpm, 4° C., 5 minutes, Heraus Biofuge stratos). 80 ml of the supernatant was then precipitated with 2 volumes of cold ethanol (100% at −20° C.) en stored overnight at 6° C. The precipitate was separated from the supernatant by centrifugation (5500 rpm, 4° C., 5 min, Hereaus Biofuge stratos) en resuspended in 25 ml distilled water (88). 2 ml of this polysaccharide solution was then hydrolyzed in pyrex boriumsilicate tubes (26×100 mm) at 105° C. with 2.25 M HCl (final concentration) for 4h. To neutralize the solution for glucose measurement, equimolar amounts of NaOH was added to the solution after incubation and cooling. The amount of glucose in the solution was determined with an YSI biochemistry analyser (YSI (UK) Ltd.).

Strains and Plasmids Used for *Dictyostellium discoideum* α1,2-Fucosyltransferase Characterization A codon optimized α1,2-fucosyltransferase originating from *Dictyostellium discoideum* was expressed heterologously in *E. coli* which has the genotype ΔlacZΔglgCΔmanAΔCA on a plasmid which was constructed as described by Aerts et al. (1). CA indicates all genes in the gene cluster that codes for the colanic acid biosynthetic pathway described by Stevenson et al. (86).

Enzyme Isolation Methodology

The strains were grown in LB (10 WI tryptone, 5 g/l yeast extract and 10 WI NaCL) in an overnight culture (100 ml in 500 ml shake flask) at 37° C. and 200 rpm. The cells were harvested by centrifugation (15 minutes at 7500 rpm and 4° C.). This pellet was resuspended in 5 ml PBS buffer and sonicated 3 times for 4 minutes on ice water (cycle 50%, intensity 3). The cell debris was centrifuged again 15 minutes at 7500 rpm and 4° C. The supernatant was used as crude cell extract.

Protein Determination

Protein content of the enzyme extract was measured with the Pierce BCA Protein Assay Kit (Thermo) as specified in the product manual.

Plasmid Construction for the Expression of Heterologous and Homologous Genes

Plasmid which was constructed as described by Aerts et al. (1).

Genetic Methods

Plasmids were maintained in the host *E. coli* DH5a (F−, φ80dlacZΔM15, Δ(lacZYA-argF)U169, deoR, recA1, endA1, hsdR17(rk−, mk+), phoA, supE44, λ−, thi-1, gyrA96, relA1).

Plasmids. pKD46 (Red helper plasmid, Ampicillin resistance), pKD3 (contains an FRT-flanked chloramphenicol resistance (cat) gene), pKD4 (contains an FRT-flanked kanamycin resistance (kan) gene), and pCP20 (expresses FLP recombinase activity) plasmids were obtained from Prof. Dr. J-P Hernalsteens (Vrije Universiteit Brussel, Belgium). The plasmid pBluescript (Fermentas, St. Leon-Rot, Germany) was used to construct the derivates of pKD3 and pKD4 with a promoter library, or with alleles carrying a point mutation.

Mutations. The mutations consisted in gene disruption (knock-out, KO), replacement of an endogenous promoter by an artificial promoter (knock-in, KI), respectively. They were introduced using the concept of Datsenko and Wanner (19).

Transformants carrying a Red helper plasmid were grown in 10 ml LB media with ampicillin (100 mg/l) and L-arabinose (10 mM) at 30° C. to an $OD_{600nm}$ of 0.6. The cells were made electro competent by washing them with 50 ml of ice-cold water, a first time, and with 1 ml ice-cold water, a second time. Then, the cells were resuspended in 50 µl of ice-cold water. Electroporation was done with 50 µl of cells and 10-100 ng of linear double-stranded-DNA product by using a Gene Pulser™ (BioRad) (600 Ω, 25 µFD, and 250 volts).

After electroporation, cells were added to 1 ml LB media incubated 1 h at 37° C., and finally spread onto LB-agar containing 25 mg/l of chloramphenicol or 50 mg/l of kanamycin to select antibiotic resistant transformants. The selected mutants were verified by PCR with primers upstream and downstream of the modified region and were grown in LB-agar at 42° C. for the loss of the helper plasmid. The mutants were tested for ampicillin sensitivity.

Elimination of the Antibiotic Resistance Gene

The selected mutants (chloramphenicol or kanamycin resistant) were transformed with pCP20 plasmid, which is an ampicillin and chloramphenicol resistant plasmid that shows temperature-sensitive replication and thermal induction of FLP synthesis. The ampicillin-resistant transformants were selected at 30° C., after which a few were colony purified in LB at 42° C. and then tested for loss of all antibiotic resistances and of the FLP helper plasmid. The gene knock-outs and knock-ins are checked with control primers and sequenced.

The primers used to construct the various Knock-out and knock-in mutants are listed in Table 1.

TABLE 1

Primers used for the construction of the gene knock outs

| gene | Fw-P1-H1 | Rv-P2-H2 |
|---|---|---|
| lacZ | CATAATGGATTTCCTTACGCGAAATACGG GCAGACATGGCCTGCCCGGTTATTAgtgt aggctggagctgcttc | GTATGTTGTGTGGAATTGTGAGCGGATAA CAATTTCACACAGGAAACAGCTcatatga atatcctccttag |
| glgC | agaccgccggttttaagcagcgggaacat ctctgaacatacatgtaaaacctgcagtg taggctggagctgcttc | gtctggcagggacctgcacacggattgtg tgtgttccagagatgataaaaaaggagtt agtccatatgaatatcctccttag |
| agp | CATATTTCTGTCACACTCTTTAGTGATTG ATAACAAAAGAGGTGCCAGGAgtgtaggc tggagctgcttc | TAAAAACGTTTAACCAGCGACTCCCCCGC TTCTCGCGGGGAGTTTTCTGcatatgaa tatcctccttag |
| pgi | GGCGCTACAATCTTCCAAAGTCACAATTC TCAAAATCAGAAGAGTATTGCgtgtaggc tggagctgcttc | GGTTGCCGGATGCGGCGTGAACGCCTTAT CCGGCCTACATATCGACGATGcatatgaa tatcctccttag |
| pfkA | GACTTCCGGCAACAGATTTCATTTTGCAT TCCAAAGTTCAGAGGTAGTCgtgtaggct ggagctgcttc | GCTTCTGTCATCGGTTTCAGGGTAAAGGA ATCTGCCTTTTTCCGAAATCcatatgaat atcctccttag |
| pfkB | CACTTTCCGCTGATTCGGTGCCAGACTGA AATCAGCCTATAGGAGGAAATGgtgtagg ctggagctgcttc | GTTGCCGACAGGTTGGTGATGATTCCCCC AATGCTGGGGGAATGTTTTTGcatatgaa tatcctccttag |
| pgm via D&W | TGAGAAGGTTTGCGGAACTATCTAAAACG TTGCAGACAAAGGACAAAGCAgtgtaggc tggagctgcttc | CATACGTAAAAAAGGGCGATCTTGCGACC GCCCTTTTTTTATTAAATGTGTcatatga atatcctccttag |
| pgm::kan | TGAGAAGGTTTGCGGAACTATCTAAAACG TTGCAGACAAAGGACAAAGCAACGAAAGG CTCAGTCGAAAG | CATACGTAAAAAAGGGCGATCTTGCGACC GCCCTTTTTTTATTAAATGTGTAGAACTC CAGCATGAGATCC |
| pgm::GFP | TGAGAAGGTTTGCGGAACTATCTAAAACG TTGCAGACAAAGGACAAAGCAgtgtaggc tggagctgcttc | CATACGTAAAAAAGGGCGATCTTGCGACC GCCCTTTTTTTATTAAATGTGTCATCCGT CAGGATGGCCTTC |
| ptsG | gccacgcgtgagaacgtaaaaaagcacc catactcaggagcactctcaattgtgtag gctggagctgcttc | Cacctgtaaaaaaggcagccatctggctg ccttagtctccccaacgtcttacggacat atgaatatcctccttag |
| glk | CGAGAAGGCCCGGATTGTCATGGACGATG AGATACACCGGAATATCATGGgtgtaggc tggagctgcttc | CCAGGTATTTACAGTGTGAGAAAGAATTA TTTTGACTTTAGCGGAGCAGTTGAAGAca tatgaatatcctccttag |
| malPQ | ATATCCAGCCAGTCTTCCGGCTGTAGTCC TAACAGAGCACTGTTACTGTCagcattac acgtcttgagcg | GCTTTAAGTGGTTGAGATCACATTTCCTT GCTCATCCCCGCAACTCCTCCcatatgaa tatcctccttag |
| MP KI | ATATCCAGCCAGTCTTCCGGCTGTAGTCC TAACAGAGCACTGTTACTGTC *GTAAAACGACGGCCAGTG* | CAACGGCCATTTTTTGCACTTAGATACAG ATTTTCTGCGCTGTATTGCATTG*CCGGGA TCCGATGCATATGG* |

TABLE 1-continued

Primers used for the construction of the gene knock outs

| gene | Fw-P1-H1 | Rv-P2-H2 |
|---|---|---|
| ycjU | TTTTATTTTGCCCTTCAATGGGACCGCTA CCAAACATCAGGAGGATGAATGAAACagc attacacgtcttgagcg | TTCCGTTGAAGGCAACAGTAATTGCGCCC CGGTTAAGCCCGCGCCGATCCcatatgaa tatcctccttag |
| CA via D&W | GTAGCATTGTTCCTAAGTATGACTCCATT TTTCCAGGAATGGTCGCAAATCgtgtagg ctggagctgcttc | TTCACGCCGCATCCGGCAAGCAAACCAGC TCATAAGCCGGGAGAACAACCcatatgaa tatcctccttag |
| CA via sacB | TTCACGCCGCATCCGGCAAGCAAACCAGC TCATAAGCCGGGAGAACAACCccgcttac agacaagctgtg | GTAGCATTGTTCCTAAGTATGACTCCATT TTTCCAGGAATGGTCGCAAATCagccatg acccgggaattac |
| wcaJ via sacB | ATCGCCGACCACTTCGCGCCGCTGATGGT TTTTTCACGTAAGCTCATATCccgcttac agacaagctgtg | GGATCTTCCCTTACCCCACTGCGGGTAAG GGGCTAATAACAGGAACAACGagccatga cccgggaattac |
| wcaJ via sacB and fusion PCR | GGGGGCCCCCGGGGGTATGAGCTTACGTG AAAAAACCATCAG | GGGCCCGGGCCCGGGCGTTGTTCCTGTTA TTAGCCCCTTACCC |
| wcaJ via D&W | ATCGCCGACCACTTCGCGCCGCTGATGGT TTTTTCACGTAAGCTCATATCgtgtaggc tggagctgcttc | GGATCTTCCCTTACCCCACTGCGGGTAAG GGGCTAATAACAGGAACAACGcatatgaa tatcctccttag |
| wcaJ via D&W_2 | TTTTGATATCGAACCAGACGCTCCATTCG CGGATGTACTCAAGGTCGAACgtgtaggc tggagctgcttc | TCTATGGTGCAACGCTTTTCAGATATCAC CATCATGTTTGCCGGACTATGcatatgaa tatcctccttag |
| galET-H1-P22-RBS | TAGCCAAATGCGTTGGCAAACAGAGATTG TGTTTTTTCTTTCAGACTCATCTTTGTTT CCTCCGAATTCG | CGGTTCGACGCATGCAGGCATGAAACCGC GTCTTTTTTCAGATAAAAAGCcatatgaa tatcctccttag |
| galET extended homolog y | ACCAATCAAATTCACGCGGCCAGGCGCCT GAATGGTGTGAGTGGCAGGGTAGCCAAAT GCGTTGGCAAAC | GTCGGTAGTGCTGACCTTGCCGGAGGCGG CCTTAGCACCCTCTCCGGCCAACGGTTCG ACGCATGCAGGC |

Example 2. Engineering and Usage of Base Strain 1 (Carbon Source: Sucrose; Converted into Glucose-1-Phosphate and Fructose by Sucrose Phosphorylase)—Screening of Different Sucrose Phosphorylases An important requirement for the success of 'base strain 1' is the existence of a potent sucrose phosphorylase. However, though *E. coli* has a putative sucrose phosphorylase (SP), it does not grow on a minimal medium with sucrose as sole carbon source. Therefore, 6 sucrose phosphorylases from a variety of microbial sources were screened (Table 2).

To this end, 6 transformants of the wild type *E. coli* were constructed each carrying a plasmid [pCX-promoter-SP] encoding for one of the sucrose phosporylase (SP) listed in Table 2. The performance of these strains was evaluated in shake flasks, using sucrose as sole carbon source. The wild type strain (WT) was incorporated in the experimental design as a control ($\mu WT=0$).

TABLE 2

Screened sucrose phosphorylases

| Source sucrose phosphorylase | Abbreviation |
|---|---|
| *Bifidobacterium adolescentis* | BA |
| *Lactobacillus acidophilus* | LA |
| *Streptococcus mutans* | SM |
| *Leuconostoc mesenteroides* B742 | LM B742 |
| *Leuconostoc mesenteroides* B1149 | LM B1149 |
| *Leuconostoc mesenteroides* B1355 | LM B1355 |

In this screening experiment, the growth rate of the various transformants was monitored and linked to the performance of the sucrose phosphorylases. According to this reasoning the best growing strain does posses the best performing sucrose phosphorylase.

Figure 2:
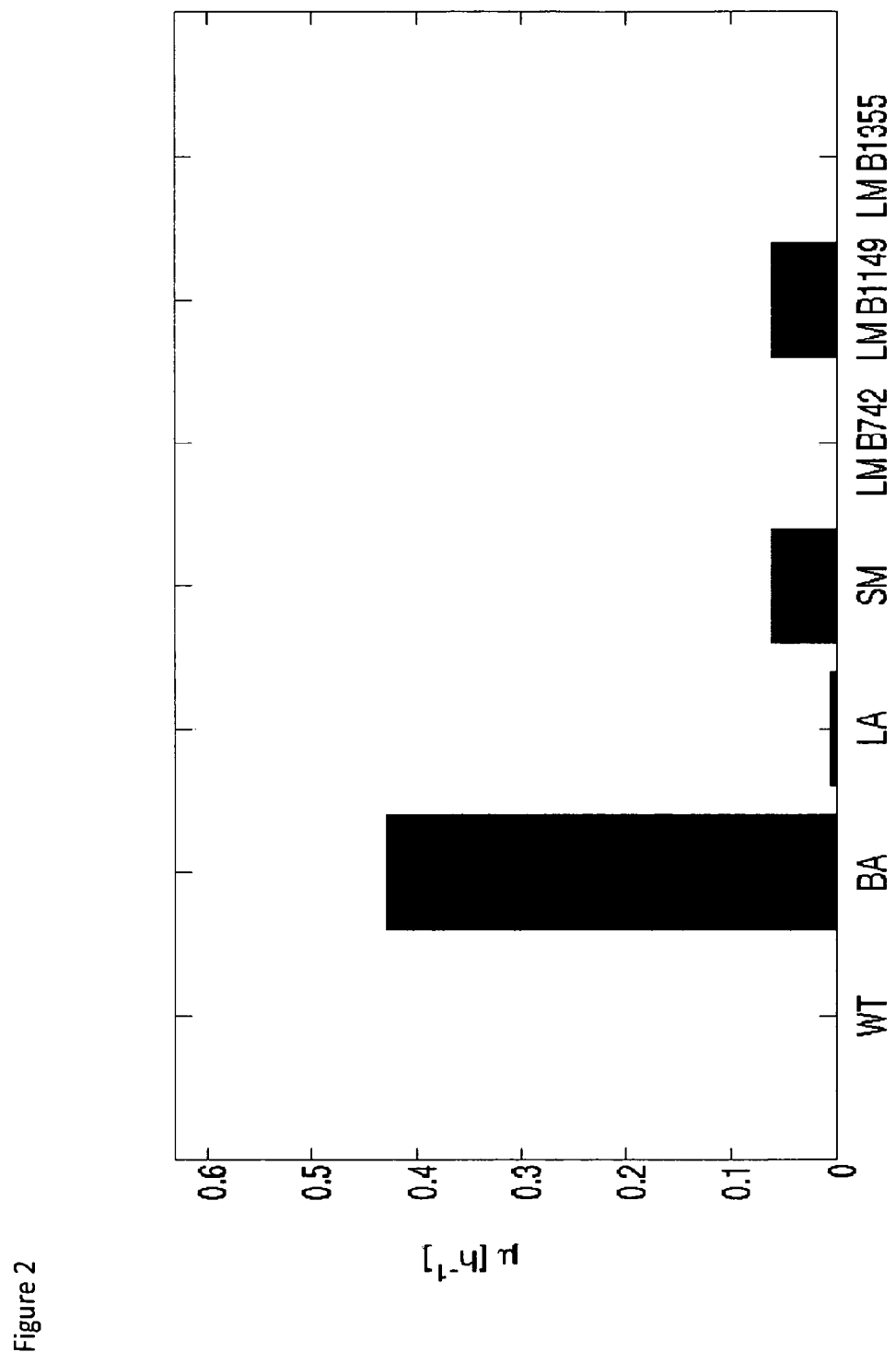
FIG. 2: Growth rate of *E. coli* transformants on minimal medium carrying a plasmid encoding for a sucrose phosphorylase. (Abbreviations are given in Table 2).

The growth rate of the various transformants is depicted in FIG. 2, the principle applied on for the production of a specialty carbohydrate is depicted in FIG. 1: (a) A normal equilibrium reaction, which occurs in the current production technologies (b) pull/push principle: the equilibrium is shifted towards the saccharide and activated saccharide. The main goal of a cell is to grow, hence it pulls, in this figure at the saccharide to form biomass. Due to this pulling effect, the activated saccharide will accumulate in the cell and pushes the production pathway.

Example 3. Characterization of the Sucrose Phosphorylase of *Bifidobacterium adolescentis*

Various artificial constitutive promoters have been inserted to evaluate the influence of the promoter strength on the growth rate. To this end, a weak, medium strength, and strong promoter from a promoter library available at The Centre of Expertise-Industrial Biotechnology and Biocatalysis (Ghent University) were introduced. The medium strength promoter, which yielded the highest growth rate, was finally retained.

The affinity constant and the maximal growth rate of the E. coli strain carrying a plasmid encoding for the sucrose phosphorylase of Bifidobacterium adolescentis were determined. To this end, batch and chemostat experiments were run. The influence of the phosphate concentration on these parameters was checked as well (Table 3).

The kinetic properties of the engineered strain are listed in Table 3. It is clear that the kinetic properties of the engineered strain are adequate in view of future industrial applications.

TABLE 3

Growth characteristics of an E. coli carrying the
Bifidobacterium adolescentis sucrose phosphorylase.

|  | High $PO_4^{3-}$ | Low $PO_4^{3-}$ |
|---|---|---|
| $\mu_{max}$ ($h^{-1}$) | 0.5 | 0.46 |
| $K_s$ (mg/L) | <10 | +/−10 |

High $PO_4^{3-}$ = 64 mM; low $PO_4^{3-}$ = 8.5 mM.

Figure 3:
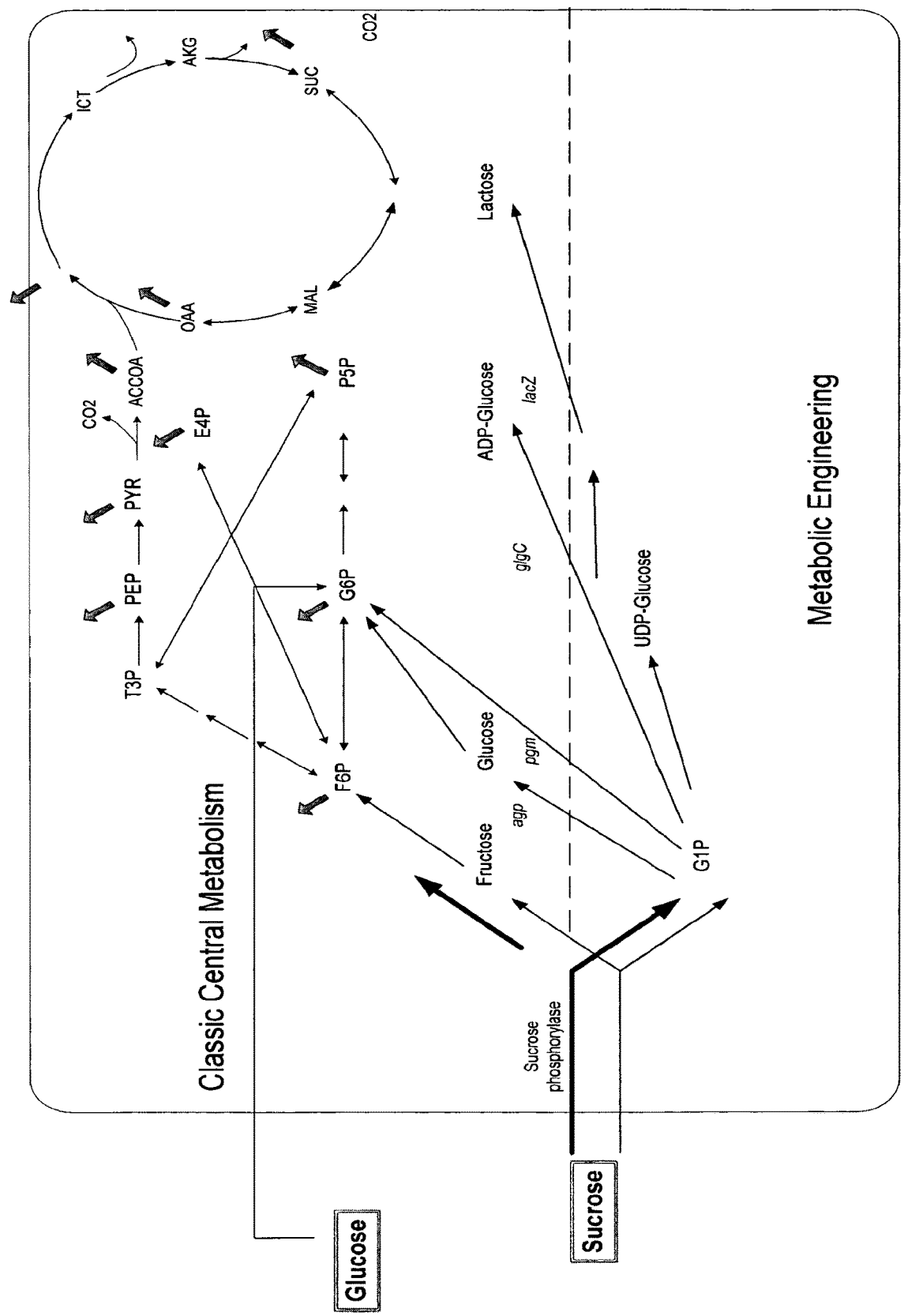
FIG. 3: Projected carbon flow in the wild type strain. Small arrow: Indicating reactions in the metabolism. Bold arrow: Indicating enhanced or novel introduced reactions. Cross: indicates the knocking-out of a gene or rendering it less functional.
Figure 4:
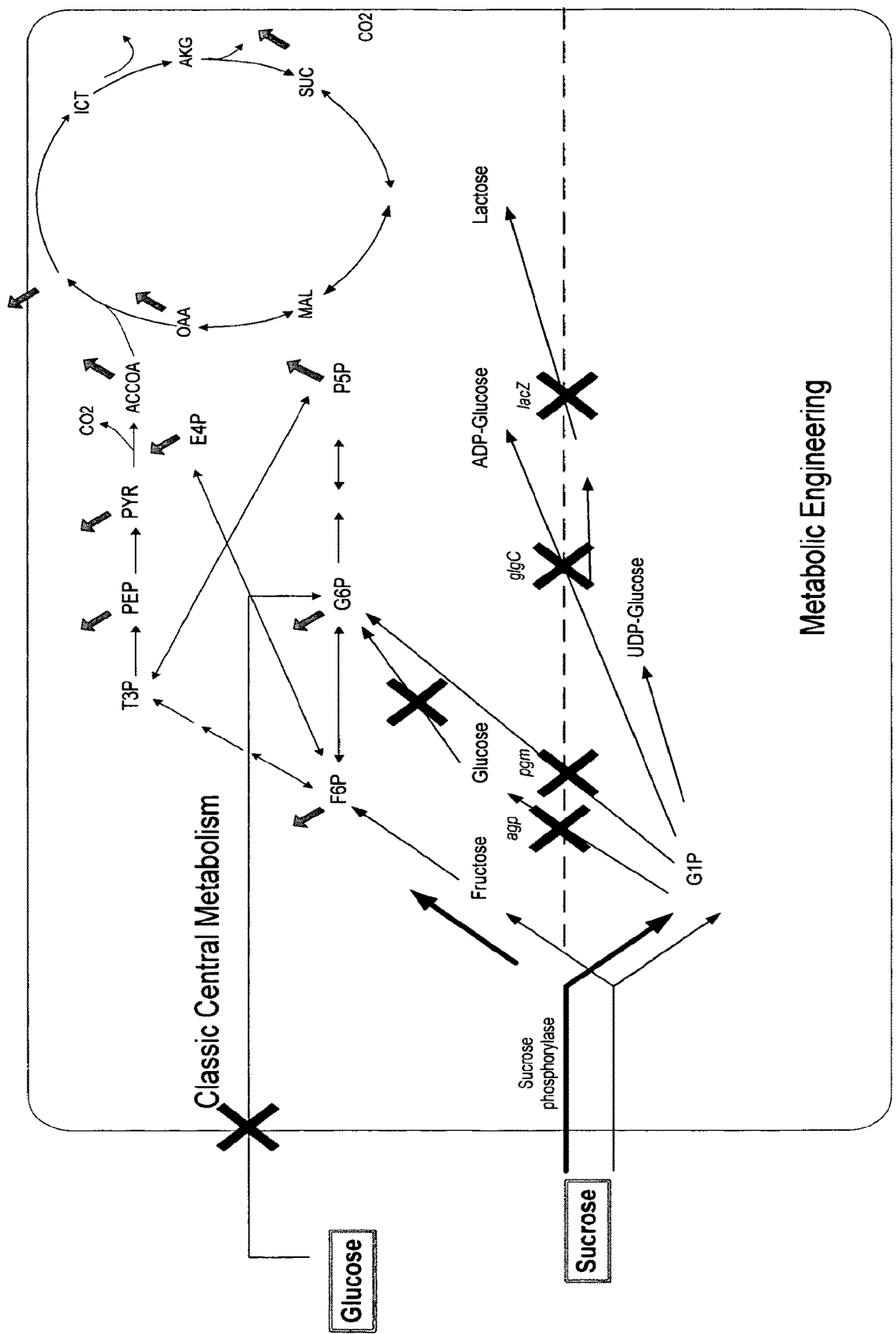
FIG. 4: Projected carbon flow in Base strain 1. The αglucose-1-phosphate (αG1P) pool in Base strain 1 increases because the main reactions that convert αG1P into cellular components are eliminated. Small arrow: Indicating reactions in the metabolism. Bold arrow: Indicating enhanced or novel introduced reactions. Cross: indicates the knocking-out of a gene or rendering it less functional.

Example 4. Engineering Strategy for an Increased Supply of a Glucose-1-Phosphate To validate the rational of the engineering strategy it is important to demonstrate an increased pool of αglucose-1-phosphate in the mutant strain (FIG. 3), compared to the αglucose-1-phosphate pool in the wild type (FIG. 4). In 'Base strain 1' the microbial metabolism is split into two disconnected parts because the main reactions able to convert α glucose-1-phosphate to biomass production were eliminated. One part of the metabolism converts the fructose moiety into biomass and numerous bio-catalytic enzymes (classic central metabolism). The other part converts the αglucose-1-phosphate moiety of sucrose.

The α glucose-1-phosphate concentration was determined both for the wild type and some engineered strains. To this end, batch experiments were performed, using sucrose as sole carbon source.

The α Glucose-1-Phosphate Pool: Comparing the Wild Type and the Plug Strain

To evaluate the potential of the envisaged metabolic engineering strategy, the αglucose-1-phosphate pool was determined in:
  the wild type E. coli MG1655 grown on glucose,
  E. coli MG1655 p22BaSP grown on sucrose,
  E. coli MG1655 ΔglgC Δpgm ΔlacZ p22BaSP grown on sucrose The size of this pool is of major importance because the metabolically engineered pathways of the various specialty carbohydrates to be produced all use αglucose-1-phosphate as prime precursor. Hence, the larger the αglucose-1-phosphate pool, the more precursors that is available for the production of the various specialty carbohydrates.

Figure 5:
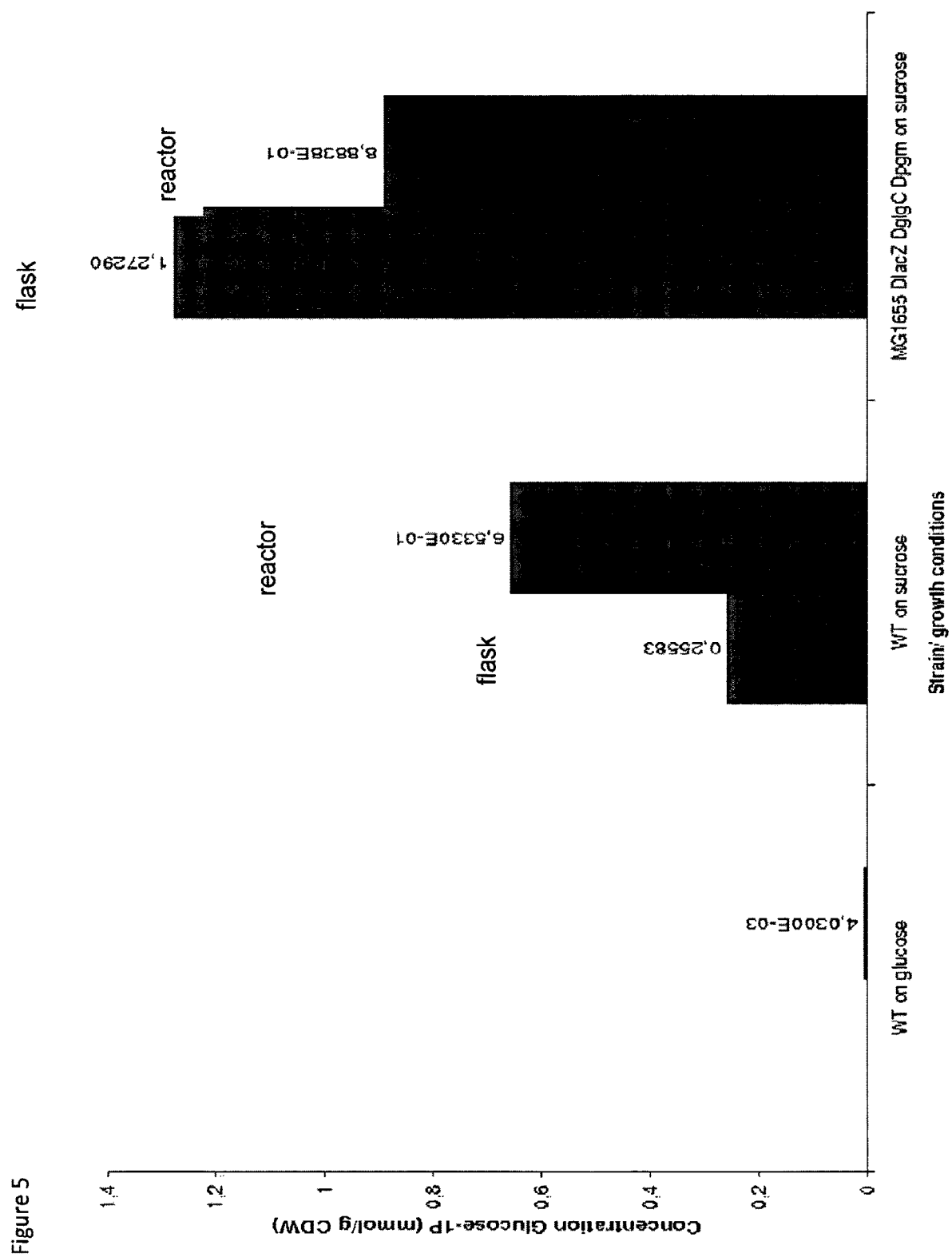
FIG. 5: The αglucose-1-phosphate pool in the wild type *E. coli* MG1655 (WT) grown on glucose, *E. coli* MG1655 P22-BaSP grown on sucrose, and in the plug strain MG1655 AglgC Δpgm ΔlacZ P22-BaSP grown on sucrose: shake flask experiments and 1.5 L batch experiments.

The shake flasks results are depicted in FIG. 5. The intracellular glucose-1-phosphate concentration is 4.03 $10^{-3}$ mmol/gcDW, 0.26 mmol/gcDW, and 1.27 mmol/gcDW, respectively. A >20000% increase in the G1P pool is thus already achieved. This increased pool enables the efficient production of a variety of specialty carbohydrates.

In the wild type E. coli MG1655 strain glucose-1-phosphate is a precursor of cell wall related components, glycogen, etc. A limited flow of carbon, typically coming from αglucose-6-phosphate, suffices to supply the cell with sufficient αglucose-1-phosphate to produce these minor biomass fractions. Hence, the αglucose-1-phosphate pool is of limited size (4.03 $10^{-3}$ mmol/gcDW).

This is in contrast with the proposed strategy to use sucrose as carbon source. Compared to the wild type E. coli MG1655 strain an increased glucose-1-phosphate pool has been shown in the mutant strains that contain a potent sucrose phosphorylase that efficiently splits the inexpensive sugar sucrose into fructose and αglucose-1-phosphate.

Figure 6:
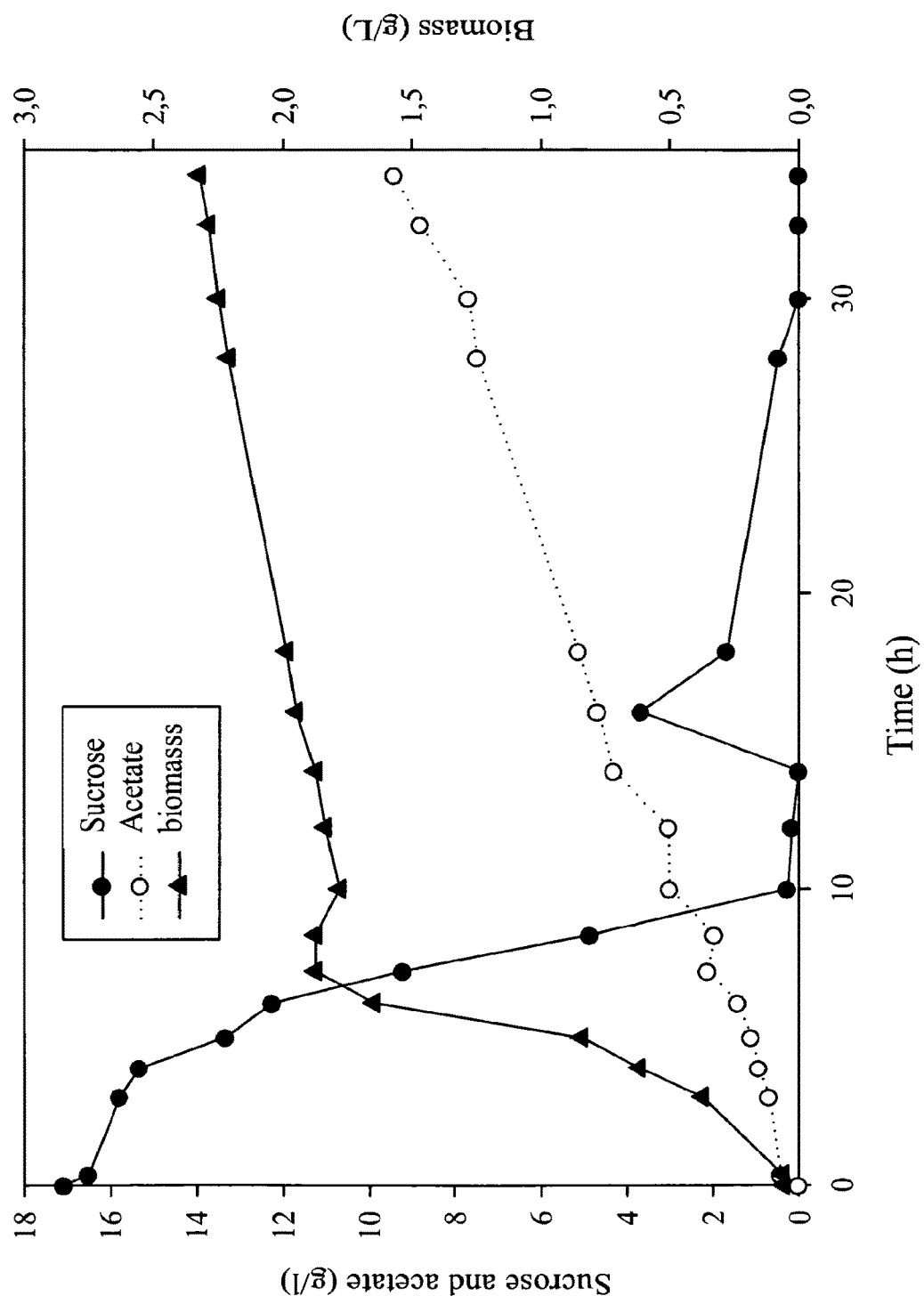
FIG. 6: Evolution of sucrose, acetate and the biomass concentration during a culture of ΔpgmΔlacZΔglgC (3KO) P22-BaSP on buffered LB medium.

The results obtained in a 1.5 L batch reactor are depicted in FIG. 6. The intracellular αglucose-1-phosphate concentration is 4.03 $10^{-3}$ mmol/gcDW, 0.65 mmol/gcDW, and 0.89 mmol/gcDW, respectively.

Figure 7:
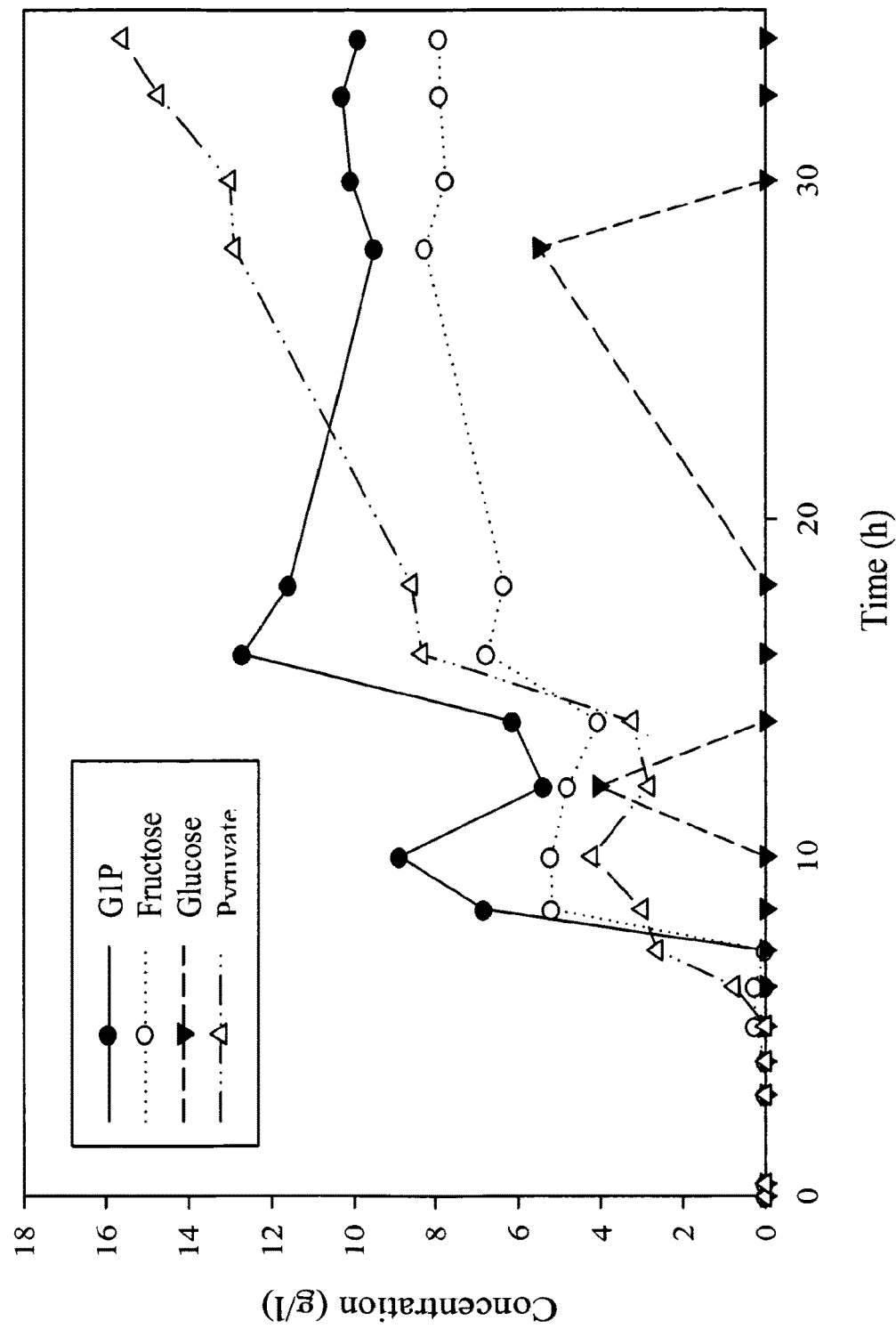
FIG. 7: Evolution of αGlucose-1-phosphate, fructose, glucose, and pyruvate concentration during a culture of ΔpgmΔlacZΔglgC (3KO) P22-BaSP on buffered LB medium.

Production of αGlucose-1-Phosphate by ΔPgmΔlacZΔglgC (3KO) P22-BaSP on Buffered LB Medium at Reactor Scale The ability of ΔpgmΔlacZΔglgC P22-BaSP to produce αglucose-1-phosphate was verified. To this end, a culture with buffered LB medium with about 15 g/L sucrose was run. At about 15h a concentrated sucrose solution, containing phosphate was added. In FIG. 7 and FIG. 6 the concentration of the most important (by)products are depicted. The maximal growth rate during the batch phase is about 0,552 h−1.

During the batch phase per mole of sucrose that is degraded 0.74 mole of glucose-1-phosphate is generated. Ideally, 1 mole of αglucose-1-phosphate can be generated. However, the 3KO studied still contains genes whose products are able to convert αglucose-1-phosphate, e.g., agp.

From the moment all sucrose is consumed, the concentration of glucose-1-phosphate decreases and the concentration of glucose increases which is due to the activity of Agp.

Subsequently at about 15 h additional sucrose is added, which is again converted to glucose-1-phosphate and which accumulates in the medium. Fructose accumulates as well in the medium, which indicates that the cell has limited means to further metabolize this compound (0.64 mole of fructose per mole of sucrose).

In a subsequent experiment, sucrose and phosphate were added on regular time intervals during the course of the fermentation. A maximum αglucose-1-phosphate concentration of about 57 g/L was achieved.

Example 5. Inactivation of the Gene Coding for Phosphoglucomutase

To split the metabolism according to example 1-4 the gene coding for phosphoglucomutase has to be knocked out. Via the classical methodology described by Datsenko and Wanner (19) a knock out results into a chromosomal scar of approximately 84 base pairs. The strains in which this gene was deleted in this manner seem to grow on a complex medium but, to our surprise, did not grow on a minimal medium as described in the materials and methods section. However, the strain did grow on a minimal medium when the kanamycine cassette was left behind. Apparently the removal of the original sequence at this chromosomal location seemed to interfere with growth on a minimal medium but the replacement of this specific sequence (pgm gene), coding for phosphoglucomutase, by a sequence with a similar length did not. This fact was validated by replacing the pgm gene with a part of the GFP gene which has exactly the same size as the pgm gene. This resulted also in a mutant strain that could grow on a minimal medium. The sequences of these strains at the chromosomal location of pgm are shown in FIG. 11, FIG. 12, FIG. 13, and FIG. 14.

Example 6. Cellobiose Production in E. coli

Figure 8:
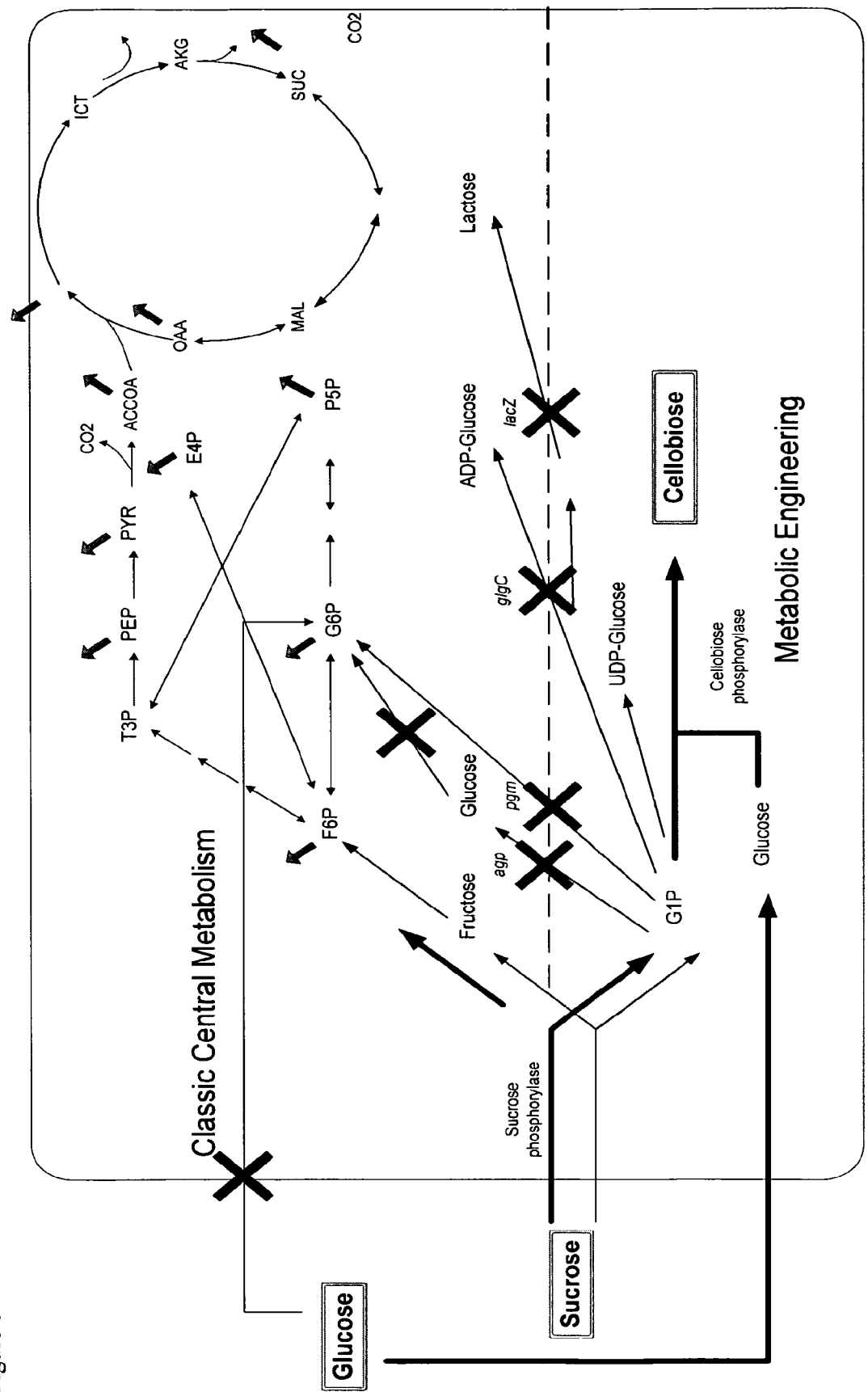
FIG. 8: Schematic view of the cellobiose producer ΔpgmΔlacZΔglgC (3KO) P22-BaSP-CuCP.

Cellobiose producing strains have been constructed starting from 'Base strain 1' (FIG. 8). To this end a plasmid containing both a sucrose phosphorylase (Bifidobacterium adolescentis) and cellobiose phosphorylase (Cellulomonas uda) have been inserted in the wild type, in E. coli MG1655 Δ ΔglgC Δpgm ΔlacZ (3KO), and in E. coli MG1655 Δagp ΔglgC Δpgm ΔlacZ (4KO) (Table 4). Additional genes to be knocked out are glk and ptsG, since both convert glucose into glucose-6-phosphate.

TABLE 4

Cellobiose producing strain

| | Reaction |
|---|---|
| Knock-out | |
| lacZ | Glu + Gal ↔ Lactose |
| pgm | G1P ↔ G6P |
| glgC | G1P + ATP + H ↔ ADP-glucose + PPi |
| agp | G1P + $H_2O$ → Glu + Pi |
| ycjM | Suc → G1P + Fruc |
| ptsG | Glu + PEP → G6P + Pyr |
| glk | Glu + ATP → G6P + ADP |
| Knock-in | |
| Sucrose phosphorylase | Sucrose + Pi → G1P + Fruc |
| Cellobiose phosphorylase | G1P + Glu → Cellobiose + Pi |

Comparing the Wild Type and the Plug Strain

To evaluate the potential of the envisaged metabolic engineering strategy to produce specialty carbohydrates the production of cellobiose was investigated in various engineered strains:

E. coli MG1655 (WT) P22-BaSP P22-CuCP
E. coli MG1655 ΔglgC Δpgm ΔlacZ (3KO) P2-BaSP P22-CuCP
E. coli MG1655 ΔglgC Δpgm ΔlacZ Δagp (4KO) P22-BaSP P22-CuCP To this end shake flask experiments were performed. The medium contained buffered LB medium and sucrose and glucose were added in equal amounts to the shake flasks, so that a final concentration of 1.978 g cellobiose/L was achieved in the shake flask (Table 5). The shake flasks results are depicted in FIG. 5. The (extracellular) concentration of the desired product cellobiose increases with the number of mutations that has been introduced.

TABLE 5

Cellobiose production of various engineered strains

| Strain | Abbreviation | Cellobiose (g/L) |
|---|---|---|
| E. coli MG1655 P22-BaSP P22-CuCP | WT P22-BaSP P22-CuCP | 0 |
| E. coli MG1655 ΔglgC Δpgm ΔlacZ P22-BaSP P22-CuCP | 3KO P22-BaSP P22-CuCP | 0.539 |
| E. coli MG1655 ΔglgC Δpgm ΔlacZ Δagp P22-BaSP P22-CuCP | 4KO P22-BaSP P22-CuCP | 1.978 |

Production of cellobiose by ΔpqmΔlacZΔglgCΔagp (4KO) P22-BaSP P22-CuCP on buffered LB medium at reactor scale.

The ability of ΔpgmΔlacZΔglgCΔagp P22-BaSP P22-CuCP to produce cellobiose was verified on reactor scale in a preliminary experiment. To this end, a culture with buffered LB medium was run. At about 9h and on specific time points a solution containing 500 g/L sucrose and 250 g/L glucose was added to the culture.

A conversion efficiency of about 30% (mol cellobiose produced/mol sucrose consumed) was achieved and about 40% of the glucose moiety of sucrose ended up in cellobiose or in glucose-1-phosphate. A titer of about 15 g/L of cellobiose was achieved at the end of the culture.

Secondly, the production of cellobiose was verified in a batch culture starting from 70 g/l sucrose with a high concentration of phosphate and low concentration of phosphate. High phosphate indicates a phosphate concentration of 0.2 M phosphate, low phosphate indicates a concentration of 13 mM phosphate. This affected the production significantly. The high concentration of phosphate resulted in a final titer of approximately 20 g/l and a yield of 0.33 g/g, while a low phosphate concentration resulted in a final titer of 42 g/l and a yield on consumed sucrose of 0.84 g/g (FIG. 9).

Example 7. Engineering Base Strain 2 (Sucrose-Sucrose Synthase) and its Uses

By metabolically engineering E. coli a base strain is constructed that is an efficient producer of specialty carbohydrates and their derivatives whose pathway starts from UDP-glucose.

By introducing sucrose synthase (e.g., coming from Solanum tuberosum), sucrose is split into fructose and UDP-glucose. By additionally knocking-out genes coding for UDP-glucose 4 epimerase (galE), UDP-glucose galactose-1-P uridilyltransferase (galT), glucose-1-P uridilyltransferase (galU, galF), 5'-nucleotidase/UDP-sugar hydrolase (ushA), UDP-glucose 6-dehydrogenase (ugcf), belonging to the colanic acid operon (ca) a mutant is constructed which accumulates UDP-glucose (Table 6).

TABLE 6

Base strain UDP-Glucose

| | Reaction |
|---|---|
| Knock-out | |
| ca | → colanic acid |
| galU | G1P + UTP ↔ UDP-Glc + PPi |
| galF | G1P + UTP ↔ UDP-Glc + PPi |
| galE | UDP-Glc ↔ UDP-Gal |
| galT | UDP-Glc + Gal1P ↔ UDP-Gal + G1P |
| ushA | UDP-sugar + $H_2O$ ↔ uridine-5'-phosphate + $2H^+$ + an aldose-1-phosphate |
| ugd | 2 NAD + UDP-sugar + $H_2O$ ↔ 2 NADH + UDP-glucuronate + $3H^+$ |
| Knock-in | |
| Sucrose synthase | Suc + UDP → UDP Glu + Fruc |

Example 8. Expression of Sucrose Synthase in E. coli

The activity of sucrose synthase was determined using an in vitro assay. A sucrose synthase from Solanum tuberosum was heterologously expressed in E. coli BL21. From this culture an enzyme extract was prepared, which was incubated with 500 mM sucrose and 2 mM UDP. The evolution of the amount UDP-Glucose produced is given in Table 7.

TABLE 7

Sucrose synthase enzym assay demonstrating the activity of cleavage reaction of sucrose synthase (Mixture sontained 500 mM sucrose and 2 mM UDP)

| Sampling time | UDP-Glucose formed |
|---|---|
| 0 h 10 min | 5 mg/L |
| 1 h 40 min | 64 mg/L |
| 24 h | 300 mg/L |

Example 9. Sophorose Production

Starting from base strain 2 (UDP-Glucose), a strain is constructed which produces large quantities of sophorose, as a polymer of sophorose units. This is achieved by additionally introducing the gene tts from *Streptococcus pneumoniae* (50). Sophorose units can be generated out of the sophorose polymer in two ways, i.e., via acid hydrolysis or via enzymatic conversion. Such an enzyme can be (over)expressed in the producer strain as well.

Figure 15:
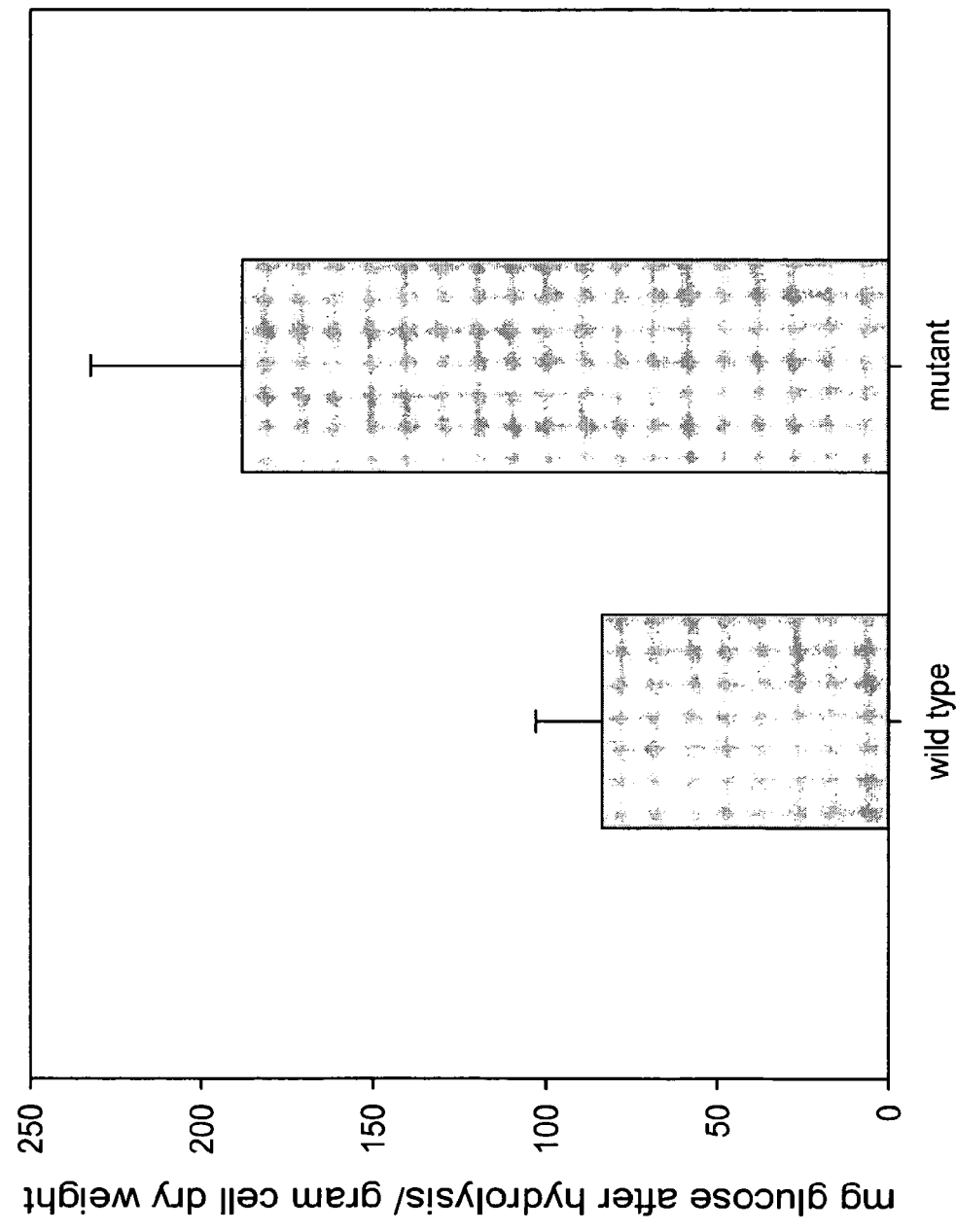
FIG. 15: The amount of glucose that was released after polysaccharide hydrolysis for the wild type strains transformed with a heterologous sucrose phosphorylase originating from *Bifidobacterium adolescentis* and a mutant strain ΔpgmΔagpΔglgCΔlacZΔglkΔptsG with a heterologous sucrose phosphorylase originating from *Bifidobacterium adolescentis* and a heterologous gene tts originating from *Streptococcus pneumoniae*.

To evaluate the potential of the metabolic engineering strategy the sophorose polymer was determined for *E. coli* MG1655 P22-BaSP P22-tts, and a 6KO P22-BaSP P22-tts strain (*E. coli* MG1655 ΔglgC Δpgm ΔlacZ Δagp ΔptsG Δglk) by growing these strains on a minimal medium containing lactose as sole carbon source. The results are depicted in FIG. 15. These results indicate that the mutant strains produce significantly more sophorose polymer in comparison to the wild type strain.

Example 10. Engineering Base Strain 3 (Lactose-Lactose Phosphorylase) and its Uses By introducing lactose phosphorylase (20), lactose is split into glucose and galactose-1-P. By additionally knocking-out genes coding for agp, galE, galT, lacZ, and the metabolism is split into two disconnected parts. However, all possible combinations of these genes result in increased accumulation of galactose-1-phosphate. Instead of knocking-out these genes, this goal can also be achieved by rendering them defective or by reducing their expression (Table 8).

TABLE 8

Base strain 3 Galactose-1-phosphate (Lactose-lactose phosphorylase)

| | Reaction |
|---|---|
| Knock-out | |
| lacZ | Glu + Gal ↔ Lactose |
| galE | UDP-Glc <--> UDP-Gal |
| agp | G1P + H2O → Glu + Pi |
| galT | UDP-Glc + Gal1P <--> UDP-Gal + G1P |
| Knock-in | |
| Lactose phosphorylase | Lactose + Pi → Gal1P + Glucose |

Example 11. Galactose(β1-4)L-Rhamnose Production

Starting from base strain 3, a Gal(δ1-4)L-Rha producer is constructed by additionally introducing a gene coding for an (Ga)lacto-N-biose D-galactosyl-(β1-4)-L-rhamnose phosphorylase, which convert Galactose-1-phosphate and rhamnose into Gal(β1-4)L-Rha and phosphate.

A fermentation is performed using lactose as main carbon source yielding quantities of Gal(β1-4)L-Rha. L-rhamnose is added to the medium. Undesired degradation of rhamnose is prevented by knocking out genes involved in the degradation of rhamnose (rhaA, rhaB, rhaC, rhaD).

Example 12. Engineering Base Strain 4 (Lactose-Lactose Synthase) and its Uses By introducing lactose synthase (71, 72) lactose is split into glucose and UDP-galactose. By additionally knocking-out genes coding for beta-galactosidase (lacZ), UDP-glucose, galactose-1-P uridilyltransferase (galT) UDP-glucose 4 epimerase (galE), 5'-nucleotidase/UDP-sugar hydrolase (ushA), UDP-glucose 6-dehydrogenase (ugcf), belonging to the colanic acid operon (ca) a mutant is constructed which accumulates UDP-Galactose (Table 9).

TABLE 9

Base strain 4 UDP-Galactose (Lactose synthase)

| | Reaction |
|---|---|
| Knock-out | |
| lacZ | Glu + Gal ↔ Lactose |
| galE | UDP-Glc <--> UDP-Gal |
| galT | UDP-Glc + Gal1P <--> UDP-Gal + G1P |
| ca | → colanic acid |
| ushA | UDP-sugar + H$_2$O <--> uridine-5'-phosphate + 2H$^+$ + an aldose-1-phosphate |
| ugd | 2 NAD + UDP-sugar + H$_2$O <--> 2 NADH + UDP-glucuronate + 3H$^+$ |
| Knock-in | |
| Lactose synthase | Lactose → UDP-Gal + Glu |

Example 13. Galactinol Production

Starting from base strain 4, a galactinol producer is constructed by additionally introducing a gene coding for an Inositol 3-alpha-galactosyltransferase which catalyzes the conversion:
UDP-galactose+myo-inositol=UDP+O-α-D-galactosyl-(1→3)-1D-myo-inositol A fermentation is performed using lactose as main carbon source yielding quantities of galactinol in which myo-inositol is added to the medium.

Example 14. Globotriose Production

Starting from base strain 4, a globotriose producer is constructed by additionally introducing the gene IgtC from *Neisseria meningitidis* (3) encoding for a α-1,4-Gal transferase, which catalyzes the conversion UDP-Gal+Lactose→UDP+Globotriose. A fermentation is performed using lactose as main carbon source yielding quantities of globotriose.

Example 15. Engineering Base Strain 5 and Producing Fucosylated Sugars

Figure 10A:
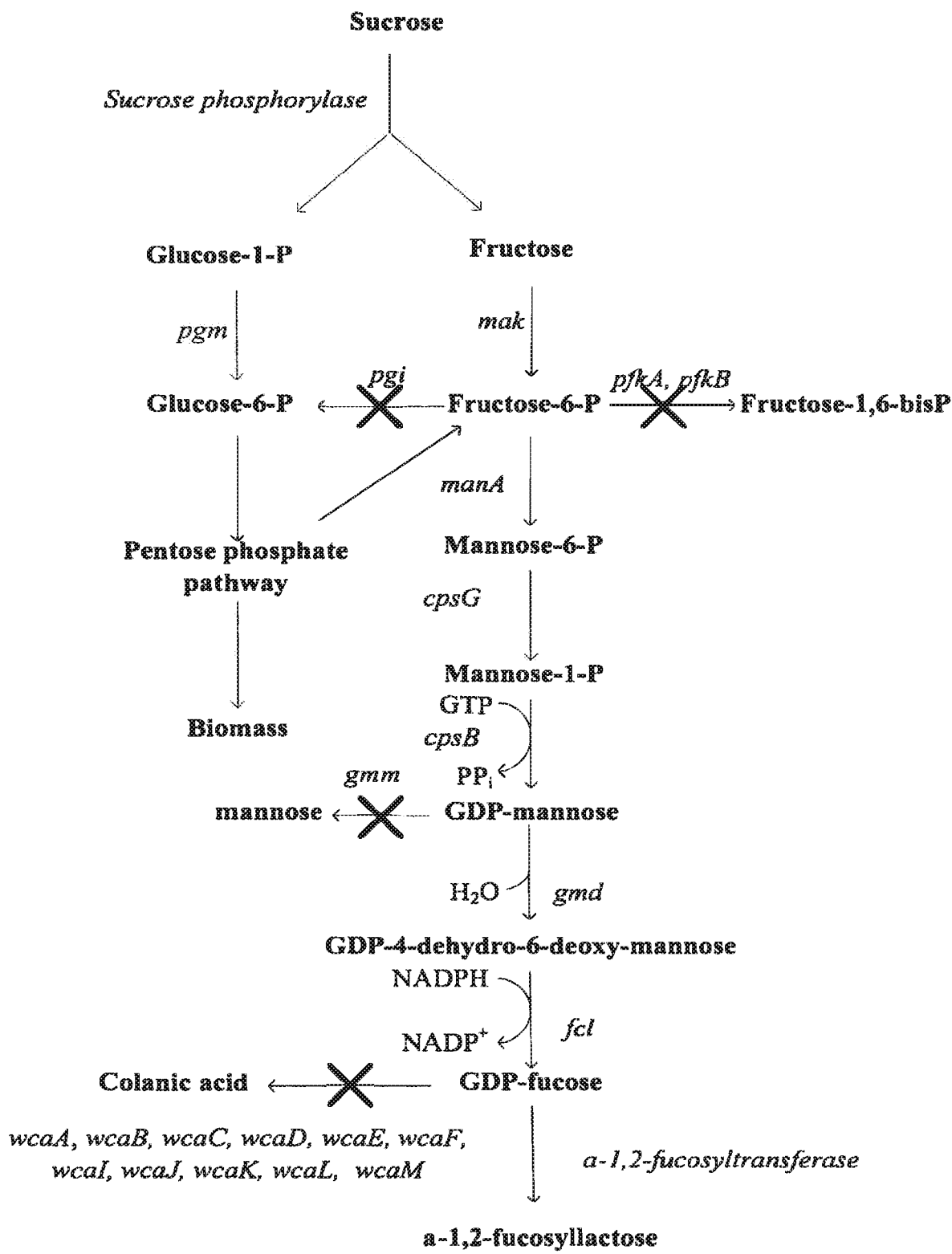
FIGS. 10A and 10B: Starting from base strain 5, fucosylated sugar derivates such as fucosyllactose and more specifically 1,2-fucosyllactose can be produced. The strain is modified to force the cell to produce frucose-6-phosphate which is an intermediate in the synthesis of GDP-fucose. Glucose or glucose-1-phosphate (if the starting enzyme is either a sucrase or a sucrose phosphorylase) is then fed to the central carbon metabolism via the pentose phosphate pathway.
Figure 10B:
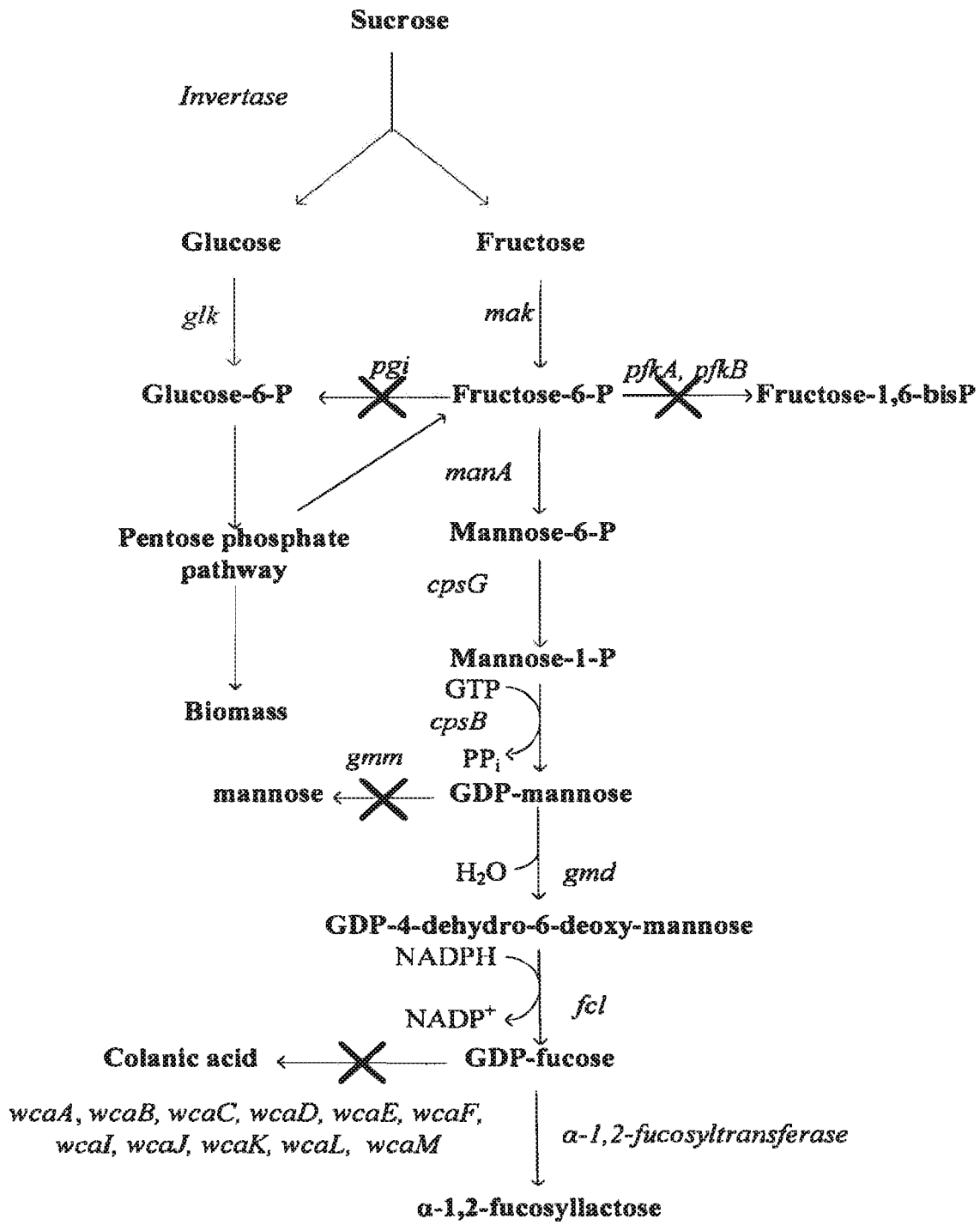

Starting from base strain 5, which accumulates fructose-6-phosphate, (described in Example 20 and Example 28) fucosylated sugar derivates such as fucosyllactose and more specifically 1,2-fucosyllactose can be produced. To this end, the strain is modified so that the cell is forced to produce fructose-6-phosphate which is a precursor of GDP-fucose. Glucose or glucose-1-phosphate (if the starting enzyme is either a sucrase or a sucrose phosphorylase) is then fed to the central carbon metabolism via the pentose phosphate pathway. FIGS. 10A and 10B show the route towards product and biomass and the needed knock outs to achieve this. To avoid loss of fructose-6-phosphate via glycolysis, pfkA, pfkB and pgi are knocked out. To avoid accumulation of pyruvate, the Entner Douderoff route is knocked out (edd and eda).

Because GDP-fucose is an intermediate of the colanic acid biosynthesis pathway, this pathway has to be modified. Genes from the colanic acid operon that can potentially reduce product yield are knocked out. These genes are gmm, wcaA, wcaBi, wcaC, wcaD, wcaE, wcaF, wcaI, wcaJ, wcaK, wcaL and/or, wcaM. The genes manA, cpsG, cpsB, gmd and, fcl (coding for Mannose-6-phosphate isomerase, phosphomannomutase, mannose-1-phosphate guanylyltransferase, GDP-mannose 4,6-dehydratase and GDP-fucose synthase, respectively) are enhanced in expression to increase the flux towards GDP-fucose. Either the colanic acid operon is knocked out completely, with the reintroduction of the needed genes that are overexpressed with an artificial promoter from a promoter library, or the operon is modified as such that the genes described above are knocked out one by one and the remaining genes in the operon are enhanced in expression by changing the promoter of the operon with an artificial constitutive promoter (23). Finally GDP-fucose is linked to lactose into α-1,2-fucosyllactose by a α-1,2-fucosyltransferase. The fucosyltransferases tested originate from *Helicobacter pylori*, *Bacteroides* sp., *Homo sapiens*, *Mus musculus*, *Bos taurus* and, *Dictyostelium discoideum*.

Example 16. Engineering *E. coli* Base Strain 3 (Galactose-1-P) and its Uses

By knocking-out genes coding for (a) phosphatase(s) (agp), UDP-glucose, galactose-1-P uridilyltransferase (galT), UDP-glucose-4-epimerase (galE) a mutant is constructed which accumulates galactose-1-P. By additionally overexpressing genes coding for galactokinase (galK) and/or galactose-1-epimerase (galM) the formation of galactose-1-P is enhanced (Table 10).

TABLE 10

Base strain galactose-1-phosphate

| | Reaction |
|---|---|
| Knock-out | |
| galT | Gal1P + UDP-Glucose ↔ UDP-Galactose + G1P |
| galE | UDP-Glucose ↔ UDP-Galactose |
| agp | Glucose-1-phosphate + H$_2$O → Pi + glucose |
| Knock-in | |
| galK | α-galactose + ATP → Gal1P + ADP |
| galM | β-galactose ↔ α-galactose |

Example 17. Engineering Base Strain 3 (Galactose-1P) and its Uses

By knocking-out genes coding for (a) phosphatase(s) (agp), UDP-glucose, galactose-1-P uridilyltransferase (galT), UDP-glucose-4-epimerase (galE) and by additionally overexpressing genes coding for galactokinase (galK) a mutant is constructed which accumulates galactose-1-P (Table 11).

TABLE 11

*E. coli* base strain galactose-1-phosphate

| | Reaction |
|---|---|
| Knock-out | |
| galT | Gal1P + UDP-Glucose ↔ UDP-Galactose + G1P |
| galE | UDP-Glucose ↔ UDP-Galactose |
| galK | α-galactose + ATP → Gal1P + ADP |
| galM | β-galactose ↔ α-galactose |
| agp | glucose-1-phosphate + H$_2$O → Pi + glucose |
| Knock-in | |
| galK | α-galactose + ATP → Gal1P + ADP |

To evaluate the potential of the metabolic engineering strategy, the galactose-1-phosphate concentration was determined for the wild type, *E. coli* MG1655 ΔgalET P22 galK, *E. coli* MG1655 ΔgalETKM Δagp P22 galK, *E. coli* MG1655 ΔgalET P22 galK, and *E. coli* MG1655 ΔgalETKM Δagp P22 galK+orotate (2 g/L) by growing these strains on a minimal medium containing lactose (15 g/L) as main carbon source. The results are depicted in Table 12.

TABLE 12

Galactose-1-P concentration of various *E. coli* mutants

| strain | Galactose-1-P (mg/L) |
|---|---|
| *E. coli* MG1655 | Not detectable |
| *E. coli* MG1655 ΔgalET P22 galK | 15.73 |
| *E. coli* MG1655 ΔgalETKM Δagp P22 galK | 69.08 |
| *E. coli* MG1655 ΔgalET P22 galK | 12.48 |
| *E. coli* MG1655 ΔgalETKM Δagp P22 galK + orotate (2 g/L) | 64.90 |

Example 18. Production of Glucose-6-Phosphate Using Sucrose Phosphorylase in *E. coli*

By introducing sucrose phosphorylase sucrose is split into glucose-1-P and fructose. By additionally knocking-out genes coding for (a) phosphatase(s) (agp), glucose 6-phosphate-1-dehydrogenase (zwt), phosphoglucose isomerase (pgi), glucose-1-phosphate adenylyltransferase (glgC) a mutant is constructed which accumulates glucose-6-P.

The KO mutants are chosen in such a way that the metabolism is split into two disconnected parts. However, all possible combinations of these genes result in increased supply. Instead of knocking-out these genes, this goal is also achieved by rendering them defective or by reducing their expression.

By metabolically engineering *E. coli* a base strain is constructed that is an efficient producer of specialty carbohydrates and their derivatives whose pathway starts from Glucose-6-P (Table 13).

TABLE 13

Base strain glucose-6-phosphate using a sucrose phosphorylase

| | Reaction |
|---|---|
| Knock-out | |
| zwf | G6P + NADP → 6PG + NADPH |
| agp | G1P + H$_2$O → Glc + Pi |
| glgC | G1P + ATP + H <–> ADP-glucose + PPi |
| pgi | G6P ↔ F6P |
| Knock-in | |
| Sucrose phosphorylase | Suc + Pi → G1P + Fru |
| pgm | G6P ↔ G1P |

Example 19. Production of Glucose-6-Phosphate Using Invertase in *E. coli*

By introducing sucrose hydrolase/invertase sucrose is split into glucose and fructose. By additionally knocking-out genes coding for (a) phosphatase(s) (agp), glucose 6-phosphate-1-dehydrogenase (zwt), phosphoglucose isomerase (pgi), glucose-1-phosphate adenylyltransferase (glgC), phosphoglucomutase (pgm) a mutant is constructed which accumulates Glucose-6-P (Table 14).

TABLE 14

Base strain glucose-6-phosphate using invertase in *E. coli*

| | Reaction |
|---|---|
| Knock-out | |
| zwf | G6P + NADP → 6PG + NADPH |
| agp | G1P + H$_2$O → Glu + Pi |
| pgi | G6P ↔ F6P |
| pgm | G6P ↔ G1P |
| Knock-in | |
| invertase | Suc + H$_2$O → Glc + Fru |

Example 20. Production of Fructose-6-Phosphate Using Invertase in *E. coli*

By introducing sucrose hydrolase/invertase sucrose is split into glucose and fructose. By additionally knocking-out genes coding for (a) phosphatase(s) (agp), phosphofructokinase (pfkA and pfkB), phosphoglucose isomerase (pp), glucose-1-phosphate adenylyltransferase (glgC), phosphoglucomutase (pgm) a mutant is constructed which accumulates fructose-6-phosphate (Table 15).

TABLE 15

Base strain fructose-6-phosphate

| | Reaction |
|---|---|
| Knock-out | |
| pfkA | F6P + ATP → FBP + ADP |
| pfkB | F6P + ATP → FBP + ADP |
| agp | G1P + H$_2$O → Glc + Pi |
| pgi | G6P ↔ F6P |
| pgm | G6P ↔ G1P |
| Knock-in | |
| invertase | Suc + H$_2$O → Glc + Fru |

Example 21. Production of β-Glucose-1-Phosphate Using Maltose Phophorylase in *E. coli*

By introducing maltose phosphorylase, maltose is split into β-D-glucose 1-phosphate and glucose. By additionally knocking-out genes coding for (a) phosphatase(s) (agp, yfbT), phosphoglucomutase (ycjU), maltose hydrolase (malPQ) a mutant is constructed which accumulates β-Glucose-1-P. The KO mutants are chosen in such a way that the metabolism is split into two disconnected parts. However, all possible combinations of these genes result in increased supply. Instead of knocking-out these genes, this goal is also achieved by rendering them defective or by reducing their expression (Table 16).

TABLE 16

Base strain β-D-Glucose-1-phosphate using maltose phophorylase in *E. coli*

| | Reaction |
|---|---|
| Knock-out | |
| malPQ | Maltose → glucose |
| yfbT | β-D-glucose 1-phosphate + H$_2$O → glucose + Pi |
| agp | Glucose-1-phosphate + H$_2$O → glucose + Pi |
| ycjU | β-D-glucose 1-phosphate <=> β-D-glucose-6-phosphate |
| Knock-in | |
| Maltose phosphorylase (MP) | Maltose + Pi → Glucose-1P + Glucose |

Example 22. Production of β-Glucose-1-Phosphate Using Trehalose Phophorylase in *E. coli*

By introducing trehalose phosphorylase trehalose is split into β-D-glucose 1-phosphate and glucose. By additionally knocking-out genes coding for (a) phosphatase(s) (agp, yfbT), phosphoglucomutase (ycjU), undesired native trehalose degrading enzymes (treABC, treC, treE, treF) a mutant is constructed which accumulates β-Glucose-1-phosphate (Table 17).

The KO mutants are chosen in such a way that the metabolism is split into two disconnected parts. However, all possible combinations of these genes result in increased productivity. Instead of knocking-out these genes, this goal is achieved by rendering them defective or by reducing their expression.

TABLE 17

Base strain β-D-Glucose-1-phosphate using trehalose phosphorylase in *E. coli*

| | Reaction |
|---|---|
| Knock-out | |
| treA | trehalose + H2O → 2 β-D-glucose |
| treC | trehalose 6-phosphate + H$_2$O → β-D-glucose-6-phosphate + β-D-glucose |
| treE | trehalose 6-phosphate + H$_2$O ↔ β-D-glucose-6-phosphate + β-D-glucose |
| treF | trehalose + H2O ↔ 2 β-D-glucose |
| yfbT | β-D-glucose 1-phosphate + H$_2$O → Glucose + Pi |
| agp | glucose 1-phosphate + H$_2$O → Glucose + Pi |
| ycjU | β-D-glucose 1-phosphate ↔ β-D-glucose-6-phosphate |

TABLE 17-continued

| Knock-in | |
|---|---|
| Trehalose Phosphorylase (TP) | Trehalose + Pi → β-D-Glucose-1P + Glucose |
| otsB | Trehalose-6-phosphate + H$_2$O → trehalose + Pi |

Example 23. Production of Kojibiose

Figure 16:
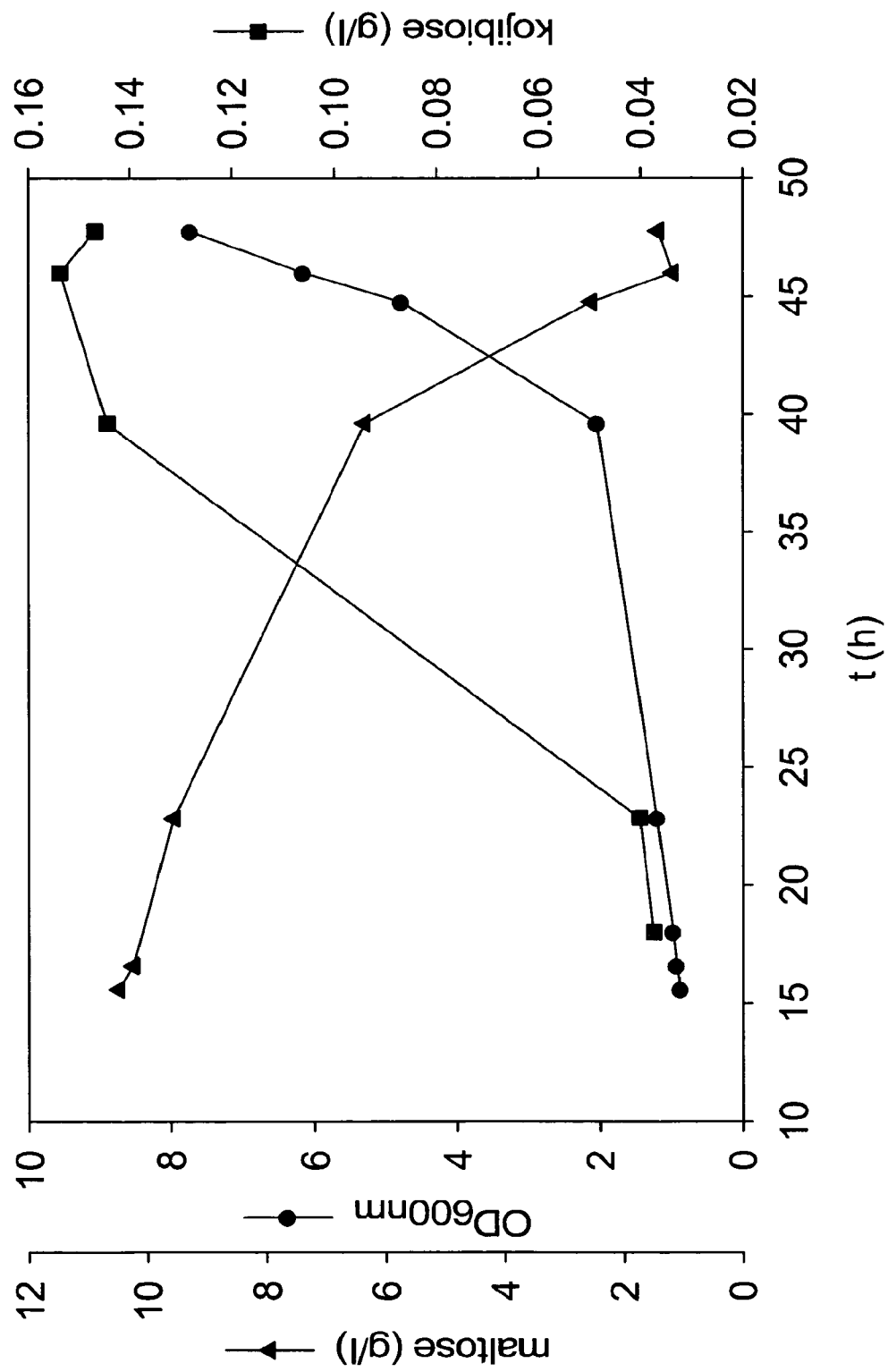
FIG. 16: Kojibiose, maltose and optical density evolution in time of a kojibiose producing strain with the genotype ΔlacZΔglgCΔagpΔptsGΔmalPQΔycjU pCXp22MPp22KP.

By additionally introducing kojibiose phosphorylase in a strain accumulating 13-D-glucose 1-phosphate and additionally knocking-out genes coding for glucokinase (gik) and, phosphotransferase system (ptsG) a mutant is constructed which produces kojibiose.
A fermentation is performed with an *E. coli* mutant strain (ΔlacZΔglgCΔagpΔptsGΔmalPQΔycjU pCXp22MPp22KP) using maltose and glucose as main carbon sources yielding kojibiose. (FIG. 16).

Example 24. Production of UDP Glucose from Sucrose Via a Sucrose Phosphorylase

By introducing sucrose phosphorylase (e.g., originating from *Bifidobacterium adolescentis*) sucrose is split into fructose and glucose-1-P. Starting from a glucose-1-phosphate accumulating strain (see examples above) and by additionally knocking-out genes coding UDP-glucose 4 epimerase (galE), UDP-glucose galactose-1-P uridilyltransferase (galT), 5'-nucleotidase/UDP-sugar hydrolase (ushA), UDP-glucose 6-dehydrogenase (ugd) a mutant is constructed which accumulates UDP-glucose by additionally overexpressing genes coding for UDP-glucose pyrophosphorylase (e.g. coming from *Bifidobacterium bifidum*) (Table 18).

TABLE 18

Base strain UDP-Glucose
from sucrose via a sucrose phosphorylase in *E. coli*

| Reaction | |
|---|---|
| Knock-out | |
| lacZ | Glu + Gal ↔ Lactose |
| galE | UDP-Glucose ↔ UDP-Galactose |
| galT | Gal1P + UDP-Glucose ↔ UDP-Galactose + G1P |
| ca | → colanic acid |
| ushA | a UDP-sugar + H$_2$O ↔ uridine-5'-phosphate + an α-D-aldose-1-phosphate + 2 H+ |
| ugd | 2 NAD+ + UDP-D-glucose + H$_2$O ↔ 2 NADH + UDP-D-glucuronate + 3 H+ |
| pgm | G1P ↔ G6P |
| glgC | G1P + ATP + H ↔ ADP-glucose + PPi |
| agp | G1P + H$_2$O → Glu + Pi |
| ptsG | Glc + PEP → G6P + Pyr |
| glk | Glc + ATP → G6P + ADP |
| Knock-in | |
| galU/F | G1P + UTP – UDP-Glucose + PPi |
| Sucrose phosphorylase | Suc → G1P + Fru |

Example 25. Production of UDP-Glucose in *E. coli* with a Sucrose-6-Phosphate Synthase Combined with Sucrose PTS By introducing Sucrose PTS (94) and Sucrose-6-phosphate synthase (69), sucrose is converted into fructose-6-phosphate and UDP-glucose. Starting from the strain described in example 4, without a sucrose phosphorylase, and by additionally knocking-out genes coding for (a) phosphatase(s) (agp), UDP-glucose 4 epimerase (galE), UDP-glucose galactose-1-P uridilyltransferase 5'-nucleotidase/UDP-sugar hydrolase (ushA), UDP-glucose 6-dehydrogenase (ugd) a mutant is constructed which accumulates UDP-glucose By additionally overexpressing genes coding for UDP-glucose pyrophosphorylase (*Bifidobacterium bifidum*) (Table 19).

TABLE 19

Base strain UDP-Glucose with
sucrose-6-phosphate synthase combined with sucrose PTS

| Reaction | |
|---|---|
| Knock-out | |
| galE | UDP-Glucose ↔ UDP-Galactose |
| galU/galF | UTP + G1P ↔ UDP-Glucose + PPi |
| galT | Gal1P + UDP-Glucose ↔ UDP-Galactose + G1P |
| ca | → colanic acid |
| ushA | a UDP-sugar + H$_2$O ↔ uridine-5'-phosphate + an α-D-aldose-1-phosphate + 2 H+ |
| ugd | 2 NAD+ + UDP-D-glucose + H$_2$O ↔ 2 NADH + UDP-D-glucuronate + 3 H+ |
| Knock-in | |
| Sucrose 6P synthase | UDP-glucose + D-fructose 6-phosphate → UDP + sucrose 6-phosphate |
| Sucrose PTS | Sucrose + PEP → sucrose-6-phosphate + Pyruvate |

Example 26. Production of UDP Galactose Via Galactokinase

By overexpressing genes coding for galactokinase (galK) and Galactose-1-phosphate uridylyltransferase (for example originating from *Bifidobacterium bifidum*) the formation of UDP-galactose is enhanced by additionally knocking-out genes coding for (a) phosphatase(s) (agp), UDP-glucose, galactose-1-P uridilyltransferase UDP-glucose-4-epimerase (galE) a mutant is constructed which accumulates galactose-1-P (Table 20).

TABLE 20

Base strain UDP-Galactose via galactokinase

| Reaction | |
|---|---|
| Knock-out | |
| galT | Gal1P + UDP-Glucose ↔ UDP-Galactose + G1P |
| galE | UDP-Glucose ↔ UDP-Galactose |
| galK | α-galactose + ATP → Gal1P + ADP |
| galM | β-galactose ↔ α-galactose |
| agp | glucose 1-phosphate + H2O → Pi + glucose |
| Knock-in | |
| galK | α-galactose + ATP → Gal1P + ADP |
| Galactose-1-phosphate uridylyltransferase | Gal1P + UTP → UDP-Galactose + PPi |

Example 27. Production of UDP Galactose Via Lactose Phosphorylase

By introducing lactose phosphorylase (20), lactose is split into glucose and galactose-1-P. By knocking-out genes coding for (a) phosphatase(s) (agp), UDP-glucose, galactose-1-P uridilyltransferase (galT), UDP-glucose-4-epimerase (galE) a mutant is constructed which accumulates galactose-1-P. By additionally overexpressing genes coding for Galactose-1-phosphate uridylyltransferase (for example coming from *Bifidobacterium bifidum*) the formation of UDP-galactose is enhanced (Table 21).

The KO mutants are chosen in such a way that the metabolism is split into two disconnected parts. However, all possible combinations of these genes result in increased productivity. Instead of knocking-out these genes, this goal is achieved by rendering them defective or by reducing their expression.

TABLE 21

Base strain UDP-Galactose via lactose phosphorylase

| | Reaction |
|---|---|
| Knock-out | |
| lacZ | Glu + Gal ↔ Lactose |
| galE | UDP-Glc <--> UDP-Gal |
| agp | G1P + H$_2$O → Glu + Pi |
| galT | UDP-Glc + Gal1P <--> UDP-Gal + G1P |
| Knock-in | |
| Lactose phosphorylase | Lactose + Pi → Gal1P + Glucose |
| Galactose-1-phosphate uridylyltransferase | Gal1P + UTP → UDP-Galactose + PPi |

Example 28. Fructose-6-Phosphate Accumulation in *E. coli*

The metabolism is split in order to accumulate fructose-6-phosphate. This is achieved by knocking out the genes coding for phosphoglucose isomerase and phosphofructokinase activity. In *E. coli* these activities are coded by the genes pgi, pfkA and pfkB. The growth rate of strains devoid of these activities is described in Table 22 for growth on glucose and sucrose. The growth rate of the wild type strain is somewhat affected when grown on sucrose after introduction of a sucrose phosphorylase in comparison with growth on glucose, however the introduction of pgi knock outs and pfkA and pfkB double mutations lead to significant reduction of growth rate, with the latter being extremely low (0.02 h−1) on glucose. Surprisingly the mutant strain ΔpgiΔpfkAΔpfkB has a similar growth rate to that of the Δpgi single mutant.

TABLE 22

Specific growth rates of the glycolysis knock out strains on a minimal medium with glucose and sucrose. In the strains grown on sucrose a plasmid coding for sucrose phosphorylase was introduced.

| Strain | Growth rate on glucose (h-1) | Growth rate on sucrose (h-1) |
|---|---|---|
| Wild type | 0.64 | 0.41 |
| Δpgi | 0.18 | 0.23 |
| ΔpfkAΔpfkB | 0.02 | n.d. |
| ΔpgiΔpfkAΔpfkB | 0.23 | 0.24 |

Figure 17:
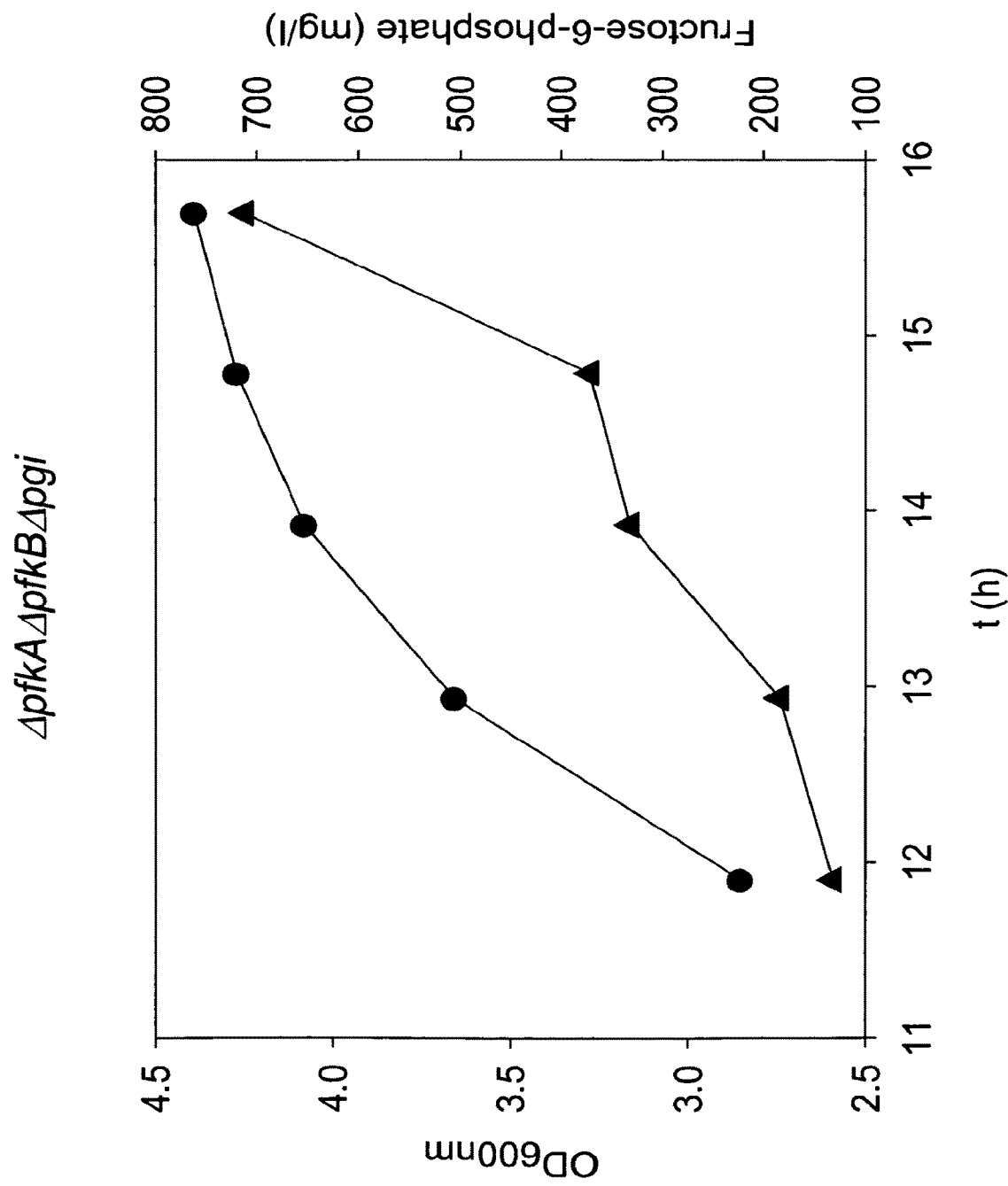
FIG. 17: Growth profile and F6P accumulation of a ΔpgiΔpfkAΔpfkB mutant strain in a sucrose based medium.

Only the ΔpgiΔpfkAΔpfkB mutant strain accumulated fructose-6-phosphate in the medium when grown on sucrose, the other strains did not indicate any F6P accumulation. The growth profile and F6P accumulation by this strain is shown FIG. 17.

Example 29. αGlucose-1-Phosphate Accumulation in *Saccharomyces cereviseae*

Because *Saccharomyces cereviseae* splits sucrose by nature, all alternative sucrose degrading reactions (invertases), which are coded by the genes SUC2, MAL32, MAL12, YJL216C, YGR287c, are knocked out. To avoid the assimilation of α-glucose-1-phosphate, the enzymes that convert this activated carbohydrate are rendered less functional or non-functional. These enzymes are phosphoglucomutase, coded by PGM1 and PGM2, and glucose-1-phosphatase, coded by INM1 and INM2. By introducing a sucrose phosphorylase (e.g., originating from *Bifidobacterium adolescentis*), similar to the split metabolism of *E. coli* (see example above). The *Saccharomyces cereviseae* metabolism is split into two parts resulting in the accumulation of αGlucose-1-phosphate.

Example 30. Cellobiose Production with *Saccharomyces cereviseae*

Because *Saccharomyces cereviseae* splits sucrose by nature, all alternative sucrose degrading reactions (invertases), which are coded by the genes SUC2, MAL32, MAL12, YJL216C, YGR287c, are knocked out. To avoid the assimilation of α-glucose-1-phosphate, the enzymes that convert this activated carbohydrate are rendered less functional or non-functional. These enzymes are phosphoglucomutase, coded by PGM1 and PGM2, and glucose-1-phosphatase, coded by INM1 and INM2. By introducing a sucrose phosphorylase (e.g., originating from *Bifidobacterium adolescentis*), similar to the split metabolism of *E. coli* (see example above). The *Saccharomyces cereviseae* metabolism is split into two parts resulting in the accumulation of αglucose-1-phosphate. By introducing a cellobiose phosphorylase gene originating from Cellulomonas uda, *Saccharomyces cereviseae* is able to produce cellobiose.

To avoid degradation of glucose, glucokinase activity, coded by GLK1 is knocked out as well. Because hexokinases in *Saccharomyces cereviseae* are not specific, these are replaced by a specific heterologous substrate specific hexokinase. Fructokinases originating from *E. coli* or *Bifidobacterium* adolescentis show lower activity for glucose and can replace the genes coding for the native hexokinases coded by HXK1 and HXK2.

Example 31. Fructose-6-Phosphate Accumulation in *Saccharomyces cereviseae* by Introducing a Sucrose Phosphorylase Because *Saccharomyces cereviseae* splits sucrose by nature, all alternative sucrose degrading reactions (invertases), which are coded by the genes SUC2, MAL32, MAL12, YJL216C, YGR287c, are knocked out. By introducing sucrose phophorylase from *Bifidobacterium adolescentis* sucrose is split into fructose and glucose-1-phosphate. To avoid the conversion of fructose-6-phosphate into biomass, the activity of the enzymes phosphoglucose isomerase and phosphofructokinase is reduced or eliminated by rendering the genes pgi1, PFK1 and PFK2 less functional or non-functional, respectively.

Example 32. Galactose-1-Phosphate Accumulation in *Saccharomyces cereviseae*

Galactose-1-phosphate is derived from the disaccharide lactose. Because *Saccharomyces* cereviseae does not split lactose by nature, a heterologous β-galactosidase (e.g. from *E. coli*) is introduced. This leads to the degradation of lactose to galactose and glucose. The goal is to increase the supply of galactose-1-phosphate to a biosynthetic pathway of a specialty carbohydrate. Therefore, galactose-1-phosphate may not be converted anymore into biomass, which is catalysed by UDP-glucose-hexose-1-phosphate uridylyltransferase, the aldose reductase. This is achieved by knocking out the genes coding for UDP-glucose-hexose-1-phosphate uridylyltransferase and aldose reductase, GAL7 and GRE3 respectively. To avoid degradation of said galactose-1-phosphate, the genes encoding for galactose-1-phosphatase are be knocked out. These are INM1 and INM2. A galactokinase is overexpressed in order to enhance the formation of galactose-1-phosphate from galactose.

Example 33. Glucose-6-Phosphate Accumulation in *Saccharomyces cereviseae* Via its Native Invertase To split the *Saccharomyces cereviseae* metabolism into two parts (to enhance the supply of glucose-6-phosphate so that it can be used as a building block for a specialty carbohydrate) glucose-6-phosphate dehydrogenase, phosphoglucomutase and phosphoglucose isomerase, which are coded by the genes ZWF1, PGM1 and PGM2, and PGI1, respectively, are knocked out. In such a strain sucrose is split in fructose and glucose by the native invertases and phosphorylated into fructose-6-phosphate and glucose-6-phosphate by the native hexokinases. Glucose-6-phosphate is then supplied to the specialty carbohydrate biosynthesis pathway and fructose-6-phosphate is converted into biomass.

Example 34. Glucose-6-Phosphate Accumulation in *Saccharomyces cereviseae* Via Sucrose Phosphorylase

*Saccharomyces cereviseae* is modified to produce glucose-6-phosphate from sucrose with a sucrose phosphorylase originating from *Bifidobacterium adolescentis*. Because sucrose phosphorylase competes for sucrose with invertase, the genes coding for invertase activity are knocked out. These genes are SUC2, MAL32, MAL12, YJL216C, and YGR287c. Glucose-1-phosphate is then further converted into glucose-6-phosphate with a phosphoglucomutase coded by PGM1 and PGM2. To avoid degradation of glucose-1-phosphate into glucose, glucose-1-phosphatase encoding genes are knocked out, coded by INM1 and INM2. The assimilation of this activated saccharide is further reduced by eliminating the UTP glucose-1-phosphate uridylyltransferase activity in the cell, by rendering the genes YHL012W and UGP1 less functional or non-functional. The fructose moiety is phosphorylated by the native hexokinases coded by HXK1 and HXK2 and converted into biomass.

Example 35. Enhanced UDP-Glucose Formation in *Saccharomyces cereviseae* Via Sucrose Synthase Because *Saccharomyces cereviseae* splits sucrose by nature, all alternative sucrose degrading reactions (invertases), which are coded by the genes SUC2, MAL32, MAL12, YJL216C, YGR287c, are knocked out. A sucrose synthase, e.g. originating from *Solanum tuberosum*, is introduced so that sucrose is split into UDP-Glucose and fructose. To avoid UDP-glucose conversion into biomass, the activity of the enzymes UDP-glucose diphosphorylase, UDP-glucose 4-epimerase, UDP-glucose-hexose-1-phosphate uridylyltransferase, UDP-glucose-glycogen glucosyltransferase, UDP-glucose-1,3-beta-D-glucan glucosyltransferase, UDP-glucose-glucosephosphate glucosyltransferase are rendered less functional or non-functional, these enzymes are coded by the genes UGP1 and YHL012W, GAL10, GAL7, GSY1 and GSY2, FEN1 and FKS1 and GSC2, and TPS1, respectively. The fructose moiety is phosphorylated by the native hexokinases coded by HXK1 and HXK2 and converted into biomass.

Example 36. Enhanced UDP-Glucose Formation in *Saccharomyces cereviseae* Via Sucrose Sucrose Phosphorylase In order to enhance UDP-glucose supply in *Saccharomyces cereviseae*, a strain as described in Example 29 is further modified by overexpressing the gene GAL7 which codes for a UTP-glucose-1-phosphate uridylyltransferase that catalyzes the conversion of α-glucose-1-phosphate into UDP-glucose.

Example 37. Enhanced UDP-Galactose Formation in *Saccharomyces cereviseae* Via β-Galactosidase In order to enhance UDP-galactose supply in *Saccharomyces cereviseae*, a strain as described in Example 32 is further modified by overexpressing a gene which codes for a UTP-galactose-1-phosphate uridylyltransferase (e.g. coming from *Bifidobacterium bifidum*) that catalyzes the conversion of α-galactose-1-phosphate into UDP-galactose.

Example 38. *Dictyostellium Discoideum* α1,2-Fucosyltransferase Activity

Introduction

Figure 18:
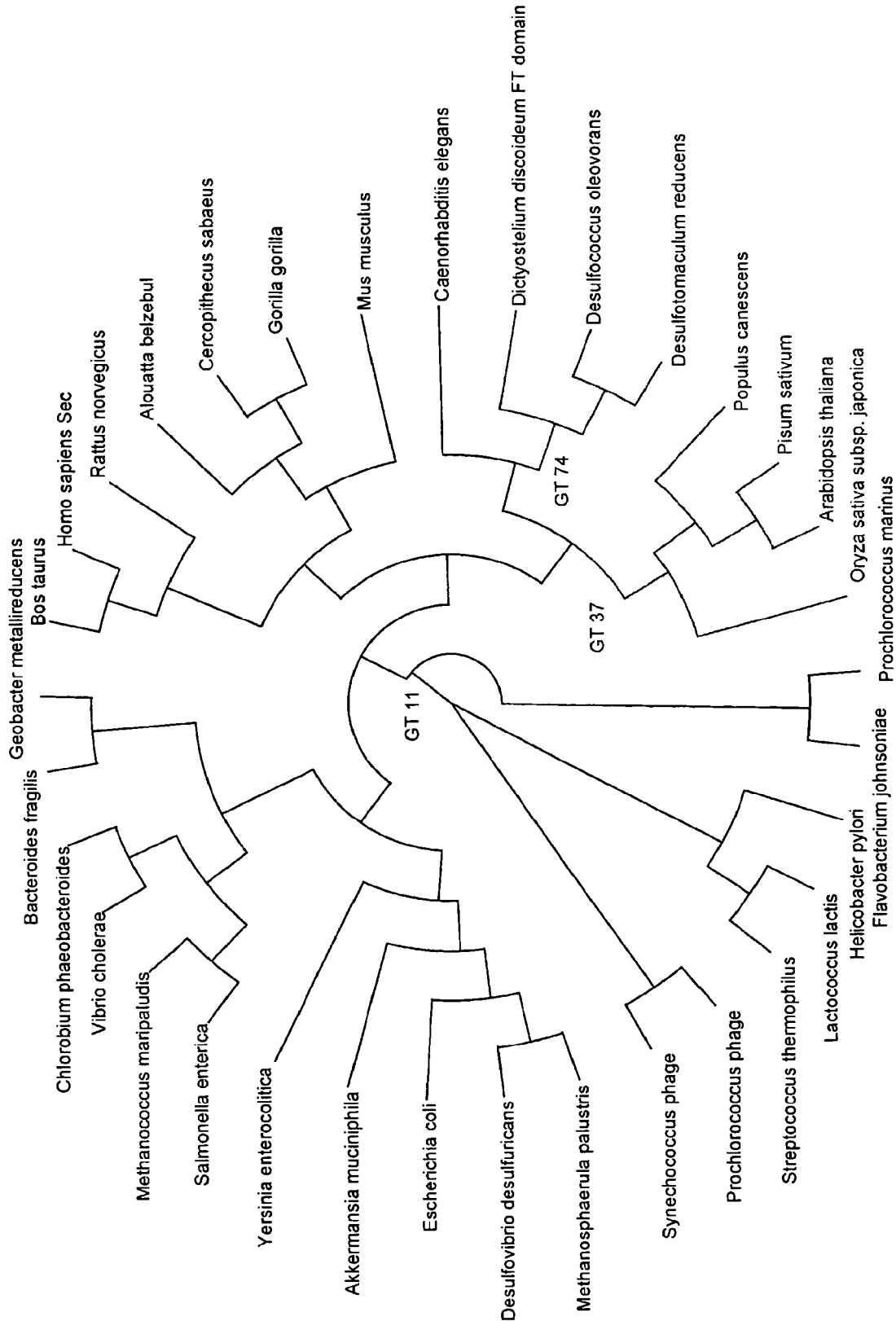
FIG. 18: Phylogenetic tree of the fucosyltransferases from the different glycosyltransferase families, the tree was constructed with MCoffee (58).

The *Dictyostelium discoideum* α1,2-fucosyltransferase (FT) is part of a rather new glycosyltransferase class. All known FT's belong to class GT11, while *D. discoideum* FT belongs to class GT74. Such an FT has, up to now, only been found in two other organisms namely *Desulfococcus oleovorans* and *Desulfotomaculum reducens*. The third class is GT37, which only contains plant FT's (FIG. 18). A clustalW and Tcoffee alignment indicated that the identity with *H. pylori* is only 9.7% and 15.5%, respectively. The conserved motives of GT11 are shown in FIG. 19 and these do not occur at all in the *Dictyostelium* protein (67). These domains differentiate for the fucosylation activity of the transferases. The first two motives are the same for α-1,2-fucosyltransferase and α-6-fucosyltransferase, while the third differentiates the enzymes from each other. α-1,3-fucosyltransferase contains two completely different conserved motives.

The *Dictyostelium discoideum* FT was however described to be only active on lacto-N-biose and not on galactose phenyl-β-galactoside, Galβ1-6-GlcNac, lactose, Galβ1-6Gal, Xyl, Glc, GlcNAc and GalNac (92).

Figure 20A:
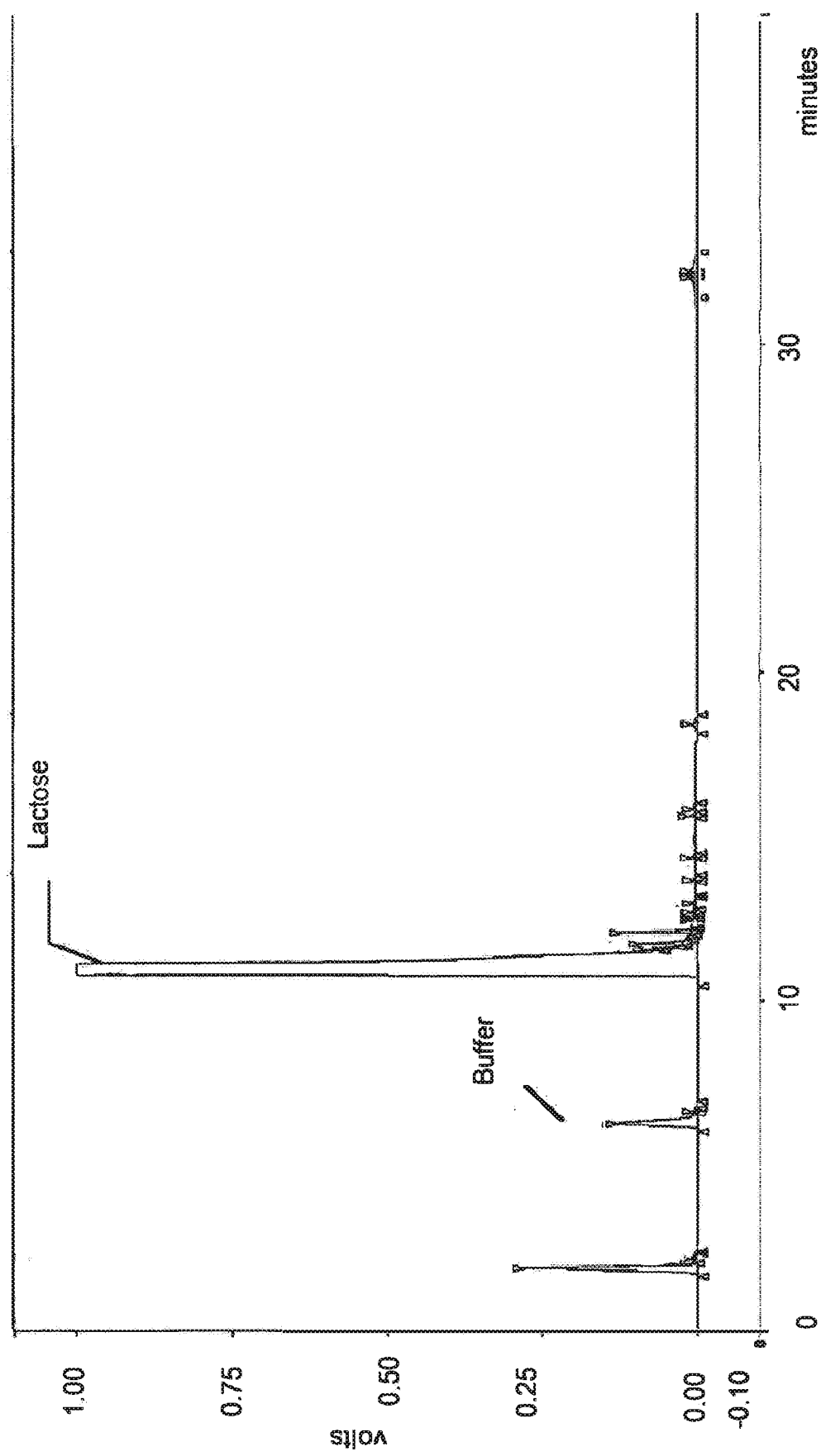
FIGS. 20A and 20B: LC-MS results of the fucosyltransferase assay with phenol red. The chromatogram in FIG. 20A is the blanc without GDP-fucose. The chromatogram in FIG. 20B is a sample of the *D. discoideum* fucosyltransferase assay; a 13.5 min a peak of 2FL appeared in the chromatogram.
Figure 20B:
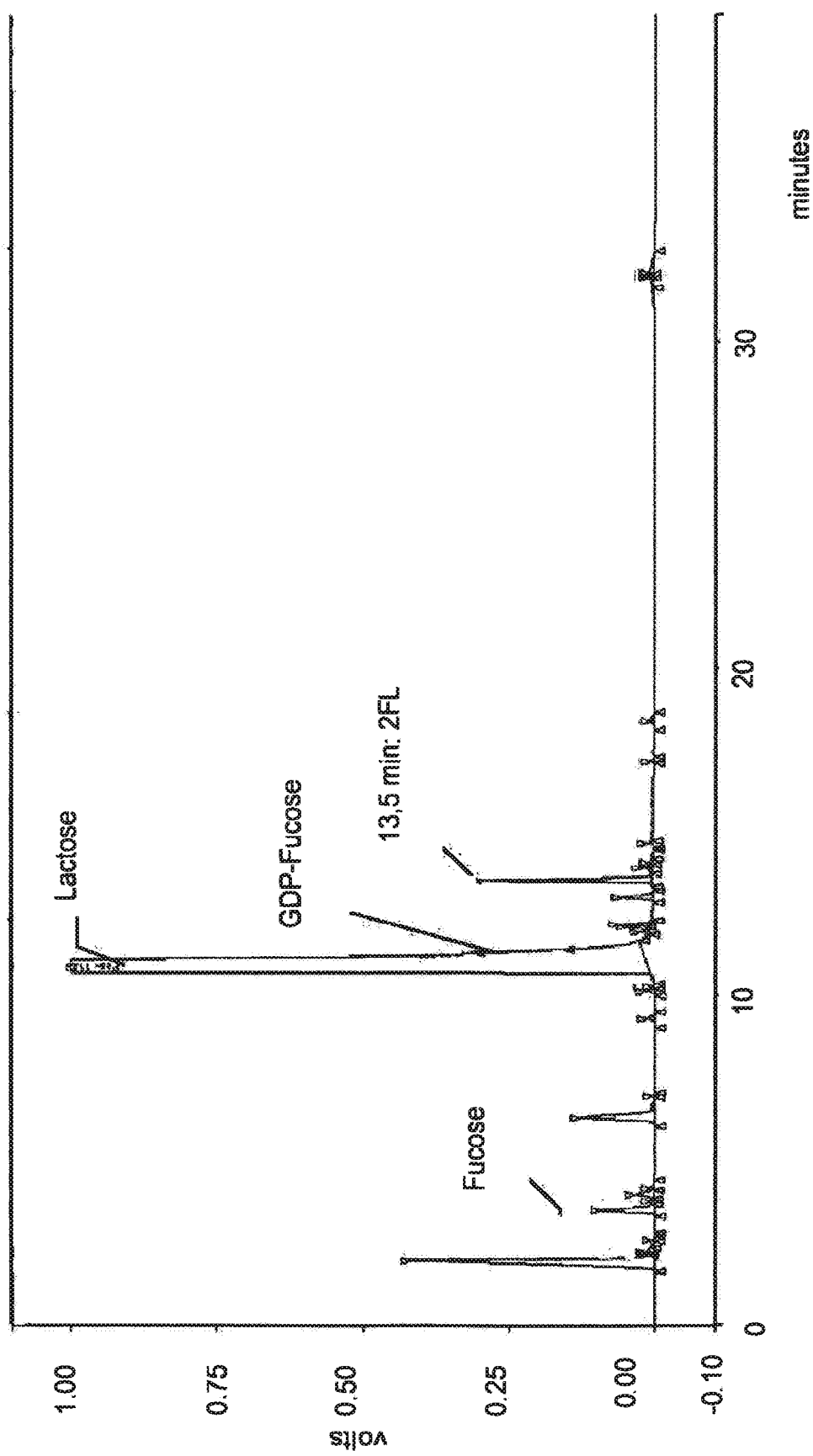

In FIGS. 20A and 20B a LC MSMS analysis of the *Dictyostellium discoideum* fucosyltransferase assay is shown. This assay showed surprisingly that this heterologous expressed fucosyltransferase is active with lactose as acceptor and GDP-fucose as fucose donor. The activity of this enzyme was 0.19±0.01 U/mg protein and was determined following the method of Persson and Palcic (68).

Figure 21:
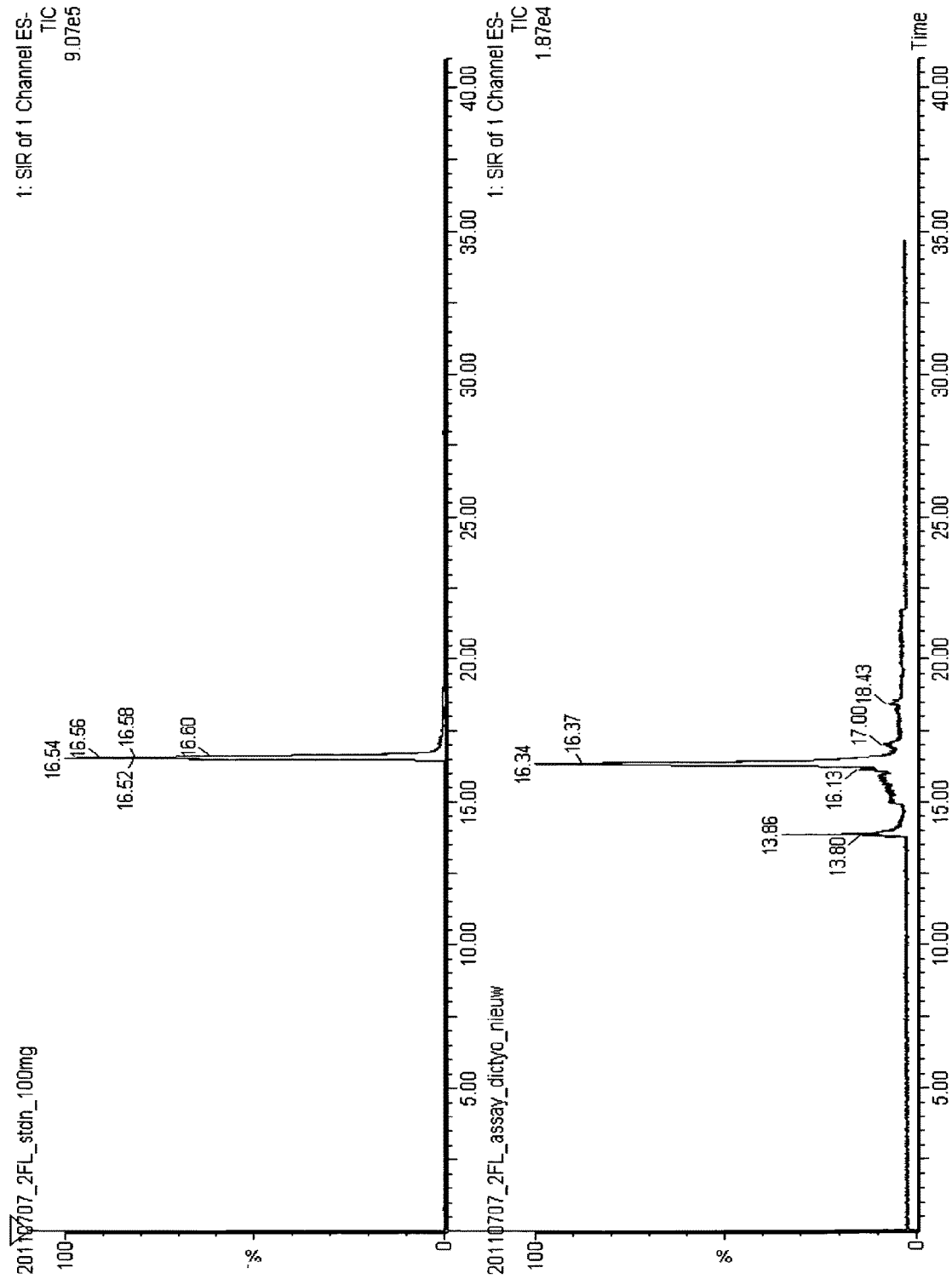
FIG. 21: 2-fucosyllactose LC MSMS analysis of the partial fucosyltransferase enzyme. The upper chromatogram shows a 100 mg/l standard of 2-fucosyllactose, the lower chromatogram shows the 2-fucosyllactose peak of the enzyme assay. In this analysis only the mass of 2-fucosyllactose was scanned with the mass spectrometer.

Because only half of the enzyme of *Dictyostelium discoideum* is responsible for its α1,2-fucosyltransferase activity, this part was cloned in a similar way to the complete enzyme, however with an additional start codon (coded by ATG) in front of the nucleotide sequence. This new enzyme was produced in a ΔlacZΔglgCΔmanAΔCA mutant strain and assayed for α1,2-fucosyltransferase activity with an LC MSMS. FIG. 21 shows clearly that this partial enzyme is still able to form 2-fucosyllactose from GDP-fucose and lactose.

Example 39. Myo-Inositol Production in *E. coli*

Starting from a base strain that accumulates glucose-6-phosphate, a myo-inositol producer is constructed by additionally introducing a gene coding for myo-inositol-1-phosphate synthase (INO1, originating from *Saccharomyces cerevisiae*) and nnyo-inositol-1(or 4)-monophosphatase (INM1 and INM2, originating from *Saccharomyces cerevisiae*).

Example 40. Lacto-N-Biose Production in *E. coli*

Starting from a base strain that accumulates galactose-1-phosphate, a Lacto-N-biose producer is constructed by additionally introducing a gene coding for lacto-N-biose phosphorylase (lnbp, *Bifidobacterium longum*). A fermentation is performed using lactose and N-acetylglucosamine as carbon sources. Degradation of N-acetylglucosamine is inhibited in the producer strain by eliminating any N-acetyl-D-glucosamine kinase activity (nagK) and N-acetylglucosamine PTS activity (nagE, ptsH, ptsI, manXYZ).

LIST OF ABBREVIATIONS USED IN THE TEXT

3KO a mutant strain in which the genes pgm, lacZ and glgC are knocked out
4KO a mutant strain in which the genes pgm, lacZ, glgC and agp are knocked out
6PG 6-phosphogluconate
BA *Bifidobacterium adolescentis*
BaSP a sucrose phosphorylase originating from *Bifidobacterium adolescentis*
CA Colanic acid operon defined by Stevenson et al. (86)
CDW Cell dry weight
CuCP *Cellulomonas uda* cellobiose phosphorylase
F6P Fructose-6-phosphate
FBP Fructose-1,6-bisphosphate
Fru Fructose
FT α1,2-Fucosyltransferase
G1P Glucose-1-phosphate
Gal1P Galactose-1-phosphate
Glc Glucose
Glu Glucose
KI Knock in
KO Knock out
KP Kojibiose phosphorylase
LA *Lactobacillus acidophilus*
LB Luria Bertani Broth
LM *Leuconostoc mesenteroides*
MP Maltose phosphorylase
P22 promoter 22 of the promoter library of De Mey et al (2007)
pCXp22 a plasmide that contains the P22 promoter according to Aerts et al (1)
PEP Phosphoenolpyruvate
Pi Inorganic phosphate
PPi Pyrophosphate
Pyr Pyruvate
rpm rotations per minute
SM *Streptococcus mutans*
SP Sucrose phosphorylase
Suc Sucrose
UDP-gal UDP-galactose
UDP-glc UDP-glucose
WT Wild type strain

REFERENCES

1. Aerts, D., T. Verhaeghe, M. De Mey, T. Desmet, and W. Soetaert. 2010. A constitutive expression system for high throughput screening. Engineering in Life Sciences 10:DOI: 10.1002/elsc.201000065.
2. Agrawal, N., P. V. N. Dasaradhi, A. Mohmmed, P. Malhotra, R. K. Bhatnagar, and S. K. Mukherjee. 2003. RNA Interference: Biology, Mechanism, and Applications. Microbiology and Molecular Biology Reviews 67:657-685.
3. Antoine, T., C. Bosso, A. Heyraud, and E. Samain. 2005. Large scale in vivo synthesis of globotriose and globotetraose by high cell density culture of metabolically engineered *Escherichia coli*. Biochimie 87:197-203.
4. Avihoo, A., I. Gabdank, M. Shapira, and D. Barash. 2007. In silico design of small RNA switches. IEEE Transactions on Nanobioscience 6:4-11.
5. Ayres, E. K., V. J. Thomson, G. Merino, D. Balderes, and D. H. Figurski. 1993. Precise deletions in large bacterial genomes by Vector-mediated Excision (VEX): The trfA gene of promiscuous plasmid RK2 is essential for replication in several gram-negative hosts. Journal of Molecular Biology 230:174-185.
6. Badet, B., P. Vermoote, P. Y. Haumont, F. Lederer, and F. Le Goffic. 1987. Glucosamine synthetase from *Escherichia coli*: purification, properties, and glutamine-utilizing site location. Biochemistry 26:1940-1948.
7. Balbás, P., M. Alexeyev, I. Shokolenko, F. Bolivar, and F. Valle. 1996. A pBRINT family of plasmids for integration of cloned DNA into the *Escherichia coli* chromosome. Gene 172:65-69.
8. Balbas, P., and G. Gosset. 2001. Chromosomal editing in *Escherichia coli*. Molecular Biotechnology 19:1-12.
9. Beauprez, J. 2010. Metabolic modelling and engineering of *Escherichia coli* for succinate production. PhD. Ghent University, Ghent.
10. Boles, E., W. Liebetrau, M. Hofmann, and F. K. Zimmermann. 1994. A family of hexosephosphate mutases in *Saccharomyces cerevisiae*. European Journal of Biochemistry 220:83-96.
11. Buchholz, A., R. Takors, and C. Wandrey. 2001. Quantification of Intracellular Metabolites in *Escherichia coli* K12 Using Liquid Chromatographic-Electrospray Ionization Tandem Mass Spectrometric Techniques. Analytical Biochemistry 295:129-137.
12. Burda, P., and M. Aebi. 1998. The ALG10 locus of *Saccharomyces cerevisiae* encodes the Î±-1,2 glucosyltransferase of the endoplasmic reticulum: the terminal glucose of the lipid-linked oligosaccharide is required for efficient N-linked glycosylation. Glycobiology 8:455-462.
13. Byun, S.-G., M.-D. Kim, W.-H. Lee, K.-J. Lee, N. Han, and J.-H. Seo. 2007. Production of GDP-I-fucose, 1-fucose donor for fucosyloligosaccharide synthesis, in recombinant *Escherichia coli*. Applied Microbiology and Biotechnology 74:768-775.
14. Cherepanov, P. P., and W. Wackernagel. 1995. Gene disruption in *Escherichia coli*: TcR and KmR cassettes with the option of Flp-catalyzed excision of the antibiotic-resistance determinant. Gene 158:9-14.

15. Chow, T., M. J. Goldenthal, J. D. Cohen, M. Hegde, and J. Marmur. 1983. Identification and physical characterization of yeast maltase structural genes. Molecular and General Genetics MGG 191:366-371.
16. Chow, T. H. C., P. Sollitti, and J. Marmur. 1989. Structure of the multigene family of <i>MAL</i> loci in <i>Saccharomyces<>. Molecular and General Genetics MGG 217:60-69.
17. Czar, M. J., J. C. Anderson, J. S. Bader, and J. Peccoud. 2009. Gene synthesis demystified. Trends in Biotechnology 27:63-72.
18. Daran, J. M., N. Dallies, D. Thines-Sempoux, V. Paquet, and J. Francois. 1995. Genetic and Biochemical Characterization of the UGP1 Gene Encoding the UDP-Glucose Pyrophosphorylase from *Saccharomyces cerevisiae*. European Journal of Biochemistry 233:520-530.
19. Datsenko, K. A., and B. L. Wanner. 2000. One-step inactivation of chromosomal genes in *Escherichia coli* K-12 using PCR products. Proceedings of the national academy of sciences of the United States of America 97:6640-6645.
20. De Groeve, M., V. Depreitere, T. Desmet, and W. Soetaert. 2009. Enzymatic production of α-D-galactose 1-phosphate by lactose phosphorolysis. Biotechnology Letters 31:1873-1877.
21. De Mey, M. 2007. Metabolic modelling and engineering of *Escherichia coli* to minimize acetate formation in recombinant DNA fermentation processes. Ghent University, Ghent.
22. De Mey, M., A. Cerdobbel, K. Van Nieuland, J. Maertens, W. Soetaert, and E. J. Vandamme. 2006. Promoter Engineering: A Useful Tool for Fine Tunning Gene Expression in *Escherichia coli*. Department of Biochemical and Microbial Technology, Ghent University.
23. De Mey, M., J. Maertens, G. J. Lequeux, W. K. Soetaert, and E. J. Vandamme. 2007. Construction and model-based analysis of a promoter library for *E. coli*: an indispensable tool for metabolic engineering. BMC Biotechnology 7:34-48.
24. De Virgilio, C., N. BÜRckert, W. Bell, P. JenÖ, T. Boller, and A. Wiemken. 1993. Disruption of TPS2, the gene encoding the 100-kDa subunit of the trehalose-6-phosphate synthase/phosphatase complex in *Saccharomyces cerevisiae*, causes accumulation of trehalose-6-phosphate and loss of trehalose-6-phosphate phosphatase activity. European Journal of Biochemistry 212:315-323.
25. Dedhia, N. N., T. Hottiger, and J. E. Bailey. 1994. Overproduction of glycogen in *Escherichia coli* blocked in the acetate pathway improves cell growth. Biotechnology and Bioengineering 44:132-139.
26. Dickinson, J. R. 1991. Biochemical and genetic studies on the function of, and relationship between, the PGI1- and CDC30-encoded phosphoglucose isomerases in *Saccharomyces cerevisiae*. Journal of General Microbiology 137:765-770.
27. Dippel, R., and W. Boos. 2005. The Maltodextrin System of *Escherichia coli*: Metabolism and Transport. J. Bacteriol. 187:8322-8331.
28. Edwards, C. J., D. J. Innes, D. M. Burns, and I. R. Beacham. 1993. UDP-sugar hydrolase enzymes in *Salmonella enterica* and *Escherichia coli*: silent alleles of ushA in related strains of group I *Salmonella* isolates, and of ushB in wild type and K12 strains of *Escherichia coli* indicate recent and early silencing events, respectively I. Fems Microbiology Letters 114:293-298.
29. Egan, S. E., R. Fliege, S. Tong, A. Shibata, R. E. Wolf, Jr., and T. Conway. 1992. Molecular characterization of the Entner-Doudoroff pathway in *Escherichia coli*: sequence analysis and localization of promoters for the edd-eda operon. Journal of Bacteriology 174:4638-4646.
30. Farkas, I., T. A. Hardy, A. A. DePaoli-Roach, and P. J. Roach. 1990. Isolation of the GSY1 gene encoding yeast glycogen synthase and evidence for the existence of a second gene. Journal of Biological Chemistry 265:20879-20886.
31. Farkas, I., T. A. Hardy, M. G. Goebl, and P. J. Roach. 1991. Two glycogen synthase isoforms in *Saccharomyces cerevisiae* are coded by distinct genes that are differentially controlled. Journal of Biological Chemistry 266:15602-15607.
32. Flores, N., L. Leal, J. C. Sigala, R. de Anda, A. Escalante, A. Martinez, O. T. Ramirez, G. Gosset, and F. Bolivar. 2007. Growth recovery on glucose under aerobic conditions of an *Escherichia coli* strain carrying a phosphoenolpyruvate: Carbohydrate phosphotransferase system deletion by inactivating arcA and overexpressing the genes coding for glucokinase and galactose permease. Journal of Molecular Microbiology and Biotechnology 13:105-116.
33. Goedl, C., A. Schwarz, A. Minani, and B. Nidetzky. 2007. Recombinant sucrose phosphorylase from *Leuconostoc mesenteroides*: Characterization, kinetic studies of transglucosylation, and application of immobilised enzyme for production of α-D-glucose 1-phosphate. Journal of Biotechnology 129:77-86.
34. Gorsich, S., B. Dien, N. Nichols, P. Slininger, Z. Liu, and C. Skory. 2006. Tolerance to furfural-induced stress is associated with pentose phosphate pathway genes ZWF1, GND1, RPE1, and TKL1 in *Saccharomyces cerevisiae*. Applied Microbiology and Biotechnology 71:339-349.
35. Gräslund, S., P. Nordlund, J. Weigelt, B. M. Hallberg, J. Bray, O. Gileadi, S. Knapp, U. Oppermann, C. Arrowsmith, R. Hui, J. Ming, S. dhe-Paganon, H.-w. Park, S. *Alexei*, A. Yee, A. Edwards, R. Vincentelli, C. Cambillau, R. Kim, S.-H. Kim, Z. Rao, Y. Shi, T. C. Terwilliger, C.-Y. Kim, L.-W. Hung, G. S. Waldo, Y. Peleg, S. Albeck, T. Unger, O. Dym, J. Prilusky, J. L. Sussman, R. C. Stevens, S. A. Lesley, I. A. Wilson, A. Joachimiak, F. Collart, I. Dementieva, M. I. Donnelly, W. H. Eschenfeldt, Y. Kim, L. Stols, R. Wu, M. Zhou, S. K. Burley, J. S. Emtage, J. M. Sauder, D. Thompson, K. Bain, J. Luz, T. Gheyi, F. Zhang, S. Atwell, S. C. Almo, J. B. Bonanno, A. Fiser, S. Swaminathan, F. W. Studier, M. R. Chance, A. Sali, T. B. Acton, R. Xiao, L. Zhao, L. C. Ma, J. F. Hunt, L. Tong, K. Cunningham, M. Inouye, S. Anderson, H. Janjua, R. Shastry, C. K. Ho, D. Wang, H. Wang, M. Jiang, G. T. Montelione, D. I. Stuart, R. J. Owens, S. Daenke, A. Schütz, U. Heinemann, S. Yokoyama, K. Büssow, and K. C. Gunsalus. 2008. Protein production and purification. Nature Methods 5:135-146.
36. Hashimoto, H., A. Sakakibara, M. Yamasaki, and K. Yoda. 1997. *Saccharomyces cerevisiae* VIG9 Encodes GDP-mannose Pyrophosphorylase, Which Is Essential for Protein Glycosylation. Journal of Biological Chemistry 272:16308-16314.
37. Hebert, C. G., J. J. Valdes, and W. E. Bentley. 2008. Beyond silencing—engineering applications of RNA interference and antisense technology for altering cellular phenotype. Current opinion in biotechnology 19:500-505.
38. Heillisch, J., R. G. Ritzel, R. C. von Borstel, A. Aguilera, R. Rodicio, and F. K. Zimmermann. 1989. The phosphofructokinase genes of yeast evolved from two duplication events. Gene 78:309-321.
39. Heinisch, J. 1986. Isolation and characterization of the two structural genes coding for phosphofructokinase in yeast. Molecular and General Genetics MGG 202:75-82.

40. Hoang, T. T., R. R. Karkhoff-Schweizer, A. J. Kutchma, and H. P. Schweizer. 1998. A broad-host-range Flp-FRT recombination system for site-specific excision of chromosomally-located DNA sequences: application for isolation of unmarked *Pseudomonas aeruginosa* mutants. Gene 212:77-86.
41. Ishihara, S., A. Hirata, S. Nogami, A. Beauvais, J.-P. Latge, and Y. Ohya. 2007. Homologous Subunits of 1,3-Beta-Glucan Synthase Are Important for Spore Wall Assembly in *Saccharomyces cerevisiae*. Eukaryotic Cell 6:143-156.
42. Keasling, J. D. 1999. Gene-expression tools for the metabolic engineering of bacteria. Trends in Biotechnology 17:452-460.
43. Kiino, D. R., R. Licudine, K. Wilt, D. H. Yang, and L. B. Rothman-Denes. 1993. A cytoplasmic protein, NfrC, is required for bacteriophage N4 adsorption. Journal of Bacteriology 175:7074-7080.
44. Kim, C., S. Song, and C. Park. 1997. The D-allose operon of *Escherichia coli* K-12. J. Bacteriol. 179:7631-7637.
45. Kogure, T., N. Wakisaka, H. Takaku, and M. Takagi. 2007. Efficient production of 2-deoxy-scyllo-inosose from D-glucose by metabolically engineered recombinant *Escherichia coli*. Journal of Biotechnology 129:502-509.
46. Kornberg, H. L. 2001. Routes for fructose utilization by *Escherichia coli*. Journal of Molecular Microbiology and Biotechnology 3:355-359.
47. Kristensen, C. S., L. Eberl, J. M. Sanchez-Romero, M. Givskov, S. Molin, and V. De Lorenzo. 1995. Site-specific deletions of chromosomally located DNA segments with the multimer resolution system of broad-host-range plasmid RP4. Journal of Bacteriology 177:52-58.
48. Kuznetsova, E., M. Proudfoot, C. F. Gonzalez, G. Brown, M. V. Omelchenko, I. Borozan, L. Carmel, Y. I. Wolf, H. Mori, A. V. Savchenko, C. H. Arrowsmith, E. V. Koonin, A. M. Edwards, and A. F. Yakunin. 2006. Genome-wide Analysis of Substrate Specificities of the *Escherichia coli* Haloacid Dehalogenase-like Phosphatase Family. Journal of Biological Chemistry 281:36149-36161.
49. Lasserre, J.-P., E. Beyne, S. Pyndiah, D. Lapaillerie, S. Claverol, and M. Bonneu. 2006. A complexomic study of *Escherichia coli* using two-dimensional blue native/SDS polyacrylamide gel electrophoresis. Electrophoresis 27:3306-3321.
50. LluII, D., E. Garcia, and R. Lopez. 2001. Tts, a Processive b-Glucosyltransferase of *Streptococcus pneumoniae*, Directs the Synthesis of the Branched Type 37 Capsular Polysaccharide in Pneumococcus and Other Gram-positive Species. Journal of Biological Chemistry 276:21053-21061.
51. Lopez, F., M. Leube, R. Gil-Mascarell, J. P. Navarro-Aviño, and R. Serrano. 1999. The yeast inositol monophosphatase is a lithium- and sodium-sensitive enzyme encoded by a non-essential gene pair. Molecular Microbiology 31:1255-1264.
52. Maitra, U. S., and H. Ankel. 1973. The intermediate in the uridine diphosphate galactose 4-epimerase reaction: Resolution of an apparent ambiguity. Journal of Biological Chemistry 248:1477-1479.
53. Markovitz, A., R. J. Sydiskis, and M. M. Lieberman. 1967. Genetic and biochemical studies on mannose-negative mutants that are deficient in phosphomannose isomerase in *Escherichia coli* K-12. Journal of Bacteriology 94:1492-1496.
54. Marolda, C., L., and M. Valvano, A. 1996. The GalF protein of *Escherichia coli* is not a UDP-glucose pyrophosphorylase but interacts with the GalU protein possibly to regulate cellular levels of UDP-glucose. Molecular Microbiology 22:827-840.
55. Marquardt, J. L., E. D. Brown, C. T. Walsh, and K. S. Anderson. 1993. Isolation and structural elucidation of a tetrahedral intermediate in the UDP-N-acetylglucosamine enolpyruvoyl transferase enzymic pathway. Journal of the American Chemical Society 115:10398-10399.
56. Mazur, P., N. Morin, W. Baginsky, M. el-Sherbeini, J. Clemas, J. Nielsen, and F. Foor. 1995. Differential expression and function of two homologous subunits of yeast 1,3-beta-D-glucan synthase. Mol. Cell. Biol. 15:5671-5681.
57. Meijer, W. H., I. J. van der Klei, M. Veenhuis, and J. A. K. W. Kiel. 2007. ATG Genes Involved in Non-Selective Autophagy are Conserved from Yeast to Man, but the Selective Cvt and Pexophagy Pathways also Require Organism-Specific Genes. Autophagy 3:106-116.
58. Moretti, S., F. Armougom, I. M. Wallace, D. G. Higgins, C. V. Jongeneel, and C. Notredame. 2007. The M-Coffee web server: a meta-method for computing multiple sequence alignments by combining alternative alignment methods. Nucleic Acids Research 35:W645-W648.
59. Mu, J., C. Cheng, and P. J. Roach. 1996. Initiation of Glycogen Synthesis in Yeast. Journal of Biological Chemistry 271:26554-26560.
60. Müller, S., F. K. Zimmermann, and E. Boles. 1997. Mutant studies of phosphofructo-2-kinases do not reveal an essential role of fructose-2, 6-bisphosphate in the regulation of carbon fluxes in yeast cells. Microbiology 143:3055-3061.
61. Murray, M., and M. L. Greenberg. 2000. Expression of yeast INM1 encoding inositol monophosphatase is regulated by inositol, carbon source and growth stage and is decreased by lithium and valproate. Molecular Microbiology 36:651-661.
62. Nassau, P. M., S. L. Martin, R. E. Brown, A. Weston, D. Monsey, M. R. McNeil, and K. Duncan. 1996. Galactofuranose biosynthesis in *Escherichia coli* K-12: identification and cloning of UDP-galactopyranose mutase. Journal Of Bacteriology 178:1047-1052.
63. Neidhardt, F. C. 1996. *Escherichia coli* and *Salmonella*. Cellular and Molecular Biology. ASM Press, Washington, D.C.
64. Nogae, I., and M. Johnston. 1990. Isolation and characterization of the ZWF1 gene of *Saccharomyces cerevisiae*, encoding glucose-6-phosphate dehydrogenase. Gene 96:161-169.
65. Novotny, M. J., J. Reizer, F. Esch, and M. H. Saier, Jr. 1984. Purification and properties of D-mannitol-1-phosphate dehydrogenase and D-glucitol-6-phosphate dehydrogenase from *Escherichia coli*. J. Bacteriol. 159:986-990.
66. Oh, C.-S., D. A. Toke, S. Mandala, and C. E. Martin. 1997. ELO2 and ELO3, Homologues of the *Saccharomyces cerevisiae* ELO1 Gene, Function in Fatty Acid Elongation and Are Required for Sphingolipid Formation. Journal of Biological Chemistry 272:17376-17384.
67. Oriol, R., R. Mollicone, A. Cailleau, L. Balanzino, and C. Breton. 1999. Divergent evolution of fucosyltransferase genes from vertebrates, invertebrates, and bacteria. Glycobiology 9:323-334.
68. Persson, M., and M. M. Palcic. 2008. A high-throughput pH indicator assay for screening glycosyltransferase saturation mutagenesis libraries. Analytical Biochemistry 378:1-7.
69. Porchia, A. C., and G. L. Salerno. 1996. Sucrose biosynthesis in a prokaryotic organism: Presence of two 69. sucrose-phosphate synthases in *Anabaena* with remarkable differences compared with the plant-enzymes. Proceedings of the National Academy of Sciences 93:13600-13604.
70. Priem, B., M. Gilbert, W. W. Wakarchuk, A. Heyraud, and E. Samain. 2002. A new fermentation process allows large-scale production of human milk oligosaccharides by metabolically engineered bacteria. Glycobiology 12:235-240.
71. Ramakrishnan, B., and P. K. Qasba. 2001. Crystal structure of lactose synthase reveals a large conformational change in its catalytic component, the [beta]1,4-galactosyltransferase-1. Journal of Molecular Biology 310:205-218.
72. Ramakrishnan, B., P. S. Shah, and P. K. Qasba. 2001. α-Lactalbumin (LA) Stimulates Milk b-1,4-Galactosyltransferase I (b4Gal-T1) to Transfer Glucose from UDP-glucose to N-Acetylglucosamine. Journal of Biological Chemistry 276:37665-37671.
73. Rasmussen, L., H. Sperling-Petersen, and K. Mortensen. 2007. Hitting bacteria at the heart of the central dogma: sequence-specific inhibition. Microbial Cell Factories 6:24.
74. Rider, M. H., L. Bertrand, D. Vertommen, P. A. Michels, G. G. Rousseau, and L. Hue. 2004. 6-phosphofructo-2-kinase/fructose-2,6-bisphosphatase: Head-to-head with a bifunctional enzyme that controls glycolysis. Biochemical Journal 381:561-579.
75. Riitta, V., and V. Martti. 1995. Comparison of the phenotypes of the IpxA and IpxD mutants of *Escherichia coli*. FEMS Microbiology Letters 134:227-232.
76. Rodriguez, A., T. De La Cera, P. Herrero, and F. Moreno. 2001. The hexokinase 2 protein regulates the expression of the GLK1, HXK1 and HXK2 genes of *Saccharomyces cerevisiae*. Biochem. J. 355:625-631.
77. Ruffing, A., and R. R. Chen. 2006. Metabolic engineering of microbes for oligosaccharide and polysaccharide synthesis. Microbial Cell Factories 5.
78. Rush, J. S., P. D. Rick, and C. J. Waechter. 1997. Polyisoprenyl phosphate specificity of UDP-GlcNAc:undecaprenyl phosphate N-acetylglucosaminyl 1-P transferase from *E. coli*. Glycobiology 7:315-322.
79. Sauer, B. 1987. Functional expression of the cre-lox site-specific recombination system in the yeast *Saccharomyces cerevisiae*. Molecular and Cellular Biology 7:2087-2096.
80. Schweizer, H. P. 2003. Applications of the *Saccharomyces cerevisiae* Flp-FRT system in bacterial genetics. Journal of Molecular Microbiology and Biotechnology 5:67-77.
81. Segawa, T., and T. Fukasawa. 1979. The enzymes of the galactose cluster in *Saccharomyces cerevisiae*. Purification and characterization of galactose-1-phosphate uridylyltransferase. Journal of Biological Chemistry 254:10707-10709.
82. Sinnott, M. L. 1978. Ions, ion-pairs and catalysis by the lacZ b-galactosidase of *Escherichia coli*. FEBS Letters 94:1-9.
83. Smith, D. J., A. Proudfoot, L. Friedli, L. S. Klig, G. Paravicini, and M. A. Payton. 1992. PM140, an intron-containing gene required for early steps in yeast mannosylation. Mol. Cell. Biol. 12:2924-2930.
84. Stagljar, I., S. te Heesen, and M. Aebi. 1994. New phenotype of mutations deficient in glucosylation of the lipid-linked oligosaccharide: cloning of the ALG8 locus. Proceedings of the National Academy of Sciences 91:5977-5981.
85. Sternberg, N., D. Hamilton, and R. Hoess. 1981. Bacteriophage P1 site-specific recombination: II. Recombination between loxP and the bacterial chromosome. Journal of Molecular Biology 150:487-507.
86. Stevenson, G., K. Andrianopoulos, M. Hobbs, and P. R. Reeves. 1996. Organization of the *Escherichia coli* K-12 gene cluster responsible for production of the extracellular polysaccharide colanic acid. Journal of Bacteriology 178:4885-4893.
87. Stevenson, G., B. Neal, D. Liu, M. Hobbs, N. H. Packer, M. Batley, J. W. Redmond, L. Lindquist, and P. Reeves. 1994. Structure of the O antigen of *Escherichia coli* K-12 and the sequence of its rfb gene cluster. Journal of Bacteriology 176:4144-4156.
88. Tallon, R., P. Bressollier, and M. C. Urdaci. 2003. Isolation and characterization of two exopolysaccharides produced by *Lactobacillus plantarum* EP56. Research in Microbiology 154:705-712.
89. Taussig, R., and M. Carlson. 1983. Nucleotide sequence of The yeast SUC2 gene for invertase. Nucleic Acids Research 11:1943-1954.
90. Teste, M.-A., J. M. Francois, and J.-L. Parrou. 2010. Characterization of a New Multigene Family Encoding Isomaltases in the Yeast *Saccharomyces cerevisiae*, the IMA Family. Journal of Biological Chemistry 285:26815-26824.
91. Thoden, J. B., and H. M. Holden. 2005. The Molecular Architecture of Galactose Mutarotase/UDP-Galactose 4-Epimerase from *Saccharomyces cerevisiae*. Journal of Biological Chemistry 280:21900-21907.
92. Trinchera, M., and S. Bozzaro. 1996. *Dictyostelium* cytosolic fucosyltransferase synthesizes H type 1 trisaccharide in vitro. FEBS Letters 395:68-72.
93. Tsuda, M. 1998. Use of a transposon-encoded site-specific resolution system for construction of large and defined deletion mutations in bacterial chromosome. Gene 207:33-41.
94. Wang, J., E. D. Gilles, J. W. Lengeler, and K. Jahreis. 2001. Modeling of inducer exclusion and catabolite repression based on a PTS-dependent sucrose and non-PTS-dependent glycerol transport systems in *Escherichia coli* K-12 and its experimental verification. Journal of Biotechnology 92:133-158.
95. Watzele, G., and W. Tanner. 1989. Cloning of the glutamine:fructose-6-phosphate amidotransferase gene from yeast. Pheromonal regulation of its transcription. Journal of Biological Chemistry 264:8753-8758.
96. Wedekind, J. E., P. A. Frey, and I. Rayment. 1996. The Structure of nucleotidylated histidine-166 of galactose-1-phosphate uridylyltransferase provides insight into phosphoryl group Transfer. Biochemistry 35:11560-11569.
97. Weissborn, A. C., Q. Liu, M. K. Rumley, and E. P. Kennedy. 1994. UTP: alpha-D-glucose-1-phosphate uridylyltransferase of *Escherichia coli*: isolation and DNA sequence of the galU gene and purification of the enzyme. Journal of Bacteriology 176:2611-2618.
98. Williams, J., J. Luke, and C. Hodgson. 2009. Strain engineering by genome mass transfer: Efficient chromosomal trait transfer method utilizing donor genomic DNA and recipient recombineering hosts. Molecular Biotechnology 43:41-51.
99. Yamamoto, K., A. Nakayama, Y. Yamamoto, and S. Tabata. 2004. Val216 decides the substrate specificity of alpha-glucosidase in *Saccharomyces cerevisiae*. European Journal of Biochemistry 271:3414-3420.
100. Zhang, J. B., P. Kowal, X. Chen, and P. G. Wang. 2003. Large-scale synthesis of globotriose derivatives through recombinant *E. coli*. Organic & Biomolecular Chemistry 1:3048-3053
101. Zhao, J., T. Baba, H. Mori, and K. Shimizu. 2004. Global metabolic response of *Escherichia coli* to gnd or zwf gene-knockout, based on 13C-labeling experiments and the measurement of enzyme activities. Applied Microbiology and Biotechnology 64:91-98.

The invention claimed is:

1. A metabolically engineered bacterium or yeast for the production of glucose-1-phosphate, UDP-glucose, or glucose-6-phosphate, characterized in that said bacterium or yeast has been genetically modified by introducing a heterologous gene encoding a sucrose phosphorylase capable of splitting sucrose into glucose-1-phosphate and fructose, and
  a) comprises a phosphoglucomutase and has been further genetically modified to prevent loss of glucose-1-phosphate via glycolysis due to genetic disruption of an endogenous gene encoding a glucose-1-phosphatase, a glucose-1-phosphate adenylyltransferase, or a combination thereof; or
  b) comprises a UDP-glucose pyrophosphorylase and has been further genetically modified to prevent loss of glucose-1-phosphate via glycolysis due to genetic disruption of an endogenous gene encoding a phosphoglucomutase, a glucose-1-phosphatase, a glucose-1-phosphate adenylyltransferase, or a combination thereof.

2. The metabolically engineered bacterium or yeast according to claim 1, wherein an endogenous gene encoding a phosphoglucomutase and an endogenous gene encoding a glucose-1-phosphatase have been disrupted.

3. The metabolically engineered bacterium or yeast according to claim 1, wherein an endogenous gene encoding a phosphoglucomutase, an endogenous gene encoding a glucose-1-phosphatase, and an endogenous gene encoding a glucose-1-phosphate adenylyltransferase have been disrupted.

4. The metabolically engineered bacterium or yeast according to claim 1, wherein said bacterium or yeast comprises a phosphoglucomutase and has been further genetically modified to prevent loss of glucose-1-phosphate via glycolysis by genetic disruption of an endogenous gene encoding a glucose-1-phosphatase, a glucose-1-phosphate adenylyltransferase, or a combination thereof.

5. The metabolically engineered bacterium or yeast according to claim 1, wherein said bacterium or yeast has been further genetically modified to prevent loss of glucose via glycolysis due to genetic disruption of an endogenous gene encoding a glucokinase, a protein of a phosphotransferase system, or a combination thereof.

6. The metabolically engineered bacterium or yeast according to claim 5, wherein an endogenous gene encoding a glucokinase and an endogenous gene encoding a protein of a phosphotransferase system have been disrupted.

7. A method for the production of glucose-1-phosphate, UDP-glucose, or glucose-6-phosphate, comprising the steps of:
   i) cultivating the metabolically engineered bacterium or yeast according to claim 1, and
   ii) extracting and purifying the glucose-1-phosphate, UDP-glucose, or glucose-6-phosphate.

8. A metabolically engineered bacterium or yeast for the production of UDP-glucose, characterized in that said bacterium or yeast cell:
   (a) has been genetically modified by introducing a heterologous gene encoding a sucrose phosphorylase capable of splitting sucrose into glucose-1-phosphate and fructose;
   (b) has been further genetically modified to prevent loss of glucose-1-phosphate via glycolysis due to genetic disruption of an endogenous gene encoding a phosphoglucomutase, a glucose-1-phosphatase, a glucose-1-phosphate adenylyltransferase, or a combination thereof; and
   (c) comprises a UDP-glucose pyrophosphorylase to catalyze conversion of glucose-1-phosphate and UTP to UDP-glucose.

9. A method for the production of UDP-glucose, comprising the steps of:
   i) cultivating the metabolically engineered bacterium or yeast according to claim 8, and
   ii) extracting and purifying the UDP-glucose.

10. A metabolically engineered bacterium or yeast for the production of glucose-6-phosphate, characterized in that said bacterium or yeast:
    a) has been genetically modified by introducing a heterologous gene encoding a sucrose phosphorylase capable of splitting sucrose into glucose-1-phosphate and fructose; and
    b) has been further genetically modified to prevent loss of glucose-1-phosphate via glycolysis due to genetic disruption of an endogenous gene encoding a glucose-1-phosphatase, a glucose-1-phosphate adenylyltransferase, or a combination thereof; and
    (c) comprises a phosphoglucomutase to catalyze conversion of glucose-1-phosphate to glucose-6-phosphate.

11. A method for the production of glucose-6-phosphate, comprising the steps of:
    i) cultivating the metabolically engineered bacterium or yeast according to claim 10, and
    ii) extracting and purifying the glucose-6-phosphate.

12. A metabolically engineered bacterium or yeast for the production of glucose-1-phosphate, characterized in that said bacterium or yeast:
    a) has been genetically modified by introducing a heterologous gene encoding a sucrose phosphorylase capable of splitting sucrose into glucose-1-phosphate and fructose; and
    b) has been further genetically modified to prevent loss of glucose-1-phosphate via glycolysis due to genetic disruption of an endogenous gene encoding a phosphoglucomutase, a glucose-1-phosphatase, a glucose-1-phosphate adenylyltransferase, or a combination thereof.

13. A method for the production of glucose-1-phosphate, comprising the steps of:
    i) cultivating the metabolically engineered bacterium or yeast according to claim 12, and
    ii) extracting and purifying the glucose-1-phosphate.

14. A metabolically engineered *E. coli* or *S. cerevisiae* for the production of UDP-glucose, wherein said metabolically engineered *E. coli* or *S. cerevisiae* has been genetically modified by introducing a heterologous gene encoding a sucrose phosphorylase capable of splitting sucrose into glucose-1-phosphate and fructose, comprises a UDP-glucose pyrophosphorylase, and has been further genetically modified to disrupt an endogenous gene encoding a glucose-1-phosphatase, a phosphoglucomutase, and/or a glucose-1-phosphate adenylyltransferase.

15. A method for the production of UDP-glucose, comprising the steps of:
    i) cultivating the metabolically engineered *E. coli* or *S. cerevisiae* of claim 14, and
    ii) extracting and purifying the UDP-glucose.

16. A metabolically engineered *E. coli* or *S. cerevisiae* for the production of glucose-6-phosphate, wherein said metabolically engineered *E. coli* or *S. cerevisiae* has been genetically modified by introducing a heterologous gene encoding a sucrose phosphorylase capable of splitting sucrose into glucose-1-phosphate and fructose, comprises a phosphoglucomutase, and has been further genetically modified to disrupt an endogenous gene encoding a glucose-1-phosphatase and/or a glucose-1-phosphate adenylyltransferase.

17. A method for the production of glucose-6-phosphate, comprising the steps of:
    i) cultivating the metabolically engineered *E. coli* or *S. cerevisiae* of claim 16, and
    ii) extracting and purifying the glucose-6-phosphate.

18. A metabolically engineered *E. coli* or *S. cerevisiae* for the production of glucose-1-phosphate, wherein said metabolically engineered *E. coli* or *S. cerevisiae* has been genetically modified by introducing a heterologous gene encoding a sucrose phosphorylase capable of splitting sucrose into glucose-1-phosphate and fructose, and has been further genetically modified to disrupt an endogenous gene encoding a glucose-1-phosphatase, a phosphoglucomutase, and/or a glucose-1-phosphate adenylyltransferase.

19. A method for the production of glucose-1-phosphate, comprising the steps of:
    i) cultivating the metabolically engineered *E. coli* or *S. cerevisiae* of claim 18, and
    ii) extracting and purifying the glucose-1-phosphate.

* * * * *

SEQUENCE LISTING

<160> NUMBER OF SEQ ID NOS: 56

<210> SEQ ID NO 1
<211> LENGTH: 768
<212> TYPE: PRT
<213> ORGANISM: Dictyostellium discoideum

<400> SEQUENCE: 1

Met Asn Asp Ser Pro Ile Ile Ser Val Val Leu Pro Phe Leu Ile Lys
1               5                   10                  15

Asp Asn Asp Asp Lys Ser Leu Asn Tyr Gln Gly Ile Asn Asn Leu Ile
            20                  25                  30

Ile Ser Ile Asp Ser Ile Ile Glu Gln Thr Phe Lys Glu Trp Glu Leu
        35                  40                  45

Ile Leu Val Asp Asp Gly Ser Asn Glu Ile Leu Glu Gln Leu Leu
    50                  55                  60

Ser Lys Arg Tyr Ser Thr Asp Asn Arg Ile Lys Phe Ile Ile Asn Lys
65                  70                  75                  80

Glu Asn Lys Gly Ile Val Lys Ser Leu Asn Asp Ala Ile Leu Asn His
                85                  90                  95

Cys Ser Pro Thr Ser Lys Tyr Ile Ala Arg Met Asp Ser Asp Asp Ile
            100                 105                 110

Ser His Pro Thr Arg Leu Gln Ser Gln Leu Lys Tyr Leu Gln Ser Asn
        115                 120                 125

Glu Thr Ile Asp Ile Leu Gly Cys Pro Ile Lys Met Phe Asn Asn Asn
    130                 135                 140

Lys Leu Ile Glu Ile Leu Asn Asn Asn Asn Asn Asn Asn Ile Asn
145                 150                 155                 160

Asn Asn Val Lys Glu Leu Ile Asn Ile Ile Asn Asn Glu Glu Ser Phe
                165                 170                 175

Lys Phe Ile Gln His Pro Asp Lys Asp Ile Leu Met Trp Ser Met Phe
            180                 185                 190

Phe Asn Cys Cys Ile Val His Pro Ser Val Ile Phe Lys Arg Ser Ile
        195                 200                 205

Phe Thr Ile Glu His Cys Tyr Glu Glu Asn Asn Gln Phe Pro Phe Ile
    210                 215                 220

Glu Asp Tyr Leu Phe Trp Leu Lys Ser Leu Ile Met Lys Gly Leu Asn
225                 230                 235                 240

Ile Ser Asn Ile Gln Ser Ser Thr Pro Leu Leu Tyr Leu Arg Lys His
                245                 250                 255

Asn Asn Ser Ile Ser Phe Lys Asn Ile Glu Lys Gln Lys Asp Ser Thr
            260                 265                 270

Ala Asn Ala Ser Cys Tyr Tyr Leu Asn Ile Leu Phe Lys Arg Phe Asn
        275                 280                 285

Ile Asp Ser Glu Ile Ile Gln Asn Ser Ser Leu Ser Met Lys Glu Ile
    290                 295                 300

Ile Gln Phe Phe Gln Leu Ser Pro Ser Ser Leu Ser Lys Ile Asn Asn
305                 310                 315                 320

Ile Ser Ile Glu Leu Phe Glu Phe Ala Phe Lys Tyr Leu Glu Leu Ile
                325                 330                 335

Glu Lys Ser Cys Thr Lys Gln Gln Pro Asn Tyr Ser Asn Ser Ile Lys
            340                 345                 350

Asp Ala Ala Asn Glu Lys Met Gly Glu Leu Val Ser Leu Cys Leu Ser
        355                 360                 365

Asn Tyr Pro Asn Asn Gln Lys Ser Ser Leu Leu Trp Glu Lys Trp Leu
        370                 375                 380

Ser Arg Asn Pro Thr Ser Gln Leu Leu Ser Leu Leu Ser Asn Leu Asn
385                 390                 395                 400

Val Lys Ser Ser Thr Thr Ile Ile Asn Asn Asn Ile Asn Asn Asn Asn
                405                 410                 415

Asn Asn Asn Asn Asn Asn Asn Asn Asn Asn Asn Asn Asn Asn Asn Asn
            420                 425                 430

Asn Asn Asn Asn Asn Asn Ser Ile Leu Asn Phe Ile Ser Gly
        435                 440                 445

Ile Asn Ser Asn Lys Ile Asn Thr Pro Lys Ser Asn Asn Asn Lys Phe
450                 455                 460

Lys Glu Asn Gly Ile Arg Ile Ile Cys Phe Ser Lys Asp Arg Ala Phe
465                 470                 475                 480

Gln Leu Lys Glu Tyr Leu Arg Thr Phe Phe Lys Tyr Leu Lys Asn Asp
                485                 490                 495

Asp Asn Gly Asn Asp Lys Phe Glu Ile Ile Val Asp Val Leu Phe Thr
            500                 505                 510

Tyr Ser Asn Glu Lys Phe Lys Asn Ser Tyr Gln Leu Val Ile Glu Ser
        515                 520                 525

Phe Pro Gln Val Asn Phe Ile Lys Glu Glu Asn Phe Thr Asp Gln Leu
    530                 535                 540

Ile Asn Leu Val Gln Lys Thr Asn Lys Leu Glu Tyr Val Met Phe Ser
545                 550                 555                 560

Val Asp Asp Ile Leu Tyr Tyr Asn Glu Phe Asn Leu Lys Glu Tyr Cys
                565                 570                 575

Leu Ser Leu Asn Ser Glu Pro Leu Ala Leu Gly Phe Tyr Met Lys Leu
            580                 585                 590

Asn Lys Asn Ile Thr Tyr Cys His Thr Cys Asn Gln Asp Ile Thr Ile
        595                 600                 605

Pro Leu Asn Ser Asn Thr Ile Ser Arg Thr Glu Asn Asn Phe Lys Tyr
    610                 615                 620

Leu Lys Trp Asn Arg Asn Asp Asn Asp Cys Lys Lys Asp Trp Asn Tyr
625                 630                 635                 640

Pro Trp Asp Leu Cys Ser Thr Ile Tyr Arg Cys Asn Asp Ile Asp Ser
                645                 650                 655

Ile Ile Asn Gly Ile Val Lys Tyr Tyr Gly Ile Arg Asn Gly Ile Asn
            660                 665                 670

His Pro Asn Arg Phe Glu Phe Asn Gly Asn Arg Pro Ile Ile Gln Lys
        675                 680                 685

Gln Ile Tyr Gln Asn Lys Pro Tyr Cys Leu Cys Leu Ser Asp His Tyr
    690                 695                 700

Ser Pro Met Ser Val Val Thr Ile Asn Arg Val Gln Asp Val Tyr Asp
705                 710                 715                 720

Asn Pro Ile Tyr Asp Gln Thr Leu Ser Leu Asp Asp Leu Asp Gln Leu
                725                 730                 735

Leu Tyr Ser Asn Lys Ser Leu Asn Asp Glu Lys Tyr Lys Glu Asn Ser
            740                 745                 750

Leu Ser Leu Asn Phe Lys Ser Val His Ile Gly Glu Leu Phe Ile Ser
        755                 760                 765

<210> SEQ ID NO 2
<211> LENGTH: 2307
<212> TYPE: DNA

<213> ORGANISM: Artificial sequence
<220> FEATURE:
<223> OTHER INFORMATION: codon optimized sequence encoding SEQ ID NO 1

<400> SEQUENCE: 2

```
atgaacgata gcccgattat tagcgttgtt ctgccgtttc tgatcaaaga taacgatgat       60
aaaagcctga actaccaggg cattaacaac ctgattatta gcatcgatag catcatcgag      120
cagaccttta aagaatggga actgattctg gttgatgatg cagcaataa cgaaattctg      180 gaacagctgc tgagcaaacg ttatagcacc gataaccgca tcaaatttat tattaataaa      240
gaaaataaag gcattgtgaa aagcctgaat gatgccattc tgaatcattg tagcccgacc      300
agcaaatata ttgcacgtat ggatagcgac gatattagcc atccgacccg tctgcagagc      360
cagctgaaat atctgcagag caatgaaacc attgatattc tgggttgccc gatcaaaatg      420
tttaataata ataaactgat tgaaattctg aataataata caataacaa caatattaat      480 aataatgtga agaactgat taatattatt aataatgaag aaagctttaa atttattcag      540
catccggata agatattct gatgtggtcc atgttcttca attgctgtat tgttcatccg      600
agcgtgattt taaacgcag cattttacc atcgagcact gctatgaaga aataatcag      660 tttccgttca tcgaggatta cctgttttgg ctgaaatccc tgattatgaa aggcctgaac      720
attagcaata tccagagcag cacaccgctg ctgtatctgc gtaaacataa taacagcatt      780
agctttaaaa atattgaaaa acagaaagat agcaccgcca atgccagctg ttattatctg      840
aacattctgt tcaaacgctt taacatcgac agcgaaatta ttcagaatag cagcctgagc      900
atgaaagaaa tcatccagtt ttttcagctg agcccgagca gcctgtccaa attaataac      960 attagcatcg aactgtttga atttgccttt aaatatctgg aactgatcga aaaagctgt    1020 accaaacagc agccgaatta tagcaacagc attaagatg cagccaacga aaaatgggt    1080 gaactggtta gcctgtgtct gagcaattat ccgaataatc agaaaagcag tctgctgtgg    1140
gaaaaatggg tgagccgtaa tccgaccagc agctgctga gtctgctgag caatctgaat    1200
gttaaaagca gcaccaccat tattaataac aatattaaca acaacaataa taataacaac    1260
aataataaca ataacaataa caataataac aacaacaaca ataataataa taacaacaac    1320
agcattctga ttttattag cggcattaat agcaataaaa ttaatacccc gaaaagcaac    1380
aataacaaat ttaaagagaa tggcattcgc attatttgct tcagcaaaga tcgtgcattc    1440
cagctgaaag aatatctgcg caccttcttc aaatatctga aaaatgatga taatggcaat    1500
gataaatttg aaattattgt ggatgtgctg tttacctata gcaatgaaaa attcaaaaat    1560
agctatcagc tggtgatcga aagctttccg caggttaact ttattaaaga gaaaactttt    1620
accgatcagc tgattaacct ggtgcagaaa accaacaaac tggaatatgt gatgttcagc    1680
gtggatgata tcctgtatta caacgagttc aatctgaaag agtattgcct gagcctgaat    1740
agcgaaccgc tggcactggg tttttatatg aaactgaata aaatattac ctattgccat    1800 acctgcaacc aggatattac cattccgctg aatagcaata ccattagccg caccgaaaat    1860
aactttaaat acctgaaatg gaatcgcaac gataatgatt gcaaaaaaga ctggaactat    1920
ccgtgggatc tgtgtagcac catttatcgt tgcaacgaca ttgacagcat cattaatggt    1980
attgtgaaat attatggtat tcgcaacggc attaatcatc cgaatcgctt tgaatttaat    2040
ggcaaccgtc cgattattca gaaacaaatc taccagaaca aaccgtattg tctgtgcctg    2100
agcgatcatt attcaccgat gagcgttgtt accattaatc gtgttcagga tgtgtatgat    2160
aacccgattt atgatcagac cctgagcctg gatgatctgg atcaactgct gtatagcaat    2220
```

| | |
|---|---|
| aaatccctga acgatgaaaa atataaagaa aacagcctga gtctgaactt caaaagcgtt | 2280 |
| catattggcg aactgttcat cagctaa | 2307 |

<210> SEQ ID NO 3
<211> LENGTH: 2307
<212> TYPE: DNA
<213> ORGANISM: Dictyostellium discoideum

<400> SEQUENCE: 3

| | |
|---|---|
| atgaatgatt caccaataat aagtgtagtt ttaccttttt taataaagga caatgacgat | 60 |
| aaatcattaa attaccaagg aataaataat ttaataatat caatagatag cattattgaa | 120 |
| caaactttta agaatgggaa ttaattttta gttgatgatg gatcaaataa tgaaattttg | 180 |
| gagcaattac tttcaaaaag atatagtaca gataatagaa ttaaattcat aataaataaa | 240 |
| gagaataaag gtattgttaa aagtttaaat gatgcaattt taaatcattg ttcaccaact | 300 |
| tcaaaatata ttgctcgtat ggattcgatt gatatttctc atccaacaag attacaatct | 360 |
| caacttaaat atcttcaatc aaatgaaaca attgatatat taggttgtcc aattaaaatg | 420 |
| tttaataata taaattaat tgaaatttta aataataata ataataataa taatattaat | 480 |
| aataatgtga aagagttaat taatataatt aataatgaag aatcttttaa atttattcaa | 540 |
| catcctgata agatatttt aatgtggtca atgttttca attgttgtat tgttcaccct | 600 |
| tctgtaatat ttaaaagatc gatattcact attgaacatt gttatgaaga aacaaccaa | 660 |
| tttccattca ttgaagatta cttattttgg ttaaaatcct taataatgaa aggtttaaat | 720 |
| atttcaaata tccaatcatc aacaccatta ctatatttaa gaaaacataa taactctata | 780 |
| tcttttaaaa atattgaaaa acaaaaagat tccactgcta atgcatcttg ttattatcta | 840 |
| aatatacttt ttaaaagatt taatattgat tctgaaatta ttcaaaattc ttcactctca | 900 |
| atgaaagaaa ttattcagtt cttcaacctt tcaccatcat ctttatcaaa atcaataat | 960 |
| atttcaattg aattatttga atttgcattt aaatatctag aattaattga aaaatcatgt | 1020 |
| acaaaacaac aaccaaacta ttcaaacagt ataaagatg cagcaaatga aaaaatgggt | 1080 |
| gaattagtat ctttatgttt atcaaattat ccaataatcc aaaaatcatc attactttgg | 1140 |
| gaaaaatggt tatcaagaaa tccaacctca caattactat cacttttatc aaatttaaat | 1200 |
| gtaaaatctt caactactat aattaataat aatattaata ataataataa taataataat | 1260 |
| aataataata ataataataa taataataat aataataata ataataataa taataataat | 1320 |
| tcaattttaa attttatatc tggcattaat agtaataaaa taaatactcc aaaatctaat | 1380 |
| aataataaat ttaaagaaaa tggaattaga ataatttgtt tctcaaaaga tagagcattt | 1440 |
| caattaaaag aatatcttag aacatttttt aaatatttaa aaaatgatga taatggaaat | 1500 |
| gataaatttg aaattattgt tgatgtatta tttacatatt caaatgagaa attcaaaaac | 1560 |
| tcttatcaat tagttattga aagttttcca caagttaatt ttattaaaga agagaatttc | 1620 |
| actgatcaat taattaattt agttcaaaaa acaaataaac ttgaatatgt catgtttca | 1680 |
| gttgatgata ttcttattta taatgaattc aatctcaaag aatattgttt atctttgaat | 1740 |
| agtgagccat tggcattagg tttctatatg aagttaaata aaaatattac ctattgtcat | 1800 |
| acttgtaatc aagatataac aataccatta aattcaaata ctattagtag aacagagaat | 1860 |
| aattttaaat atttaaaatg gaatagaaat gataatgatt gtaaaaagga ttggaattat | 1920 |
| ccatgggatt tatgttcaac catttataga tgtaatgata ttgattcaat cattaatggt | 1980 |

```
atagttaaat attatggaat tagaaatggt attaatcatc caaatagatt cgaattcaat    2040
ggtaatagac caatcattca aaagcaaatc tatcaaaata aaccctactg tttatgttta    2100
tcagatcact attctccaat gtctgttgta actattaata gagttcaaga tgtctatgat    2160
aatccaattt atgaccaaac cctatcttta gatgatttag atcaattact ttattcaaac    2220
aaatcattaa atgatgaaaa atataaagaa aatagtttat ctttaaattt taaaagtgtt    2280
catattggtg aacttttat ttcttaa                                         2307
```

<210> SEQ ID NO 4
<211> LENGTH: 329
<212> TYPE: PRT
<213> ORGANISM: Dictyostellium discoideum

<400> SEQUENCE: 4

```
Met Ser Ile Leu Asn Phe Ile Ser Gly Ile Asn Ser Asn Lys Ile Asn
1               5                   10                  15

Thr Pro Lys Ser Asn Asn Asn Lys Phe Lys Glu Asn Gly Ile Arg Ile
            20                  25                  30

Ile Cys Phe Ser Lys Asp Arg Ala Phe Gln Leu Lys Glu Tyr Leu Arg
        35                  40                  45

Thr Phe Phe Lys Tyr Leu Lys Asn Asp Asp Asn Gly Asn Asp Lys Phe
    50                  55                  60

Glu Ile Ile Val Asp Val Leu Phe Thr Tyr Ser Asn Lys Phe Lys
65                  70                  75                  80

Asn Ser Tyr Gln Leu Val Ile Glu Ser Phe Pro Gln Val Asn Phe Ile
                85                  90                  95

Lys Glu Glu Asn Phe Thr Asp Gln Leu Ile Asn Leu Val Gln Lys Thr
            100                 105                 110

Asn Lys Leu Glu Tyr Val Met Phe Ser Val Asp Asp Ile Leu Tyr Tyr
        115                 120                 125

Asn Glu Phe Asn Leu Lys Glu Tyr Cys Leu Ser Leu Asn Ser Glu Pro
    130                 135                 140

Leu Ala Leu Gly Phe Tyr Met Lys Leu Asn Lys Asn Ile Thr Tyr Cys
145                 150                 155                 160

His Thr Cys Asn Gln Asp Ile Thr Ile Pro Leu Asn Ser Asn Thr Ile
                165                 170                 175

Ser Arg Thr Glu Asn Asn Phe Lys Tyr Leu Lys Trp Asn Arg Asn Asp
            180                 185                 190

Asn Asp Cys Lys Lys Asp Trp Asn Tyr Pro Trp Asp Leu Cys Ser Thr
        195                 200                 205

Ile Tyr Arg Cys Asn Asp Ile Asp Ser Ile Ile Asn Gly Ile Val Lys
    210                 215                 220

Tyr Tyr Gly Ile Arg Asn Gly Ile Asn His Pro Asn Arg Phe Glu Phe
225                 230                 235                 240

Asn Gly Asn Arg Pro Ile Ile Gln Lys Gln Ile Tyr Gln Asn Lys Pro
                245                 250                 255

Tyr Cys Leu Cys Leu Ser Asp His Tyr Ser Pro Met Ser Val Val Thr
            260                 265                 270

Ile Asn Arg Val Gln Asp Val Tyr Asp Asn Pro Ile Tyr Asp Gln Thr
        275                 280                 285

Leu Ser Leu Asp Asp Leu Asp Gln Leu Leu Tyr Ser Asn Lys Ser Leu
    290                 295                 300

Asn Asp Glu Lys Tyr Lys Glu Asn Ser Leu Ser Leu Asn Phe Lys Ser
305                 310                 315                 320
```

Val His Ile Gly Glu Leu Phe Ile Ser
            325

<210> SEQ ID NO 5
<211> LENGTH: 990
<212> TYPE: DNA
<213> ORGANISM: Artificial sequence
<220> FEATURE:
<223> OTHER INFORMATION: codon optimized sequence encoding part of SEQ
      ID NO 2

<400> SEQUENCE: 5

| | | |
|---|---|---|
| atgagcattc tgaattttat tagcggcatt aatagcaata aaattaatac cccgaaaagc | 60 |
| aacaataaca aatttaaaga gaatggcatt cgcattattt gcttcagcaa agatcgtgca | 120 |
| ttccagctga agaatatctc tgcgcaccttc ttcaaatatc tgaaaaatga tgataatggc | 180 |
| aatgataaat tgaaattat tgtggatgtg ctgtttacct atagcaatga aaaattcaaa | 240 |
| aatagctatc agctggtgat cgaaagcttt ccgcaggtta actttattaa agaagaaaac | 300 |
| tttaccgatc agctgattaa cctggtgcag aaaaccaaca aactggaata tgtgatgttc | 360 |
| agcgtggatg atatcctgta ttacaacgag ttcaatctga agagtattg cctgagcctg | 420 |
| aatagcgaac cgctggcact gggtttttat atgaaactga ataaaaatat acctattgc | 480 |
| catacctgca accaggatat taccattccg ctgaatagca ataccattag ccgcaccgaa | 540 |
| aataacttta ataccctgaa atggaatcgc aacgataatg attgcaaaaa agactggaac | 600 |
| tatccgtggg atctgtgtag caccattttat cgttgcaacg acattgacag catcattaat | 660 |
| ggtattgtga atattatgg tattcgcaac ggcattaatc atccgaatcg ctttgaattt | 720 |
| aatggcaacc gtccgattat tcagaaacaa atctaccaga caaaccgta ttgtctgtgc | 780 |
| ctgagcgatc attattcacc gatgagcgtt gttaccatta atcgtgttca ggatgtgtat | 840 |
| gataacccga tttatgatca gaccctgagc ctggatgatc tggatcaact gctgtatagc | 900 |
| aataaatccc tgaacgatga aaaatataaa gaaaacagcc tgagtctgaa cttcaaaagc | 960 |
| gttcatattg gcgaactgtt catcagctaa | 990 |

<210> SEQ ID NO 6
<211> LENGTH: 987
<212> TYPE: DNA
<213> ORGANISM: Dictyostellium discoideum

<400> SEQUENCE: 6

| | | |
|---|---|---|
| tcaattttaa attttatatc tggcattaat agtaataaaa taaatactcc aaaatctaat | 60 |
| aataataaat ttaaagaaaa tggaattaga ataatttgtt tctcaaaaga tagagcattt | 120 |
| caattaaaag aatatcttag aacattttt aaatatttaa aaaatgatga taatggaaat | 180 |
| gataaatttg aaattattgt tgatgtatta tttacatatt caaatgagaa attcaaaaac | 240 |
| tcttatcaat tagttattga agttttcca caagttaatt ttattaaaga agagaatttc | 300 |
| actgatcaat taattaattt agttcaaaaa acaaataaac ttgaatatgt catgttttca | 360 |
| gttgatgata ttctttatta taatgaattc aatctcaaag aatattgttt atctttgaat | 420 |
| agtgagccat ggcattagg tttctatatg aagttaaata aaaatattac ctattgtcat | 480 |
| acttgtaatc aagatataac aataccatta aattcaaata ctattagtag aacagagaat | 540 |
| aatttttaaat atttaaaatg gaatagaaat gataatgatt gtaaaaagga ttggaattat | 600 |
| ccatgggatt tatgttcaac catttataga tgtaatgata ttgattcaat cattaatggt | 660 |

```
atagttaaat attatggaat tagaaatggt attaatcatc caaatagatt cgaattcaat    720
ggtaatagac caatcattca aaagcaaatc tatcaaaata aaccctactg tttatgttta    780
tcagatcact attctccaat gtctgttgta actattaata gagttcaaga tgtctatgat    840
aatccaattt atgaccaaac cctatcttta gatgatttag atcaattact ttattcaaac    900
aaatcattaa atgatgaaaa atataaagaa aatagtttat ctttaaattt taaaagtgtt    960
catattggtg aactttttat ttcttaa                                        987

<210> SEQ ID NO 7
<211> LENGTH: 74
<212> TYPE: DNA
<213> ORGANISM: Artificial sequence
<220> FEATURE:
<223> OTHER INFORMATION: Primer

<400> SEQUENCE: 7
cataatggat ttccttacgc gaaatacggg cagacatggc ctgcccggtt attagtgtag    60
gctggagctg cttc                                                      74

<210> SEQ ID NO 8
<211> LENGTH: 71
<212> TYPE: DNA
<213> ORGANISM: Artificial sequence
<220> FEATURE:
<223> OTHER INFORMATION: Primer

<400> SEQUENCE: 8
gtatgttgtg tggaattgtg agcggataac aatttcacac aggaaacagc tcatatgaat    60
atcctcctta g                                                         71

<210> SEQ ID NO 9
<211> LENGTH: 75
<212> TYPE: DNA
<213> ORGANISM: Artificial sequence
<220> FEATURE:
<223> OTHER INFORMATION: Primer

<400> SEQUENCE: 9
agaccgccgg ttttaagcag cgggaacatc tctgaacata catgtaaaac ctgcagtgta    60
ggctggagct gcttc                                                     75

<210> SEQ ID NO 10
<211> LENGTH: 82
<212> TYPE: DNA
<213> ORGANISM: Artificial sequence
<220> FEATURE:
<223> OTHER INFORMATION: Primer

<400> SEQUENCE: 10
gtctggcagg gacctgcaca cggattgtgt gtgttccaga gatgataaaa aaggagttag    60
tccatatgaa tatcctcctt ag                                             82

<210> SEQ ID NO 11
<211> LENGTH: 70
<212> TYPE: DNA
<213> ORGANISM: Artificial sequence
<220> FEATURE:
<223> OTHER INFORMATION: Primer

<400> SEQUENCE: 11
catatttctg tcacactctt tagtgattga taacaaaaga ggtgccagga gtgtaggctg    60
```

-continued

```
gagctgcttc                                                            70

<210> SEQ ID NO 12
<211> LENGTH: 70
<212> TYPE: DNA
<213> ORGANISM: Artificial sequence
<220> FEATURE:
<223> OTHER INFORMATION: Primer

<400> SEQUENCE: 12
taaaaacgtt taaccagcga ctcccccgct tctcgcgggg gagttttctg catatgaata     60
tcctccttag                                                            70

<210> SEQ ID NO 13
<211> LENGTH: 70
<212> TYPE: DNA
<213> ORGANISM: Artificial sequence
<220> FEATURE:
<223> OTHER INFORMATION: Primer

<400> SEQUENCE: 13
ggcgctacaa tcttccaaag tcacaattct caaaatcaga agagtattgc gtgtaggctg     60
gagctgcttc                                                            70

<210> SEQ ID NO 14
<211> LENGTH: 70
<212> TYPE: DNA
<213> ORGANISM: Artificial sequence
<220> FEATURE:
<223> OTHER INFORMATION: Primer

<400> SEQUENCE: 14
ggttgccgga tgcggcgtga acgccttatc cggcctacat atcgacgatg catatgaata     60
tcctccttag                                                            70

<210> SEQ ID NO 15
<211> LENGTH: 69
<212> TYPE: DNA
<213> ORGANISM: Artificial sequence
<220> FEATURE:
<223> OTHER INFORMATION: Primer

<400> SEQUENCE: 15
gacttccggc aacagatttc attttgcatt ccaaagttca gaggtagtcg tgtaggctgg     60
agctgcttc                                                             69

<210> SEQ ID NO 16
<211> LENGTH: 69
<212> TYPE: DNA
<213> ORGANISM: Artificial sequence
<220> FEATURE:
<223> OTHER INFORMATION: Primer

<400> SEQUENCE: 16
gcttctgtca tcggtttcag ggtaaaggaa tctgcctttt tccgaaatcc atatgaatat     60
cctccttag                                                             69

<210> SEQ ID NO 17
<211> LENGTH: 71
<212> TYPE: DNA
<213> ORGANISM: Artificial sequence
<220> FEATURE:
```

<223> OTHER INFORMATION: Primer

<400> SEQUENCE: 17
cactttccgc tgattcggtg ccagactgaa atcagcctat aggaggaaat ggtgtaggct    60
ggagctgctt c                                                        71

<210> SEQ ID NO 18
<211> LENGTH: 70
<212> TYPE: DNA
<213> ORGANISM: Artificial sequence
<220> FEATURE:
<223> OTHER INFORMATION: Primer

<400> SEQUENCE: 18
gttgccgaca ggttggtgat gattccccca atgctggggg aatgttttg catatgaata     60 tcctccttag                                                          70

<210> SEQ ID NO 19
<211> LENGTH: 70
<212> TYPE: DNA
<213> ORGANISM: Artificial sequence
<220> FEATURE:
<223> OTHER INFORMATION: Primer

<400> SEQUENCE: 19
tgagaaggtt tgcggaacta tctaaaacgt tgcagacaaa ggacaaagca gtgtaggctg    60
gagctgcttc                                                          70

<210> SEQ ID NO 20
<211> LENGTH: 71
<212> TYPE: DNA
<213> ORGANISM: Artificial sequence
<220> FEATURE:
<223> OTHER INFORMATION: Primer

<400> SEQUENCE: 20
catacgtaaa aaagggcgat cttgcgaccg ccctttttt attaaatgtg tcatatgaat     60
atcctcctta g                                                        71

<210> SEQ ID NO 21
<211> LENGTH: 70
<212> TYPE: DNA
<213> ORGANISM: Artificial sequence
<220> FEATURE:
<223> OTHER INFORMATION: Primer

<400> SEQUENCE: 21
tgagaaggtt tgcggaacta tctaaaacgt tgcagacaaa ggacaaagca acgaaaggct    60
cagtcgaaag                                                          70

<210> SEQ ID NO 22
<211> LENGTH: 71
<212> TYPE: DNA
<213> ORGANISM: Artificial sequence
<220> FEATURE:
<223> OTHER INFORMATION: Primer

<400> SEQUENCE: 22
catacgtaaa aaagggcgat cttgcgaccg ccctttttt attaaatgtg tagaactcca     60
gcatgagatc c                                                        71

```
<210> SEQ ID NO 23
<211> LENGTH: 70
<212> TYPE: DNA
<213> ORGANISM: Artificial sequence
<220> FEATURE:
<223> OTHER INFORMATION: Primer

<400> SEQUENCE: 23
tgagaaggtt tgcggaacta tctaaaacgt tgcagacaaa ggacaaagca gtgtaggctg    60
gagctgcttc                                                          70

<210> SEQ ID NO 24
<211> LENGTH: 71
<212> TYPE: DNA
<213> ORGANISM: Artificial sequence
<220> FEATURE:
<223> OTHER INFORMATION: Primer

<400> SEQUENCE: 24
catacgtaaa aaagggcgat cttgcgaccg ccctttttt attaaatgtg tcatccgtca    60
ggatggcctt c                                                        71

<210> SEQ ID NO 25
<211> LENGTH: 72
<212> TYPE: DNA
<213> ORGANISM: Artificial sequence
<220> FEATURE:
<223> OTHER INFORMATION: Primer

<400> SEQUENCE: 25
gccacgcgtg agaacgtaaa aaaagcaccc atactcagga gcactctcaa ttgtgtaggc    60
tggagctgct tc                                                        72

<210> SEQ ID NO 26
<211> LENGTH: 75
<212> TYPE: DNA
<213> ORGANISM: Artificial sequence
<220> FEATURE:
<223> OTHER INFORMATION: Primer

<400> SEQUENCE: 26
cacctgtaaa aaaggcagcc atctggctgc cttagtctcc ccaacgtctt acggacatat    60
gaatatcctc cttag                                                     75

<210> SEQ ID NO 27
<211> LENGTH: 70
<212> TYPE: DNA
<213> ORGANISM: Artificial sequence
<220> FEATURE:
<223> OTHER INFORMATION: Primer

<400> SEQUENCE: 27
cgagaaggcc cggattgtca tggacgatga gatacaccgg aatatcatgg gtgtaggctg    60
gagctgcttc                                                           70

<210> SEQ ID NO 28
<211> LENGTH: 76
<212> TYPE: DNA
<213> ORGANISM: Artificial sequence
<220> FEATURE:
<223> OTHER INFORMATION: Primer

<400> SEQUENCE: 28
```

```
ccaggtattt acagtgtgag aaagaattat tttgacttta gcggagcagt tgaagacata    60
tgaatatcct ccttag                                                    76
```

<210> SEQ ID NO 29
<211> LENGTH: 70
<212> TYPE: DNA
<213> ORGANISM: Artificial sequence
<220> FEATURE:
<223> OTHER INFORMATION: Primer

<400> SEQUENCE: 29

```
atatccagcc agtcttccgg ctgtagtcct aacagagcac tgttactgtc agcattacac    60
gtcttgagcg                                                           70
```

<210> SEQ ID NO 30
<211> LENGTH: 70
<212> TYPE: DNA
<213> ORGANISM: Artificial sequence
<220> FEATURE:
<223> OTHER INFORMATION: Primer

<400> SEQUENCE: 30

```
gctttaagtg gttgagatca catttccttg ctcatccccg caactcctcc catatgaata    60
tcctccttag                                                           70
```

<210> SEQ ID NO 31
<211> LENGTH: 68
<212> TYPE: DNA
<213> ORGANISM: Artificial sequence
<220> FEATURE:
<223> OTHER INFORMATION: Primer

<400> SEQUENCE: 31

```
atatccagcc agtcttccgg ctgtagtcct aacagagcac tgttactgtc gtaaaacgac    60
ggccagtg                                                             68
```

<210> SEQ ID NO 32
<211> LENGTH: 72
<212> TYPE: DNA
<213> ORGANISM: Artificial sequence
<220> FEATURE:
<223> OTHER INFORMATION: Primer

<400> SEQUENCE: 32

```
caacggccat tttttgcact tagatacaga ttttctgcgc tgtattgcat tgccgggatc    60
cgatgcatat gg                                                        72
```

<210> SEQ ID NO 33
<211> LENGTH: 75
<212> TYPE: DNA
<213> ORGANISM: Artificial sequence
<220> FEATURE:
<223> OTHER INFORMATION: Primer

<400> SEQUENCE: 33

```
ttttattttg cccttcaatg ggaccgctac caaacatcag gaggatgaat gaaacagcat    60
tacacgtctt gagcg                                                     75
```

<210> SEQ ID NO 34
<211> LENGTH: 70
<212> TYPE: DNA
<213> ORGANISM: Artificial sequence

```
<220> FEATURE:
<223> OTHER INFORMATION: Primer

<400> SEQUENCE: 34
ttccgttgaa ggcaacagta attgcgcccc ggttaagccc gcgccgatcc catatgaata      60
tcctccttag                                                            70

<210> SEQ ID NO 35
<211> LENGTH: 71
<212> TYPE: DNA
<213> ORGANISM: Artificial sequence
<220> FEATURE:
<223> OTHER INFORMATION: Primer

<400> SEQUENCE: 35
gtagcattgt tcctaagtat gactccattt ttccaggaat ggtcgcaaat cgtgtaggct      60
ggagctgctt c                                                          71

<210> SEQ ID NO 36
<211> LENGTH: 70
<212> TYPE: DNA
<213> ORGANISM: Artificial sequence
<220> FEATURE:
<223> OTHER INFORMATION: Primer

<400> SEQUENCE: 36
ttcacgccgc atccggcaag caaaccagct cataagccgg gagaacaacc catatgaata      60
tcctccttag                                                            70

<210> SEQ ID NO 37
<211> LENGTH: 70
<212> TYPE: DNA
<213> ORGANISM: Artificial sequence
<220> FEATURE:
<223> OTHER INFORMATION: Primer

<400> SEQUENCE: 37
ttcacgccgc atccggcaag caaaccagct cataagccgg gagaacaacc ccgcttacag      60
acaagctgtg                                                            70

<210> SEQ ID NO 38
<211> LENGTH: 71
<212> TYPE: DNA
<213> ORGANISM: Artificial sequence
<220> FEATURE:
<223> OTHER INFORMATION: Primer

<400> SEQUENCE: 38
gtagcattgt tcctaagtat gactccattt ttccaggaat ggtcgcaaat cagccatgac      60
ccgggaatta c                                                          71

<210> SEQ ID NO 39
<211> LENGTH: 70
<212> TYPE: DNA
<213> ORGANISM: Artificial sequence
<220> FEATURE:
<223> OTHER INFORMATION: Primer

<400> SEQUENCE: 39
atcgccgacc acttcgcgcc gctgatggtt ttttcacgta agctcatatc ccgcttacag      60
acaagctgtg                                                            70
```

<210> SEQ ID NO 40
<211> LENGTH: 70
<212> TYPE: DNA
<213> ORGANISM: Artificial sequence
<220> FEATURE:
<223> OTHER INFORMATION: Primer

<400> SEQUENCE: 40
ggatcttccc ttaccccact gcgggtaagg ggctaataac aggaacaacg agccatgacc    60
cgggaattac    70

<210> SEQ ID NO 41
<211> LENGTH: 42
<212> TYPE: DNA
<213> ORGANISM: Artificial sequence
<220> FEATURE:
<223> OTHER INFORMATION: Primer

<400> SEQUENCE: 41
gggggccccc gggggtatga gcttacgtga aaaaaccatc ag    42

<210> SEQ ID NO 42
<211> LENGTH: 43
<212> TYPE: DNA
<213> ORGANISM: Artificial sequence
<220> FEATURE:
<223> OTHER INFORMATION: Primer

<400> SEQUENCE: 42
gggcccgggc ccgggcgttg ttcctgttat tagccccta ccc    43

<210> SEQ ID NO 43
<211> LENGTH: 70
<212> TYPE: DNA
<213> ORGANISM: Artificial sequence
<220> FEATURE:
<223> OTHER INFORMATION: Primer

<400> SEQUENCE: 43
atcgccgacc acttcgcgcc gctgatggtt ttttcacgta agctcatatc gtgtaggctg    60
gagctgcttc    70

<210> SEQ ID NO 44
<211> LENGTH: 70
<212> TYPE: DNA
<213> ORGANISM: Artificial sequence
<220> FEATURE:
<223> OTHER INFORMATION: Primer

<400> SEQUENCE: 44
ggatcttccc ttaccccact gcgggtaagg ggctaataac aggaacaacg catatgaata    60
tcctccttag    70

<210> SEQ ID NO 45
<211> LENGTH: 70
<212> TYPE: DNA
<213> ORGANISM: Artificial sequence
<220> FEATURE:
<223> OTHER INFORMATION: Primer

<400> SEQUENCE: 45
ttttgatatc gaaccagacg ctccattcgc ggatgtactc aaggtcgaac gtgtaggctg    60
gagctgcttc    70

<210> SEQ ID NO 46
<211> LENGTH: 70
<212> TYPE: DNA
<213> ORGANISM: Artificial sequence
<220> FEATURE:
<223> OTHER INFORMATION: Primer

<400> SEQUENCE: 46
tctatggtgc aacgcttttc agatatcacc atcatgtttg ccggactatg catatgaata    60
tcctccttag                                                          70

<210> SEQ ID NO 47
<211> LENGTH: 70
<212> TYPE: DNA
<213> ORGANISM: Artificial sequence
<220> FEATURE:
<223> OTHER INFORMATION: Primer

<400> SEQUENCE: 47
tagccaaatg cgttggcaaa cagagattgt gttttttctt tcagactcat ctttgtttcc    60
tccgaattcg                                                          70

<210> SEQ ID NO 48
<211> LENGTH: 70
<212> TYPE: DNA
<213> ORGANISM: Artificial sequence
<220> FEATURE:
<223> OTHER INFORMATION: Primer

<400> SEQUENCE: 48
cggttcgacg catgcaggca tgaaaccgcg tctttttca gataaaaagc catatgaata     60
tcctccttag                                                          70

<210> SEQ ID NO 49
<211> LENGTH: 70
<212> TYPE: DNA
<213> ORGANISM: Artificial sequence
<220> FEATURE:
<223> OTHER INFORMATION: Primer

<400> SEQUENCE: 49
accaatcaaa ttcacgcggc caggcgcctg aatggtgtga gtggcagggt agccaaatgc    60
gttggcaaac                                                          70

<210> SEQ ID NO 50
<211> LENGTH: 70
<212> TYPE: DNA
<213> ORGANISM: Artificial sequence
<220> FEATURE:
<223> OTHER INFORMATION: Primer

<400> SEQUENCE: 50
gtcggtagtg ctgaccttgc cggaggcggc cttagcaccc tctccggcca acggttcgac    60
gcatgcaggc                                                          70

<210> SEQ ID NO 51
<211> LENGTH: 1841
<212> TYPE: DNA
<213> ORGANISM: Escherichia coli

<400> SEQUENCE: 51

```
agcatgatcg aaacacatcat gcagtcgatg caattcccgg cggaattgat tgagaaggtt    60
tgcggaacta tctaaaacgt tgcagacaaa ggacaaagca atggcaatcc acaatcgtgc   120
aggccaacct gcacaacaga gtgatttgat taacgtcgcc caactgacgg cgcaatatta   180
tgtactgaaa ccagaagcag ggaatgcgga gcacgcggtg aaattcggta cttccggtca   240
ccgtggcagt gcagcgcgcc acagctttaa cgagccgcac attctggcga tcgctcaggc   300
aattgctgaa gaacgtgcga aaaacggcat cactggccct tgctatgtgg gtaaagatac   360
tcacgccctg tccgaacctg cattcatttc cgttctggaa gtgctggcag cgaacggcgt   420
tgatgtcatt gtgcaggaaa acaatggctt caccccgacg cctgccgttt ccaatgccat   480
cctggttcac aataaaaaag gtggcccgct ggcagacggt atcgtgatta caccgtccca   540
taacccgccg aagatggtg gaatcaaata caatccgcca aatggtggcc cggctgatac   600
caacgtcact aaagtggtgg aagacagggc caacgcactg ctggccgatg gcctgaaagg   660
cgtgaagcgt atctccctcg acgaagcgat ggcatccgt catgtgaaag agcaggatct   720
ggtgcagccg ttcgtggaag gtctggccga tatcgttgat atggccgcga ttcagaaagc   780
gggcctgacg ctgggcgttg atccgctggg cggttccggt atcgaatact ggaagcgtat   840
tggcgagtat tacaacctca acctgactat cgttaacgat caggtcgatc aaaccttccg   900
ctttatgcac cttgataaag acggcgcgat ccgtatggac tgctcctccg agtgtgcgat   960
ggcgggcctg ctggcactgc gtgataagtt cgatctggcg tttgctaacg acccggatta  1020
tgaccgtcac ggtatcgtca ctccggcagg tttgatgaat ccgaaccact acctggcggt  1080
ggcaatcaat tacctgttcc agcatcgtcc gcagtgggc aaagatgttg ccgtcggtaa  1140
aacgctggtt tcatctgcga tgatcgaccg tgtggtcaac gacttgggcc gtaaactggt  1200
agaagtcccg gtaggtttca atggtttgt cgatggtctg ttcgacggca gcttcggctt  1260
tggcggcgaa gagagtgcag gggcttcctt cctgcgtttc gacggcacgc cgtggtccac  1320
cgacaaagac ggcatcatca tgtgtctgct ggcggcggaa atcaccgctg tcaccggtaa  1380
gaacccgcag gaacactaca cgaactggc aaaacgcttt ggtgcgccga gctacaaccg  1440
tttgcaggca gctgcgactt ccgcacaaaa agcggcgctg tctaagctgt ctccggaaat  1500
ggtgagcgcc agcaccctgg caggtgaccc gatcaccgcg cgcctgactg ctgctccggg  1560
caacggtgct tctattggcg gtctgaaagt gatgactgac aacggctggt tcgccgcgcg  1620
tccgtcaggc acggaagacg catataagat ctactgcgaa agcttcctcg gtgaagaaca  1680
tcgcaagcag attgagaaag aagcggttga gattgttagc gaagttctga aaaacgcgta  1740
aacacattta ataaaaaaag gcggtcgca agatcgccct ttttacgta tgacaaacac  1800
agaattgcct gatgcgctac gcttatcagg cctacgagga t                      1841
```

<210> SEQ ID NO 52
<211> LENGTH: 509
<212> TYPE: DNA
<213> ORGANISM: Escherichia coli

<400> SEQUENCE: 52

```
cgtacacgcg tttactttgc ggcagatgaa caaacgctgc tgaaaaatgg taatcagacc    60
aagccgaaac atgtgccagg cacgccgtat tgggtgatca ccaacaccaa caccggccgt   120
aaatgcagca tgatcgaaca catcatgcag tcgatgcaat tcccggcgga attgattgag   180
aaggtttgcg gaactatcta aaacgttgca gacaaaggaa aaagcagtgt aggctggagc   240
tgcttcgaag ttcctatact ttctagagaa taggaacttc ggaataggaa ctaaggagga   300
```

```
tattcatatg acacatttaa taaaaaaagg gcggtcgcaa gatcgccctt ttttacgtat        360
gacaaacaca gaattgcctg atgcgctacg cttatcaggc ctacgaggat ggtgcaatat        420
attgaattta agcgattttg taggccggat aaggcgttca cgccgcatcc ggcaaaaaca        480
acgaacactt tgtcaacaaa ctgagtagc                                         509
```

<210> SEQ ID NO 53
<211> LENGTH: 2061
<212> TYPE: DNA
<213> ORGANISM: Escherichia coli
<220> FEATURE:
<221> NAME/KEY: misc_feature
<222> LOCATION: (707)..(707)
<223> OTHER INFORMATION: n is a, c, g, or t

<400> SEQUENCE: 53

```
cgtacacgcg tttactttgc ggcagatgaa caaacgctgc tgaaaaatgg taatcagacc        60
aagccgaaac atgtgccagg cacgccgtat tgggtgatca ccaacaccaa caccggccgt       120
aaatgcagca tgatcgaaca catcatgcag tcgatgcaat tcccggcgga attgattgag       180
aaggtttgcg gaactatcta aaacgttgca gacaaaggac aaagcagtgt aggctggagc       240
tgcttcgaag ttcctatact ttctagagaa taggaacttc ggaataggaa ctaaggagga       300
tattcatatg gaccgatatc ccgggcggcc gcttcattta taaatttctt gacattttgg       360
aatagatgtg atataatgtg tacatatcca tggcggccgc tctagaagaa gcttgggatc       420
cgtcgacctc gaattcggag gaaacaaaga tgggggttc tcatcatcat catcatcatg       480
gtatggctag catgagtaaa ggagaagaac ttttcactgg agttgtccca attcttgttg       540
aattagatgg tgatgttaat gggcacaaat tttctgtcag tggagagggt gaaggtgatg       600
caacatacgg aaaacttacc cttaaattta tttgcactac tggaaaacta cctgttccat       660
ggccaacact tgtcactact ttcgggtatg gtgttcaatg ctttgcnaga tacccagatc       720
atatgaaaca gcatgacttt ttcaagagtg ccatgcccga aggttatgta caggaaagaa       780
ctatattttt caaagatgac gggaactaca agacacgtgc tgaagtcaag tttgaaggtg       840 ataccttgt taatagaatc gagttaaaag gtattgattt taaagaagat ggaaacattc       900
ttggacacaa attggaatac aactataact cacacaatgt atacatcatg gcagacaaac       960
aaaagaatgg aatcaaagtt aacttcaaaa ttagacacaa cattgaagat ggaagcgttc      1020
aactagcaga ccattatcaa caaaatactc caattggcga tggccctgtc ctttaccag       1080 acaaccatta cctgtccaca caatctgccc tttcgaaaga tcccaacgaa agagagacc       1140 acatggtcct tcttgagttt gtaacagctg ctgggattac acatggcatg gatgaactat       1200
acaaataact gcaggtcgac catatgggag agctcccaac gcgttggatg caggcatgca      1260
agcttggctg ttttggcgga tgagagaaga ttttcagcct gatacagatt aaatcagaac      1320
gcagaagcgg tctgataaaa cagaatttgc ctggcggcag tagcgcggtg gtcccacctg      1380
accccatgcc gaactcagaa gtgaaacgcc gtagcgccga tggtagtgtg gggtctcccc      1440
atgcgagagt agggaactgc caggcatcaa ataaaacgaa aggctcagtc gaaagactgg      1500
gcctttcgtt ttatctgttg tttgtcggtg aacgctctcc tgagtaggac aaatccgccg      1560
ggagcggatt tgaacgttgc gaagcaacgg cccggagggt ggcgggcagg acgcccgcca      1620
taaactgcca ggcatcaaat taagcagaag gccatcctga cggatgctac tgcgaaagct      1680
tcctcggtga agaacatcgc aagcagattg agaaagaagc ggttgagatt gttagcgaag      1740
```

| | |
|---|---|
| ttctgaaaaa cgcgtaacta ctgcgaaagc ttcctcggtg aagaacatcg caagcagatt | 1800 |
| gagaaagaag cggttgagat tgttagcgaa gttctgaaaa acgcgtaaac acatttaata | 1860 |
| aaaaaagggc ggtcgcaaga tcgccctttt ttacgtatga caaacacaga attgcctgat | 1920 |
| gcgctacgct tatcaggcct acgaggatgg tgcaatatat tgaatttaag cgattttgta | 1980 |
| ggccggataa ggcgttcacg ccgcatccgg caaaaacaac gaacactttg tcaacaaact | 2040 |
| gagtagctca aggaaatccc a | 2061 |

<210> SEQ ID NO 54
<211> LENGTH: 1735
<212> TYPE: DNA
<213> ORGANISM: Escherichia coli

<400> SEQUENCE: 54

| | |
|---|---|
| cgtacacgcg tttactttgc ggcagatgaa caaacgctgc tgaaaaatgg taatcagacc | 60 |
| aagccgaaac atgtgccagg cacgccgtat tgggtgatca ccaacaccaa caccggccgt | 120 |
| aaatgcagca tgatcgaaca catcatgcag tcgatgcaat tcccggcgga attgattgag | 180 |
| aaggttttgcg gaactatcta aaacgttgca gacaaaggac aaagcaacga aaggctcagt | 240 |
| cgaaagactg ggcctttcgt tttatctgtt gtttgtcggt gaacgctctc ctgagtagga | 300 |
| caaatccgcc gggagcggat ttgaacgttg cgaagcaacg gcccggaggg tggcgggcag | 360 |
| gacgcccgcc ataaactgcc aggcatcaaa ttaagcagaa ggccatcctg acggatggcc | 420 |
| ttttttgcgtg gccagtgcca agcttgcatg cagattgcag cattacacgt cttgagcgat | 480 |
| tgtgtaggct ggagctgctt cgaagttcct atactttcta gagaatagga acttcggaat | 540 |
| aggaacttca agatcccctc acgctgccgc aagcactcag ggcgcaaggg ctgctaaagg | 600 |
| aagcggaaca cgtagaaagc cagtccgcag aaacggtgct gaccccggat gaatgtcagc | 660 |
| tactgggcta tctggacaag gaaaacgca agcgcaaaga gaaagcaggt agcttgcagt | 720 |
| gggcttacat ggcgatagct agactgggcg gttttatgga cagcaagcga accggaattg | 780 |
| ccagctgggg cgccctctgg taaggttggg aagccctgca agtaaactg gatggctttc | 840 |
| ttgccgccaa ggatctgatg gcgcaggga tcaagatctg atcaagagac aggatgagga | 900 |
| tcgtttcgca agatcccctc acgctgccgc aagcactcag ggcgcaaggg ctgctaaagg | 960 |
| aagcggaaca cgtagaaagc cagtccgcag aaacggtgct gaccccggat gaatgtcagc | 1020 |
| tactgggcta tctggacaag gaaaacgca agcgcaaaga gaaagcaggt agcttgcagt | 1080 |
| gggcttacat ggcgatagct agactgggcg gttttatgga cagcaagcga accggaattg | 1140 |
| ccagctgggg cgccctctgg taaggttggg aagccctgca agtaaactg gatggctttc | 1200 |
| ttgccgccaa ggatctgatg gcgcaggga tcaagatctg atcaagagac aggatgagga | 1260 |
| tcgtttcgcg cgggactctg gggttcgaaa tgaccgacca agcgacgccc aacctgccat | 1320 |
| cacgagattt cgattccacc gccgccttct atgaaaggtt gggcttcgga atcgtttttcc | 1380 |
| gggacgccgg ctggatgatc ctccagcgcg gggatctcat gctggagttc tctactgcga | 1440 |
| aagcttcctc ggtgaagaac atcgcaagca gattgagaaa gaagcggttg agattgttag | 1500 |
| cgaagttctg aaaaacgcgt aaacacattt aataaaaaaa gggcggtcgc aagatcgccc | 1560 |
| ttttttacgt atgacaaaca cagaattgcc tgatgcgcta cgcttatcag gcctacgagg | 1620 |
| atggtgcaat atattgaatt taagcgattt tgtaggccgg ataaggcgtt cacgccgcat | 1680 |
| ccggcaaaaa caacgaacac tttgtcaaca aactgagtag ctcaaggaaa tccca | 1735 |

<210> SEQ ID NO 55
<211> LENGTH: 328
<212> TYPE: PRT
<213> ORGANISM: Dictyostellium discoideum

<400> SEQUENCE: 55

Ser Ile Leu Asn Phe Ile Ser Gly Ile Asn Ser Asn Lys Ile Asn Thr
1               5                   10                  15

Pro Lys Ser Asn Asn Lys Phe Lys Glu Asn Gly Ile Arg Ile Ile
            20                  25                  30

Cys Phe Ser Lys Asp Arg Ala Phe Gln Leu Lys Glu Tyr Leu Arg Thr
            35                  40                  45

Phe Phe Lys Tyr Leu Lys Asn Asp Asp Asn Gly Asn Asp Lys Phe Glu
    50                  55                  60

Ile Ile Val Asp Val Leu Phe Thr Tyr Ser Asn Glu Lys Phe Lys Asn
65                  70                  75                  80

Ser Tyr Gln Leu Val Ile Glu Ser Phe Pro Gln Val Asn Phe Ile Lys
                85                  90                  95

Glu Glu Asn Phe Thr Asp Gln Leu Ile Asn Leu Val Gln Lys Thr Asn
            100                 105                 110

Lys Leu Glu Tyr Val Met Phe Ser Val Asp Asp Ile Leu Tyr Tyr Asn
        115                 120                 125

Glu Phe Asn Leu Lys Glu Tyr Cys Leu Ser Leu Asn Ser Glu Pro Leu
    130                 135                 140

Ala Leu Gly Phe Tyr Met Lys Leu Asn Lys Asn Ile Thr Tyr Cys His
145                 150                 155                 160

Thr Cys Asn Gln Asp Ile Thr Ile Pro Leu Asn Ser Asn Thr Ile Ser
                165                 170                 175

Arg Thr Glu Asn Asn Phe Lys Tyr Leu Lys Trp Asn Arg Asn Asp Asn
            180                 185                 190

Asp Cys Lys Lys Asp Trp Asn Tyr Pro Trp Asp Leu Cys Ser Thr Ile
        195                 200                 205

Tyr Arg Cys Asn Asp Ile Asp Ser Ile Ile Asn Gly Ile Val Lys Tyr
    210                 215                 220

Tyr Gly Ile Arg Asn Gly Ile Asn His Pro Asn Arg Phe Glu Phe Asn
225                 230                 235                 240

Gly Asn Arg Pro Ile Ile Gln Lys Gln Ile Tyr Gln Asn Lys Pro Tyr
                245                 250                 255

Cys Leu Cys Leu Ser Asp His Tyr Ser Pro Met Ser Val Val Thr Ile
            260                 265                 270

Asn Arg Val Gln Asp Val Tyr Asp Asn Pro Ile Tyr Asp Gln Thr Leu
        275                 280                 285

Ser Leu Asp Asp Leu Asp Gln Leu Leu Tyr Ser Asn Lys Ser Leu Asn
    290                 295                 300

Asp Glu Lys Tyr Lys Glu Asn Ser Leu Ser Leu Asn Phe Lys Ser Val
305                 310                 315                 320

His Ile Gly Glu Leu Phe Ile Ser
                325

<210> SEQ ID NO 56
<211> LENGTH: 300
<212> TYPE: PRT
<213> ORGANISM: Helicobacter pylori

<400> SEQUENCE: 56

Met Ala Phe Lys Val Val Arg Ile Cys Gly Gly Leu Gly Asn Gln Met

```
1               5                   10                  15
Phe Gln Tyr Ala Phe Ala Lys Ser Leu Gln Lys His Ser Asn Thr Pro
                20                  25                  30

Val Leu Leu Asp Ile Thr Ser Phe Asp Trp Ser Asn Arg Lys Met Gln
            35                  40                  45

Leu Glu Leu Phe Pro Ile Asp Leu Pro Tyr Ala Ser Ala Lys Glu Ile
        50                  55                  60

Ala Ile Ala Lys Met Gln His Leu Pro Lys Leu Val Arg Asp Ala Leu
65                  70                  75                  80

Lys Tyr Ile Gly Phe Asp Arg Val Ser Gln Glu Ile Val Phe Glu Tyr
                85                  90                  95

Glu Pro Lys Leu Leu Lys Pro Ser Arg Leu Thr Tyr Phe Tyr Gly Tyr
                100                 105                 110

Phe Gln Asp Pro Arg Tyr Phe Asp Ala Ile Ser Pro Leu Ile Lys Gln
            115                 120                 125

Thr Phe Thr Leu Pro Pro Pro Lys Ile Ile Arg Ile Ile Ile Lys
        130                 135                 140

Lys Glu Glu Glu Tyr His Arg Lys Leu Ala Leu Ile Leu Ala Ala Lys
145                 150                 155                 160

Asn Ser Val Phe Val His Ile Arg Arg Gly Asp Tyr Val Gly Ile Gly
                165                 170                 175

Cys Gln Leu Gly Ile Asp Tyr Gln Lys Lys Ala Leu Glu Tyr Met Ala
                180                 185                 190

Lys Arg Val Pro Asn Met Glu Leu Phe Val Phe Cys Glu Asp Leu Thr
            195                 200                 205

Phe Thr Gln Asn Leu Asp Leu Gly Tyr Pro Phe Met Asp Met Thr Thr
210                 215                 220

Arg Asp Lys Asp Glu Glu Ala Tyr Trp Asp Met Leu Leu Met Gln Ser
225                 230                 235                 240

Cys Gln His Gly Ile Ile Ala Asn Ser Thr Tyr Ser Trp Trp Ala Ala
            245                 250                 255

Tyr Leu Ile Glu Asn Pro Glu Lys Ile Ile Ile Gly Pro Lys His Trp
            260                 265                 270

Leu Phe Gly His Glu Asn Ile Leu Cys Lys Glu Trp Val Lys Ile Glu
        275                 280                 285

Ser His Phe Glu Val Lys Ser Gln Lys Tyr Asn Ala
        290                 295                 300
```